(12) United States Patent
Kawata et al.

(10) Patent No.: US 9,080,127 B2
(45) Date of Patent: *Jul. 14, 2015

(54) COMPOSITION, COMPOUND AND FILM FORMING METHOD

(75) Inventors: Ken Kawata, Kanagawa (JP); Saisuke Watanabe, Kanagawa (JP); Hiroshi Kawamoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 473 days.

This patent is subject to a terminal disclaimer.

(21) Appl. No.: 13/380,616

(22) PCT Filed: Jun. 23, 2010

(86) PCT No.: PCT/JP2010/060639
§ 371 (c)(1),
(2), (4) Date: Mar. 27, 2012

(87) PCT Pub. No.: WO2010/150816
PCT Pub. Date: Dec. 29, 2010

(65) Prior Publication Data
US 2012/0201962 A1 Aug. 9, 2012

(30) Foreign Application Priority Data
Jun. 24, 2009 (JP) ................. 2009-149422

(51) Int. Cl.
*B01D 19/04* (2006.01)
*F16C 33/20* (2006.01)
(Continued)

(52) U.S. Cl.
CPC .............. *C10M 145/26* (2013.01); *C07C 69/40* (2013.01); *C07C 229/16* (2013.01);
(Continued)

(58) Field of Classification Search
CPC .................. C10M 2227/02; C10M 2207/282; C07C 2101/02; C07C 317/44; C07C 69/734

USPC .......... 508/100, 202, 465; 560/124, 150, 170, 560/181, 182
See application file for complete search history.

(56) References Cited

U.S. PATENT DOCUMENTS

| 3,202,701 A | 8/1965 | Paré et al. |
| 4,772,651 A * | 9/1988 | Dunski ........................ 524/289 |

(Continued)

FOREIGN PATENT DOCUMENTS

| EP | 0 909 755 A1 | 4/1999 |
| GB | 808265 B | 1/1959 |

(Continued)

OTHER PUBLICATIONS

Brent Vernon et al., JOurnal of Biomedical Materials Research, Part A, 2003, 64A (3), pp. 447-456.*

(Continued)

*Primary Examiner* — Vishal Vasisth
(74) *Attorney, Agent, or Firm* — Buchanan, Ingersoll & Rooney PC

(57) ABSTRACT

A composition comprising at least one compound represented by the following formula (Z) is disclose.

$$A\text{-}L\text{-}\{D^1\text{-}(E)_q\text{-}D^2\text{-}(B)_m\text{—}Z^1\text{—}R\}_p \quad (Z)$$

In the formula, A represents a p-valent, linear or cyclic residue; L represents a single bond or a divalent linking group; p indicates an integer of at least 2; $D^1$ represents a carbonyl group (—C(=O)—) or a sulfonyl group (—S(=O)$_2$—); $D^2$ represents a carbonyl group (—C(=O)—), a sulfonyl group (—S(=O)$_2$—), a carboxyl group (—C(=O)O—), a sulfoxyl group (—S(=O)$_2$O—), a carbamoyl group (—C(=O)N(Alk)-), or a sulfamoyl group (—S(=O)$_2$N(Alk)-); E represents a divalent group; R represents a hydrogen atom, or a substituted or unsubstituted alkyl group having at most 7 carbon atoms; B represents oxyethylene group or the like; $Z^1$ represents a single bond, or a divalent group.

24 Claims, 7 Drawing Sheets

(51) Int. Cl.

| | | |
|---|---|---|
| C07C 69/34 | (2006.01) | |
| C07C 69/74 | (2006.01) | |
| C07C 315/00 | (2006.01) | |
| C10M 145/26 | (2006.01) | |
| C10M 159/18 | (2006.01) | |
| C07C 69/40 | (2006.01) | |
| C07C 271/22 | (2006.01) | |
| C07C 307/02 | (2006.01) | |
| C07C 309/70 | (2006.01) | |
| C07C 311/04 | (2006.01) | |
| C07C 229/16 | (2006.01) | |
| C07C 229/38 | (2006.01) | |
| C07C 233/18 | (2006.01) | |

(52) U.S. Cl.
CPC ............ *C07C 229/38* (2013.01); *C07C 233/18* (2013.01); *C07C 271/22* (2013.01); *C07C 307/02* (2013.01); *C07C 309/70* (2013.01); *C07C 311/04* (2013.01); *C10M 159/18* (2013.01); *C10M 2201/02* (2013.01); *C10M 2203/10* (2013.01); *C10M 2203/1025* (2013.01); *C10M 2205/028* (2013.01); *C10M 2205/0265* (2013.01); *C10M 2207/021* (2013.01); *C10M 2207/022* (2013.01); *C10M 2207/026* (2013.01); *C10M 2207/044* (2013.01); *C10M 2207/283* (2013.01); *C10M 2207/2825* (2013.01); *C10M 2209/103* (2013.01); *C10M 2209/104* (2013.01); *C10M 2219/00* (2013.01); *C10M 2219/068* (2013.01); *C10M 2223/00* (2013.01); *C10M 2223/045* (2013.01); *C10M 2227/09* (2013.01); *C10M 2229/02* (2013.01); *C10N 2220/022* (2013.01); *C10N 2220/04* (2013.01); *C10N 2230/02* (2013.01); *C10N 2230/06* (2013.01); *C10N 2240/02* (2013.01); *C10N 2240/10* (2013.01); *C10N 2240/401* (2013.01); *C10N 2240/58* (2013.01); *C10N 2250/10* (2013.01)

(56) References Cited

U.S. PATENT DOCUMENTS

| | | | |
|---|---|---|---|
| 5,364,956 | A | 11/1994 | Matsumoto |
| 5,898,023 | A | 4/1999 | Francisco et al. |
| 5,922,658 | A | 7/1999 | Duncan et al. |
| 5,942,475 | A | 8/1999 | Schlosberg et al. |
| 5,994,278 | A | 11/1999 | Duncan et al. |
| 7,119,056 | B2 | 10/2006 | Koch et al. |
| 2003/0166474 | A1 | 9/2003 | Winemiller et al. |
| 2005/0101667 | A1 | 5/2005 | Koch et al. |
| 2005/0176986 | A1 | 8/2005 | Matsumoto |
| 2006/0148897 | A1 | 7/2006 | Vernon et al. |
| 2006/0281874 | A1 | 12/2006 | Fitz et al. |
| 2007/0054814 | A1 | 3/2007 | Negoro et al. |
| 2007/0276121 | A1 | 11/2007 | Westergom et al. |
| 2008/0026967 | A1 | 1/2008 | Suda et al. |
| 2011/0104052 | A1* | 5/2011 | Barnett et al. ............... 424/1.21 |
| 2012/0184474 | A1 | 7/2012 | Kawata et al. |

FOREIGN PATENT DOCUMENTS

| | | | |
|---|---|---|---|
| JP | 3-169685 A | 7/1991 | |
| JP | 04-356441 A | 12/1992 | |
| JP | 05-155809 A | 6/1993 | |
| JP | 07-330670 A | 12/1995 | |
| JP | 10-289436 A | 10/1998 | |
| JP | 11-158482 A | 6/1999 | |
| JP | 2001-500549 A | 1/2001 | |
| JP | 2001-501989 A | 2/2001 | |
| JP | 2001-507334 A | 6/2001 | |
| JP | 2001-348424 A | 12/2001 | |
| JP | 2002-509563 A | 3/2002 | |
| JP | 2002-097482 A | 4/2002 | |
| JP | 2002-530476 A | 9/2002 | |
| JP | 2004-507597 A | 3/2004 | |
| JP | 2004-244593 A | 9/2004 | |
| JP | 2004-315584 A | 11/2004 | |
| JP | 2005-036223 A | 2/2005 | |
| JP | 2005-154726 A | 6/2005 | |
| JP | 2005-213377 A | 8/2005 | |
| JP | 2005-232424 A | 9/2005 | |
| JP | 2005-232470 A | 9/2005 | |
| JP | 2006-257383 A | 9/2006 | |
| JP | 2006-328127 A | 12/2006 | |
| JP | 2007-092055 A | 4/2007 | |
| WO | WO 98/10039 A1 | 3/1998 | |
| WO | WO 98/10040 A1 | 3/1998 | |
| WO | WO 98/10041 A1 | 3/1998 | |
| WO | WO 98/10043 A1 | 3/1998 | |
| WO | WO 99/49004 A1 | 9/1999 | |
| WO | WO 00/29521 A1 | 5/2000 | |
| WO | WO 03/064573 A1 | 8/2003 | |
| WO | WO 2004/024237 A2 | 3/2004 | |
| WO | WO 2009/119831 A | 10/2009 | |
| WO | WO 2009/119835 A1 | 10/2009 | |

OTHER PUBLICATIONS

Office Action issued in corresponding Japanese Application No. 2010-171904 on Aug. 13, 2014 (5 pages).
Office Action issued on May 1, 2014 in co-pending U.S. Appl. No. 13/498,437 (pp. 1-15).
Office Action from the Japanese Patent Office, issued on Jun. 10, 2014 in Japanese Patent Application No. 2010-171904, with its English language excerpt. (pp. 1-5).
International Search Report (PCT/ISA/210) issued on Oct. 5, 2010, by Japanese Patent Office as the International Searching Authority for International Application No. PCT/JP2010/060639.
Written Opinion (PCT/ISA/237) issued on Oct. 5, 2010, by Japanese Patent Office as the International Searching Authority for International Application No. PCT/JP2010/060639.
Vernon et al., "Water-borne, in situ crosslinked biomaterials from phase-segregated precursors", Journal of Biomedical Materials Research Part A, 2003, pp. 447-456.
Barus, American Journal of Science, Feb. 1983, pp. 87-97, vol. 45, No. 266.
Doolittle, "Studies in Newtonian Flow. II. The Dependence of the Viscosity of Liquids on Free-Space", Journal of Applied Physics, Dec. 1951, pp. 1471-1475, vol. 22, No. 12.
Ohno et al., "Some Observations on the Relationship between Rheological Properties of Lubricants at High Pressure and Regimes of Traction (Part 1)", The Rheological Properties of Lubricants at High Pressure, 1988, pp. 922-934.
Office Action issued on Sep. 17, 2013, by the Japanese Patent Office in corresponding Japanese Patent application No. 2009-149422, and an English Translation of the Office Action (5 pages).
Notification of Transmittal of Translation of the International Preliminary Report on Patentability(Chapter I and II) (Form PCT/IB/373 & Form PCT/IB/338) and the Written Opinion of the International Searching Authority (Form PCT/ISA/237) issued on Apr. 19, 2012, in the International Application No. PCT/JP2010/066646. (13 pages).
English Translation of the International Preliminary Report on Patentability (PCT/IB/373) issued on Jan. 17, 2012, by Japanese Patent Office as the International Searching Authority for International Application No. PCT/JP2010/060639.
Hamaguchi et al., "Studies of High-Pressure Physical Properties of Discotic Compound According to Free Volume," Preprint on the International Tribology Conference, Nov. 2005, pp. 175 and partial English translation thereof.

* cited by examiner

COMPOSITION, COMPOUND AND FILM FORMING METHOD

This application is a 371 of PCT/JP2010/060639, filed Jun. 23, 2010.

TECHNICAL FIELD

The present invention relates to a novel compound having a small increase rate of viscosity by pressure and a composition containing the same and to a method for forming a coating film using the same. The composition of the invention is useful for various technical fields inclusive of technical fields of a lubricant, a mold release agent and a detergent composition and the like. In addition, the composition of the invention is useful for an enhancement in heat or oxidation stability required for lubricants to be used for internal combustion engines such as automotive engines, etc. so as to endure long-term use under a severe condition.

BACKGROUND ART

For the purposes of reducing a coefficient of friction and suppressing wear in various friction-sliding places, lubricating oils have been used in every industrial machine.

In general, current lubricating oils are constituted so as to form a fluid film in a sliding gap under a mild friction condition (fluid lubrication condition) and to form a semi-solid coating film at a frictional interface under a severe friction condition (boundary lubrication condition). That is, the current lubricating oils contain a low-viscosity oil (namely, a base oil) capable of revealing a low coefficient of friction and a chemical which for the purpose of preventing direct contact between interfaces to be caused after the low-viscosity base oil has been broken under a sever friction condition, is able to react with an interface thereof (for example, an iron interface) to form a tough and soft boundary lubricating film capable of imparting a low coefficient of friction. Though the chemical is dissolved in the base oil, it is accumulated with time at an interface thereof due to the reaction with an interface raw material (in general, steel). However, at the same time, the chemical also reacts with the majority of the face which is not directly related to sliding, and accumulation occurs, whereby the valuable chemical is consumed. In addition, even when the chemical is consumed, the base oil does not vanish but actually remains as various decomposition products; and in many cases, such accelerates deterioration of the lubricating oil per se. Moreover, the boundary lubricating film per se formed by the reaction of the chemical is also peeled off by friction-sliding under a severe condition, and the boundary substrate per se is also peeled off; and they are floated or deposited (sludged) together with the foregoing reaction decomposition products, thereby impairing lubricating ability of the lubricating oil and causing a factor in deteriorating its expected performance. In order to prevent this matter, in general, an antioxidant, a dispersant, a cleaning agent and the like are added to a lubricant (Patent Document 1).

In the light of the above, in the majority of current lubricating oils, for the purpose of reducing the friction under an extremely severe condition (boundary lubrication condition) and also the purposes of reducing and inhibiting side effects of the added chemical, a new chemical is further added. Moreover, for the purpose of reducing a lowering of the lubricating function to be caused due to fine worn powders formed from the interface per se by the wear and decomposition floats of the chemical, a new chemical is further added. And since functions of various chemicals are related to each other in the lubricating oil, it is inevitable and unavoidable that a period of time when the lubricating oil can function as a whole and exhibit the best lubricating effect becomes short due to exhaustion and deterioration of the respective chemicals. It may be said that this is a vicious cycle of a certain kind. In consequence, it is not easy to greatly improve the composition for the purpose of improving performances of current lubricating oils.

However, all of the foregoing compounds called "chemical" are ones containing an element reactive with the iron interface, and furthermore, substances formed through a reaction between such a compound and iron have ability to reduce friction and wear thereof. The element which is essential for the lubrication is phosphorus, sulfur or a halogen and furthermore, is zinc or molybdenum working competitively and complementarily. The former three are distinctly an environmentally hazardous element, and release thereof into the air even as an exhaust gas must be utterly avoided.

In addition, lubricating oils to be used for internal combustion engines, automatic transmissions and the like are required to be made low in viscosity for the purpose of achieving fuel saving, and at the same time, from the viewpoints of effective utilization of resources in recent years, reduction of waste oil, cost reduction of lubricating oil user and the like, a requirement for realization of long drain of a lubricating oil is increasing more and more. In particular, following high performances of internal combustion engines, high outputs, severe driving conditions and the like, lubricating oils for internal combustion engine (engine oils) are being required to have higher performances.

However, in conventional lubricating oils for internal combustion engine, in order to ensure heat or oxidation stability, it is generally conducted to use a highly refined base oil such as hydrocracked mineral oils, etc., or a high-performance base oil such as synthetic oils, etc. and blend the base oil with a sulfur-containing compound having peroxide decomposing ability such as zinc dithiophosphate (ZDTP), molybdenum dithiocarbamate (MoDTC), etc., or an ashless antioxidant such as such as phenol based or amine based antioxidants, etc. However, it may not be said that the heat or oxidation stability by itself is always sufficient. Moreover, though it is possible to improve the heat or oxidation stability to some extent by increasing the blending amount of the antioxidant, there is naturally a limit in an effect for enhancing the heat or oxidation stability according to this technique.

And from the viewpoint of an environmental issue such as a reduction of emission of carbon dioxide, etc., the engine oils are required to be reduced in the content of sulfur or phosphorus for the purposes of enhancing fuel-saving performance and durability and keeping catalytic ability for cleaning an exhaust gas. On the other hand, in diesel engines in recent years, though an emission control mechanism of particulate matter, such as a diesel particulate filter (DPF), etc., is started to be installed, diesel engine oils are required to realize a low ash from the standpoint of an issue of plugging of the mechanism. The realization of a low ash of engine oils means a reduction of a metallic cleaning agent, and it is an extremely important problem to ensure diesel engine cleaning properties to be kept by blending a large amount of a metallic cleaning agent or an ashless dispersant, in particular, cleaning properties of a top ring groove with a high heat load.

When an internal combustion engine is taken as an example, the foregoing lubrication is concerned with lubrication of portions other than a combustion chamber and a lubricating composition. However, as for the lubrication of the combustion chamber, there is actually a big problem, too. That is, studies for controlling (preventing or decreasing) a reduction of deposits formed in a fuel introducing port of the combustion chamber, or a reduction of friction and wear to be caused thereby, by trace additives to be added to the fuel have been continued over a period of many years.

In particular, in recent years, from the viewpoint of exhaust gas regulation, it has been becoming essential to realize a low sulfur concentration of a fuel composition. However, there is a concern that according to this, the lubricating properties are lowered, thereby causing a lowering of durability of a valve gear mechanism including cams and valves. Here, it is also driven by necessity to review the conventional element contributing to a reduction of friction and wear.

That is, in order to exhibit efficacy by small amount addition, reactivity with an interface raw material is an essential requirement, and nevertheless an element capable of revealing desired low friction by forming a boundary lubricating film is essential, at the same time, it is required to reduce sulfur, phosphorus and heavy metals, the presence per se of which is problematic. The lubricating oils are a material supporting the current industrial machines themselves, and even if they are not easily displaced, this is the moment at which a composition of lubricating oil and a lubrication mechanism per se as a background thereof must be seriously reviewed by the latest scientific technologies and functional raw material technologies after a lapse of 150 years or more.

At the beginning, while it has been described that "For the purposes of reducing a coefficient of friction and suppressing wear in various friction-sliding places, lubricating oils have been used in every industrial machine", a mission of the lubricating oil itself is to keep and preserve a motor function of machine. Though we make a machine work and utilize it, when the work (action) is taken out (counteraction), friction is inevitably caused at a mutually sliding interface. In order to reduce vigorous wear generated by the friction and prevent a mechanical damage such as seizure, etc. from occurring, it is necessary to ensure a sliding gap, and for that reason, various solid or liquid lubricating films have been applied.

A theoretical analysis of the behavior of such a liquid film in the friction state starts from the matter that the Navier-Stokes equations describing the motion of a viscous fluid in the hydrodynamics were applied to a gap with a narrow Reynolds. In those days, an experimentally verified phenomenon in which a wedge-shaped oil film in a bearing generates a high hydrodynamic pressure was theoretically explained, thereby laying the foundation of the fluid lubrication theory of the day.

According to this theory, in view of the fact that the Sommerfeld number which is utilized as a basic characteristic number of the bearing design is expressed by the following equation, it is noted that a film thickness d of a sliding gap is related to a pressure P, a viscosity η (→also correlated with a temperature T) and a sliding velocity V. Since the film thickness d itself of the sliding gap accurately depends upon an average roughness Ra of the surface thereof, it may be said that factors relating to breakage of the film thickness d of the sliding gap are the pressure P, the temperature T, the viscosity η, the average roughness Ra of the surface and the sliding velocity V.

Sommerfeld number $S=[\eta(T)*R(\text{bearing radius})*V(\text{velocity})]/[2\pi P(\text{pressure})*d^2(\text{gap})]$      [Numerical Formula 1]

From the viewpoint of keeping the oil film, as for the factors influencing the gap d, it may be easily analogized that at a high temperature, factors of a reduction of the viscosity of the oil film and an interface roughness are important and that under a high pressure, the pressure and the pressure dependency of the oil film viscosity are naturally important.

In consequence, the history of a technology for keeping a liquid film started from control of the viscosity of a base oil. First of all, in order to prevent breakage, an oil with relatively high viscosity, namely a highly viscous oil is used. However, a machine must start up, and at that time, a high viscosity is disadvantageous. Furthermore, in general, at the start-up time, the temperature is lower than that at the operation time, in most cases, the oil hardly moves because of its extremely high viscosity; and therefore, in a sense of utterly avoiding breakage at the high-temperature time, a high viscosity index oil which is originally low in viscosity was used, and furthermore, a polymer (viscosity index improver) was added to a low-viscosity base oil.

The technology developed in response to severer conditions at a high temperature and under a high pressure is a technology concerning an interface protective film (boundary lubricating film) capable of firmly adhering directly to an interface, in particular an iron interface and having flexibility. Historically, starting from the addition of a soap, inorganic films such as iron chloride, iron sulfide, iron phosphate, etc. were formed; and in recent years, reactive and low-friction organometallic complexes such as Mo-DTC, Zn-DTP, etc. have been developed, and a trace amount thereof is added to a base oil.

Though there were an improvement of viscosity physical properties against the temperature as described previously and a technical development of forming a lubricating film by another method, a technical and simple approach as in the invention, in which a viscosity-pressure modulus is controlled and optimized for the purpose of inhibiting breakage of an oil film while controlling the viscosity against the pressure has not been revealed yet.

However, the theory concerning the viscosity-pressure modulus has been surely established with the times.

As for the friction mechanism, there is known an elastic fluid lubrication mechanism between the foregoing mild fluid lubrication mechanism and severe boundary lubrication mechanism. A theoretical study of this elastic fluid lubrication mechanism started from the study regarding the true contact face shape and the generated pressure, published by Hertz in 1882; established by a summary of the EHL elastic fluid lubrication theory by Petrosevich in 1951; and became a practical theory by an oil film formation theory taking into consideration of elastic deformation by Dowson/Higginson in 1968.

A region where this elastic fluid lubrication mechanism works is a friction region under a high pressure of, for example, several tons per $cm^2$, namely about several hundred MPa. At a glance, though such a condition is severe, in fact, since iron starts to cause elastic deformation within such a pressure range, the area of the true contact face of the iron interface coming into contact with the oil film increases, and the substantial pressure becomes low. That is, within this region, so far as an elastic limit of iron or oil film breakage is not caused, the coefficient of friction does not increases, and it may be said that such a region is a "blessed region" for the sliding interface. Moreover, at the same time, in this region, an oil film made of a general lubricating oil such as mineral oils becomes high in viscosity by about 1,000 times that at the time of atmospheric pressure, but there may be the case where it becomes low in viscosity by only about 500 times depending upon a chemical structure of the raw material. Barus expressed this phenomenon relative to pressure dependency of the viscosity of liquid in terms of the following equation (VII) and exhibited that an increase rate a of viscosity which is inherent in the substance to pressure is related (Non-Patent Document 1).

$\eta = \eta_0 \exp(\alpha P)$      (VII)

Here, $\alpha$ represents a viscosity-pressure modulus; and $\eta_0$ represents a viscosity at atmospheric pressure.

Moreover, Doolittle advocated a thought of a free volume model that a viscosity of liquid is determined by a ratio of an occupied volume of molecule occupied in a liquid volume and a free volume generated by thermal expansion (Non-Patent Document 2).

$$\eta = A \exp(BV_0/V_f) \tag{VIII}$$

Here, $\eta$ represents a viscosity; $V_0$ represents an occupied volume of molecule; and $V_f$ represents a free volume.

In comparison between the equation (VIII) of Doolittle and the equation (VII) of Barus, it is noted that the viscosity-pressure modulus $\alpha$ is in inverse proportion to the free volume of molecule. That is, what the viscosity-pressure modulus is small suggests that the free volume of molecule is large. In consequence, it is noted that it is possible to control the pressure dependency of the viscosity of liquid by optimizing a chemical structure of raw material, namely, it is possible to provide a raw material having a lower viscosity than oils constituting current lubricating oils under the same high-load and high-pressure conditions by optimizing the chemical structure. For example, assuming that an oil film of a true contact part is formed by a raw material having a viscosity-pressure modulus $\alpha$ of about a half of that of mineral oils or hydrocarbon based chemical synthetic oils such as poly-$\alpha$-olefins, which are usually used as a lubricating oil, this elastic fluid lubrication region is laid under a milder condition. That is, in usual lubricating oils, even under a high load which is classified into the boundary lubrication region, in view of the fact that a cooling effect by an oil film as well as low pressure and low viscosity of the true contact site is added due to the elastic deformation of the interface and the low-viscosity oil film under a high pressure, it is expected to substantially avoid the boundary lubrication region and realize an ideal lubrication mechanism made of only fluid lubrication.

In recent years, it is disclosed that discotic compounds having a plurality of radially arranged relatively long carbon chains and lubricating oils containing the same (namely, a metallic raw material-free lubricating oil) exhibit a low coefficient of friction in the elastic fluid lubrication region (for example, Patent Documents 2 to 4). Such a discotic compound has a discotic core and side chains radially extending from the discotic core, and it is expected that a sector-shaped free volume can be inevitably ensured in a highly arranged state, too. In consequence, discotic or tabular compounds having radially arranged side chains have many free volumes in common as compared with an occupied volume thereof, and therefore, they exhibit a small viscosity-pressure modulus. That is, it is expected that the viscosity is relatively small even under a high pressure, and lower viscosity and lower friction properties are revealed under a high pressure (Non-Patent Document 3).

However, what is common among these raw materials is the matter that the viscosity thereof is larger by one digit than that of mineral oils and chemical synthetic oils usually used for lubricating oils, and it is absolutely impossible to use a large amount of such a raw material inexpensively in place of low-viscosity base oils.

That is, though the viscosity under a high pressure is defined by the viscosity $\eta_0$ and the viscosity-pressure modulus $\alpha$ as expressed by the foregoing equation (VII), when a low-viscosity base oil is actually used, it already starts to be broken in an elastic fluid lubrication region, and it becomes in a viscosity-free state, namely an elasto-plastic body under a high pressure. It has been elucidated that easiness of breakage of this lubricating oil film is correlated with an agglomerated state of fluid molecules, namely a packing state of lubricating oil molecules and can be evaluated by a product $\alpha P$ of the viscosity-pressure modulus $\alpha$ and the pressure P (Non-patent Document 4).

In general, the lubricating oil film acts as a viscous fluid when the product $\alpha P$ is not more than 13, as a visco-elastic fluid when the product $\alpha P$ is between 13 and 25 and as an elasto-plastic body when the product $\alpha P$ is 25 or more, respectively. In the case where two kinds of lubricating oil films having the same viscosity $\eta$ under a certain pressure P, where a viscosity-pressure modulus is defined as $\alpha_1$ and $\alpha_2$, respectively, and also a normal pressure viscosity is defined as $\eta_1$ and $\eta_2$, respectively, the following equation is established.

$$ln\eta = ln\eta_1 + \alpha_1 \cdot P = ln\eta_2 + \alpha_2 \cdot P$$

In the case of $18 = \alpha_1 \cdot P < \alpha_2 \cdot P = 24$, namely $\alpha_1/\alpha_2 = 18/24$, it is noted that when the pressure P is increased a little more, the film having a viscosity-pressure modulus $\alpha_2$ becomes an elasto-plastic body and is more easily broken even under the same pressure at the same viscosity.

In consequence, even when a base oil having a relatively large $\eta_0$ to such extent that it can be used even in a fluid lubrication region is utilized, since the viscosity-pressure modulus $\alpha$ of an chain hydrocarbon such as mineral oils constituting a base oil is large, there is eventually a tendency that the viscosity $\eta$ under a high pressure becomes large, and it has been considered that neither base oil having a visco-elastic fluid region nor organic compound, each of which has a low $\eta_0$ capable of imparting a low coefficient of friction under fluid lubrication and a low $\alpha$ capable of imparting a low coefficient of friction under elastic fluid lubrication at the same time, is present so far.

For the time being, even if a raw material capable of clearing the foregoing restrictions could be developed, taking into consideration necessary conditions of base oils requiring large-amount feed and low costs, it is difficult to provide a raw material satisfying all of them. Therefore, as for engine oils which are essential to be low in viscosity for the purpose of achieving low fuel consumption, it may be considered that there is a background wherein a concept itself for effectively utilizing elastic fluid lubrication was not recognized. It may be said that convergence of the raw material development to a combination of a current low-viscosity based oil and a trace chemical capable of forming a boundary lubricating film as described at the beginning was an inevitable result.

Patent Documents
[Patent Document 1] JP-T-2005-516110
[Patent Document 2] JP-A-2006-328127
[Patent Document 3] JP-A-2007-92055
[Patent Document 4] JP-A-2006-257383
Non-Patent Documents
[Non-Patent Document 1] C. Barus, *Am. J. Sci.*, 45 (1893), page 87
[Non-Patent Document 2] A. K. Doolittle, *J. Appl. Phys.*, 22 (1951), 1471
[Non-Patent Document 3] Masanori HAMAGUCHI, Nobuyoshi OHNO, Kenji TATEISHI and Ken KAWATA, *Preprint of the International Tribology Conference* (Tokyo, 2005-11), page 175
[Non-Patent Document 4] Nobuyoshi OHNO, Noriyuki KUWANO and Fujio HIRANO, *Junkatsu* (Lubrication), 33, 12 (1988), 922; 929

DISCLOSURE OF THE INVENTION

Problems to be Resolved by the Invention

For solving the above-mentioned "unavoidable problem" of using an environmental load element which is reactive with iron and exhibits good lubricity so as to be concentrated around the surface of iron;

the present invention provides a lubricant composition which is low viscous on the same level as that of existing lubricant oil, and at the same time which can be nonreactive not only to iron face but also to any and every hard interface, furthermore to any friction-sliding interface and exists in a concentration such that it could function as a fluid film having a smaller viscosity under high pressure than existing materials;

and the invention is expected to significantly improve the performance of existing lubricant oil, such as environment harmonizability, high durability with nonreactivity/nondecomposability, low friction (coefficient) (therefore abrasion resistance) of fluid, cooling effect of fluid flowage, etc., by greatly changing the composition thereof.

Specifically, the invention has an object to provide a novel composition useful in various fields such as technical field of lubricant, etc.

Also the invention has an object to provide a novel film formation method capable of contributing toward the lubricity of sliding friction interface.

Also the invention has an object to provide a novel compound useful as a base oil or an additive in the technical field of lubricant, and also useful for other applications.

Means of Solving the Problems

[1] A composition comprising at least one compound represented by the following formula (Z):

$$A\text{-}L\text{-}\{D^1\text{-}(E)_q\text{-}D^2\text{-}(B)_m\text{-}Z^1\text{-}R\}_p \quad (Z)$$

wherein A represents a p-valent, linear or cyclic residue;
L represents a single bond, an oxy group, a substituted or unsubstituted oxymethylene group represented by the following formula (A-a), or a substituted or unsubstituted oxyethyleneoxy group represented by the following formula (A-b); Alk represents a hydrogen atom, a $C_1$ to $C_6$ alkyl group, or a cycloalkyl group;

—(O—C(Alk)$_2$)— (A-a)

—(O—C(Alk)$_2$C(Alk)$_2$O)— (A-b)

p indicates an integer of at least 2;
$D^1$ represents a carbonyl group (—C(=O)—) or a sulfonyl group (—S(=O)$_2$—), and $D^1$'s may be the same or different;
$D^2$ represents a carbonyl group (—C(=O)—), a sulfonyl group (—S(=O)$_2$—), a carboxyl group (—C(=O)O—), a sulfoxyl group (—S(=O)$_2$O—), a carbamoyl group (—C(=O)N(Alk)-), or a sulfamoyl group (—S(=O)$_2$N(Alk)-), and $D^2$'s may be the same or different; Alk represents a hydrogen atom, a $C_1$ to $C_6$ alkyl group, or a cycloalkyl group;
E represents a divalent group selected from the group consisting of an alkylene group, a cycloalkylene group, an alkenylene group, an alkynylene group, an arylene group, a divalent heterocyclic aromatic group, a heterocyclic non-aromatic group, an imino group, an alkylimino group, an oxy group, a sulfide group, a sulfenyl group, a sulfonyl group, a phosphoryl group and an alkyl-substituted silyl group, which may be substituted or unsubstituted, and any combinations of two or more of those groups;
q indicates an integer of 0 or more; and when q is 2 or more, E's may be the same or different;
R represents a hydrogen atom, or a substituted or unsubstituted alkyl group having at most 7 carbon atoms, and R's may be the same or different;
B represents a substituted or unsubstituted oxyethylene group, or a substituted or unsubstituted oxypropylene group, and multiple continuing B's may be the same or different;
m indicates a number of 1 or more;
$Z^1$ represents a single bond, or a divalent group selected from the group consisting of a carbonyl group, a sulfonyl group, a phosphoryl group, an oxy group, a substituted or unsubstituted amino group, a sulfide group, an alkenylene group, an alkynylene group and an arylene group, and any combinations of two or more of those groups.

[2] The composition according to [1], wherein A in the formula (Z) is a residue of pentaerythritol, glycerol, oligopentaerythritol, xylitol, sorbitol, inositol, trimethylolpropane, ditrimethylolpropane, neopentyl glycol or polyglycerin.

[3] The composition according to [1], wherein A in the formula (Z) is a group represented by any of the following (AI) to (AIII):

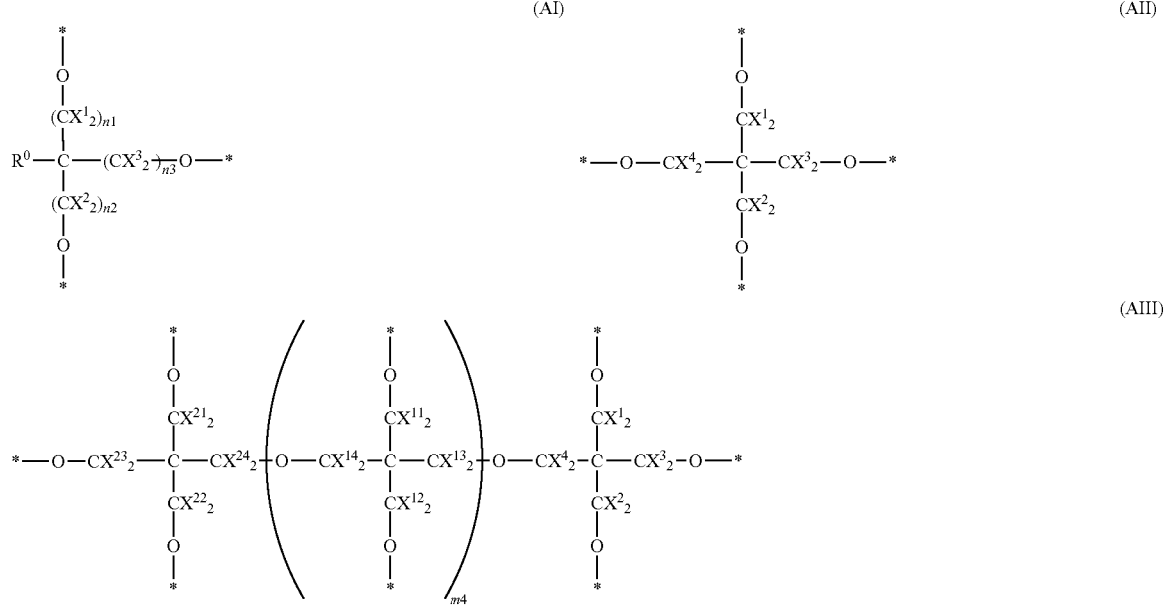

wherein * means a site at which the formula bonds to -L-D$^1$-(E)$_q$-D$^2$-(B)$_m$—Z$^1$—R; C represents a carbon atom; R$^0$ represents a hydrogen atom or a substituent; X$^1$ to X$^4$, X$^{11}$ to X$^{14}$, and X$^{21}$ to X$^{24}$ each represent a hydrogen atom, or a halogen atom, and they may be the same or different; n1 to n3 each indicate an integer of from 0 to 5; m4 indicates an integer of from 0 to 8.

[4] The composition according to [3], which comprises the compound represented by the formula (AII) in an amount of from 50 to 95% by mass, and further the compound represented by the formula (AIII) and/or the following formula (AIII') in an amount of from 5 to 50% by mass:

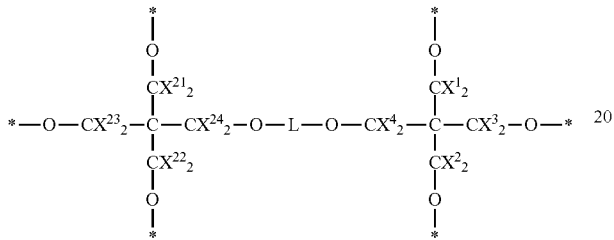

(AIII')

wherein * means a site at which the formula bonds to -D$^1$-(E)$_q$-D$^2$-(B)$_m$—Z$^1$—R; C represents a carbon atom; X$^1$ to X$^4$, X$^{11}$ to X$^{14}$, and X$^{21}$ to X$^{24}$ each represent a hydrogen atom, or a halogen atom, and they may be the same or different; L represents CH$_2$ or CO(CH$_2$)$_k$CO; k indicates an integer of from 1 to 10.

[5] The composition according to [1], wherein A in the formula (Z) is a residue of a polymer or an oligomer represented by any of the following formulae (AIV) to (AVIII):

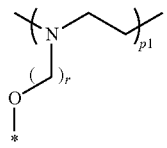

(AIV)

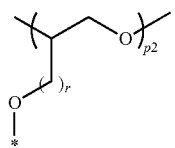

(AV)

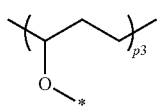

(AVI)

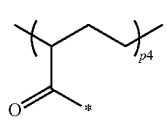

(AVII)

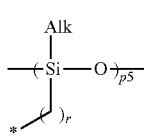

(AVIII)

wherein * means the site at which the formula bonds to -L-D$^1$-(E)$_q$-D$^2$-(B)$_m$—Z$^1$—R; the hydrogen atom bonding to the carbon atom in the formulae may be substituted with a C$_1$ to C$_4$ alkyl group or a halogen atom, and in case where the formula has 2 or more substituents, they may be the same or different; Alk represents a C$_1$ to C$_6$ alkyl group, or a cycloalkyl group; p1 to p5 each indicate a number of 2 or more; r indicates an integer of from 1 to 3.

[6] The composition according to [1], wherein A in the formula (Z) is a residue of dithiocarbamic acid or dithiophosphoric acid ion-bonding or coordinate-bonding to zinc or molybdenum.

[7] The composition according to any one of [1]-[6], wherein —(B)$_m$—Z$^1$—R in the formula (Z) is an organic group represented by the following formula (ECa), and multiple groups may be the same or different:

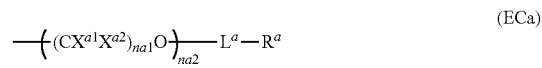

(ECa)

wherein C represents a carbon atom; O represents an oxygen atom; R$^a$ corresponding to R in the formula (Z) represents a substituted or unsubstituted alkyl group having at most 7 carbon atoms; L$^a$ corresponding to Z$^1$ in the formula (Z) represents a single bond or a divalent linking group selected from the group consisting of a carbonyl group, a sulfonyl group, a phosphoryl group, an oxy group, a substituted or unsubstituted amino group, a sulfide group, an alkenylene group, an alkynylene group and an arylene group, or any combinations of those groups; X$^{a1}$ and X$^{a2}$ each represent a hydrogen atom or a halogen atom; na1 indicates 2 or 3, and when na1 is 2 or more, multiple X$^{a1}$'s and X$^{a2}$'s may be the same or different; na2 indicates a number of from 1 to 12.

[8] The composition according to [7], wherein L$^a$ corresponding to Z$^1$ in the formula (Z) is a divalent linking group formed of a combination of one or more selected from a single bond, a carbonyl group, a sulfonyl group, a phosphoryl group, an oxy group, a substituted or unsubstituted amino group, a thio group, an alkylene group, an alkenylene group, an alkynylene group, and an arylene group.

[9] The composition according to any one of [1] to [8], wherein R in the formula (Z) is a group comprising a linear alkyl group having at most 4 carbon atoms.

[10] The composition according to any one of [1] to [9], wherein m of (B)$_m$ in the formula (Z) is from 2 to 6.

[11] The composition according to any one of [1] to [10], wherein the viscosity-pressure coefficient at 40° C. of the compound represented by the formula (Z) is at most 15 GPa$^{-1}$.

[12] The composition according to any one of [1] to [11], which comprises water, a linear or branched alcohol having at most 12 carbon atoms, ethylene glycol, polyethylene glycol, mineral oil, poly-α-olefin, polyol ester, (poly)phenyl ether, ionic liquid, silicone oil, fluorine oil, or at least two selected from these, along with at least one compound represented by the formula (Z).

[13] The composition according to [1], wherein the constituent elements of all the ingredients are one or more alone selected from carbon, hydrogen, oxygen and nitrogen.

[14] The composition according to any one of [1] to [13], which comprises the compound represented by the formula (Z) in an amount of at least 10% by mass.

[15] The composition according to any one of [1] to [14], which has a viscosity at 40° C. of at most 30 mPa·s.

[16] The composition according to any one of [1] to [12] and [14] to [15], which further comprises at least one selected from organic zinc compounds, molybdenum compounds, organic phosphorus compounds and organic sulfur compounds.

[17] The composition according to any one of [1] to [16], which is used for lubrication of the sliding interface of inorganic materials or their porous materials, or resins or their porous materials.

[18] The composition according to any one of [1] to [17], which is a mold release agent.

[19] The composition according to any one of [1] to [17], which is a fuel for combustion engines.

[20] The composition according to any one of [1] to [17], which is an internal combustion engine oil.

[21] The composition according to any one of [1] to [17], which is a bearing oil.

[22] The composition according to any one of [1] to [17], which is a grease oil.

[23] The composition according to any one of [1] to [17], which is a cutting oil.

[24] A method for forming a coating film, which comprises disposing the composition of any one of [1] to [23] between two faces and sliding the two faces to thereby form a coating film of the composition on at least one of the faces.

[25] A compound represented by the following formula (Z'):

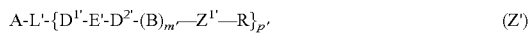

wherein A represents a p-valent, linear or branched residue; L' represents a single bond or an oxy group;
  p' indicates an integer of 3 or more;
  $D^{1'}$ represents a carbonyl group (—C(=O)—);
  $D^{2'}$ represents a carbonyl group (—C(=O)—) or a carbamoyl group (—C(=O)N(Alk)-), and $D^{2'}$'s may be the same or different;
Alk represents a hydrogen atom, a $C_1$ to $C_6$ alkyl group or a cycloalkyl group;
E' represents a single bond, a substituted or unsubstituted, $C_1$ to $C_3$ alkylene group or $C_2$ to $C_3$ alkenylene group, or -Alk'-N($R^a$)— (Alk' represents a $C_1$ to $C_3$ alkylene group, $R^a$ represents a hydrogen atom or a $C_1$ to $C_3$ alkyl group);

R represents a hydrogen atom, or a substituted or unsubstituted alkyl group having at most 7 carbon atoms; and R's may be the same or different;
B represents a substituted or unsubstituted oxyethylene group, a substituted or unsubstituted oxypropylene group, and multiple continuing B's may be the same or different;
m' indicates a number of from 1 to 30;
$Z^{1'}$ represents a single bond, an oxy group, or a carbonyl group.

[26] The compound according to [25], wherein A in the formula (Z) is a residue of pentaerythritol, glycerol, oligopentaerythritol, xylitol, sorbitol, inositol, trimethylolpropane, ditrimethylolpropane, neopentyl glycol or polyglycerin.

[27] The compound according to [25], wherein A in the formula (Z) is a group represented by any of the following (AI) to (AVIII):

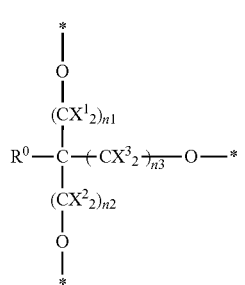

(AI)

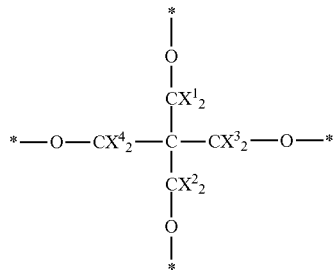

(AII)

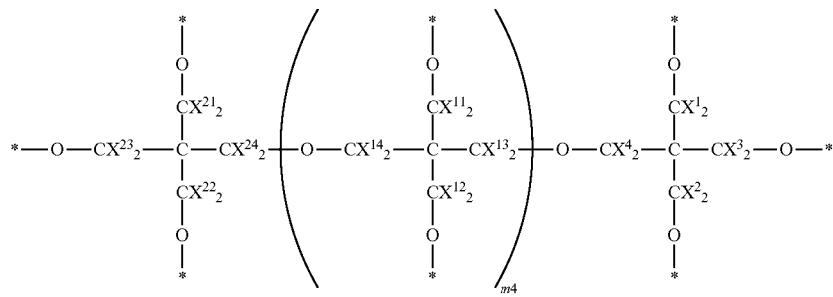

(AIII)

wherein * means a site at which the formula bonds to -$D^{1'}$-($E'$)$_q$-$D^{2'}$-(B')$_{m'}$—$Z^{1'}$R; C represents a carbon atom; $R^0$ represents a hydrogen atom or a substituent; $X^1$ to $X^4$, $X^{11}$ to $X^{14}$, and $X^{21}$ to $X^{24}$ each represent a hydrogen atom, or a halogen atom, and they may be the same or different; m4 indicates an integer of from 0 to 2;

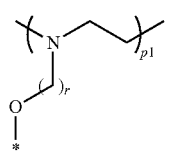

(AIV)

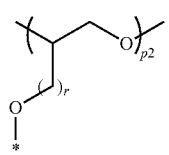

(AV)

13

-continued

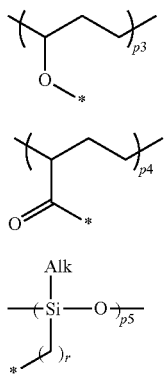

(AVI)

(AVII)

(AVIII)

wherein * means the site at which the formula bonds to -L'-D$^{1'}$-(E')$_q$-D$^{2'}$-(B')$_{m'}$—Z$^{1'}$—R; the hydrogen atom bonding to the carbon atom in the formulae may be substituted with a C$_1$ to C$_4$ alkyl group or a halogen atom, and in case where the formula has 2 or more substituents, they may be the same or different; Alk represents a C$_1$ to C$_6$alkyl group, or a cycloalkyl group; p1 to p5 each indicate a number of 2 or more; r indicates an integer of from 1 to 3.

[28] The compound according to any one of [25] to [27], wherein *-L'-{D$^{1'}$-E'-D$^{2'}$-(B)$_{m'}$—Z$^{1'}$—R} in the formula (Z) is any of the following groups (a) to (b):

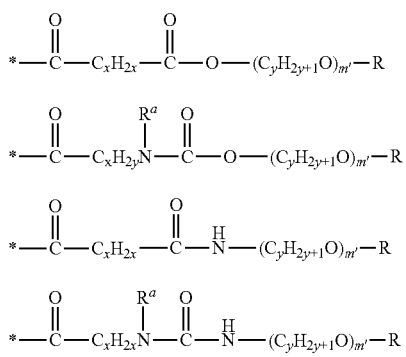

wherein x indicates an integer of from 1 to 3; y indicates 2 or 3; m', R$^a$ and R have the same meanings as those in the formula (Z').

Advantage of the Invention

According to the invention, it is possible to provide a novel composition useful in various fields such as technical field of lubricant, etc. The composition of the invention exhibits a small friction coefficient under the temperature and the pressure falling within the wide range, and therefore, it is useful in various technical fields such as a lubricant technical field relating to friction or slide.

According to the invention, it is possible also to provide a novel film formation method capable of contributing toward the lubricity of sliding friction interface.

According to the invention, it is possible also to provide a novel compound useful as a base oil or an additive in the technical field of lubricant, and also useful for other applications.

14

MODE FOR CARRYING OUT THE INVENTION

Figure 1:
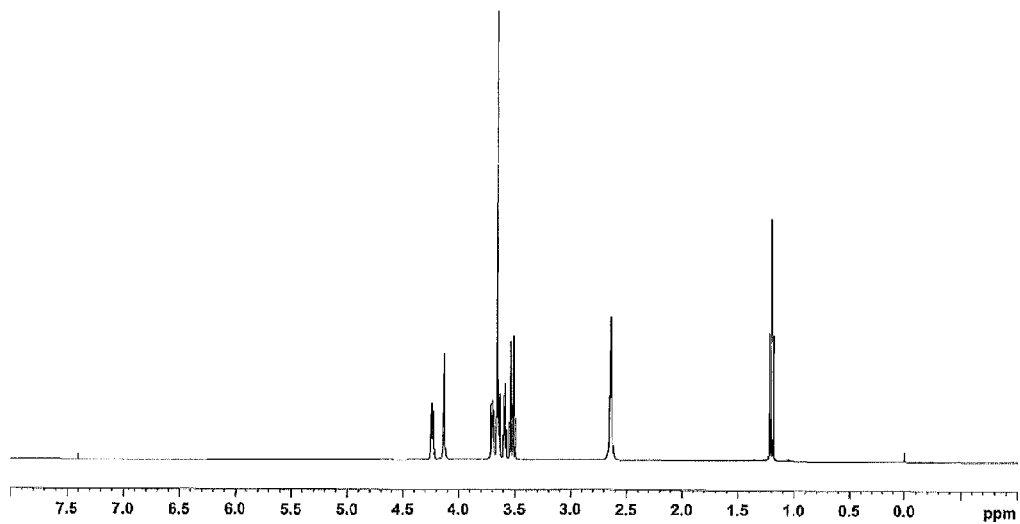
FIG. 1 This is a $^1$H-NMR pattern of a heavy chloroform sample of the rough product B synthesized in Example.

The invention is described in detail hereinunder. In this description, the numerical range expressed by the wording "a number to another number" means the range that falls between the former number indicating the lower limit of the range and the latter number indicating the upper limit thereof.

1. Compound Represented by Formula (Z)

The composition of the invention contains at least one compound represented by the following formula (Z):

$$\text{A-L-}\{D^1\text{-}(E)_q\text{-}D^2\text{-}(B)_m\text{—}Z^1\text{—}R\}_p \quad (Z)$$

In the formula, A represents a p-valent, linear or cyclic residue.

A preferred example of A is a residue that contains a branched structure where the atom within a third position (γ-position) from the atom (α-position) in A bonding to -L is secondary or more. The compound represented by the formula (Z) in which A is as above belongs to a compound group expressed as a so-called "starburst type" or "star type", and the embodiment of the invention that contains the compound of the type exhibits a preferred property as a lubricant composition.

As described above, the compound "of which the increase in the viscosity depending on pressure is small" is useful in the technical field of lubricant, and this property can be attained by the compound "of which the free volume is as large as possible" as illustrated in Non-Patent Reference 2 as described above. One example of the compound "of which the free volume is as large as possible" is a compound such that the free volume of multiple side chains existing in the molecule thereof is large.

A triphenylene compound is described as one example of a compound having a disc structure. For example, in a triphenylene having a long-chain alkoxy group at the 2, 3, 6, 7, 10 and 11-positions, the side chain of the long-chain alkoxy group naturally extends radially, and the space volume that enables free movement (free volume) is larger at the position remoter from the center part starting from the oxygen atom in the alkoxy group. Even though the compound molecules are accumulated in high density, or even though the compound has a columnar, hexagonal closed packing structure like a liquid crystal or a crystal, the smallest space for a predetermined movement of the side chain can be secured. This is a significant difference between a disc molecule and a string-like molecule, and string molecules lose the free volume thereof when aligned in a monoaxial direction.

Next discussed here is a molecule of which the structure is such that the side chain thereof extends just "starburst-like" or "star-like" and uniformly in every direction in the space from the SP3 element as the center, such as methane, tetramethylsilane, trimethylamine or the like. In these molecules, theoretically it may be possible to secure the free volume thereof like the disc-structured molecules, but the fact relatively differs. In the disc molecules mentioned previously, the disc nucleus itself originally secures the space where the side chains can freely move to some distance from the center, owing to the rigid nucleic structure thereof; but on the other hand, in the structure of the "starburst-type" or "star-type" molecules, the carbon chains extend directly from the SP3 element at the center of the molecule; and accordingly, there is a significant difference between the two.

For example, the position of the oxygen in the above-mentioned disc compound, hexylkoxytriphenylene is compared with the position of the oxygen in a "starburst-type" or "star-type" compound, trimethylolmethane triethoxylate. As schematically shown below, the oxygen corresponds to the position of nearly the fourth carbon from the SP3 carbon of the center nucleus when approximated relative to the length of the chain of the SP3 carbon, or that is, to the position of the carbon at the ethoxy group terminal. On the surface, the degree of freedom of the latter may be higher; however, when the density increases and the molecules begin to aggregate densely, then some other side chains may step into the space near to the individual side chains, or the individual side chains may bend, or the molecules may have an approximately rod-like shape like furled umbrellas to thereby reduce the free volume thereof; and in fact, it may be easily anticipated that, when the density is increased, the condition of the side chains would change in that manner.

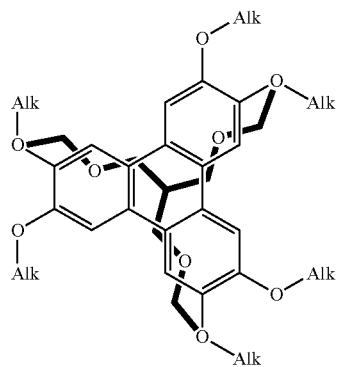

The present inventors have assiduously studied as to what structure the side chain should have, in order that even the molecule having a non-disc nucleus such as a nucleus having the SP3 element as above or the like, the side chain thereof could secure a large space volume like the side chain of a disc molecule; and on the basis of the findings the inventors have obtained as a result of the studies, the inventors have completed the present invention.

The acetoxytrimethylolmethane mentioned below is one derived by esterifying the above-mentioned trimethylolmethane triethoxylate; and in the field of lubrication, the structure is a basic structure of oils and fats. Oils and fats are polyol esters of fatty acids, and have a structure capable of readily expressing a lower viscosity pressure coefficient, or that is, a lower friction coefficient under high pressure than mineral oil.

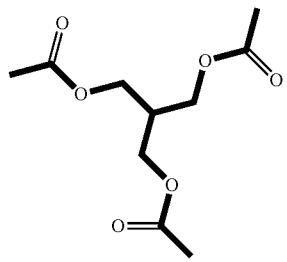

The reason is presumed to be that, when the rotation barrier energy of C—O in the ester is smaller than that of C—C therein, then the carbonyl groups could be readily radially opened owing to the electron repulsion and the steric repulsion thereof to each other, thereby securing the large free volume. Surely, a polyol ester tends to bring about lower friction than a polycarboxylate. This may be considered to be related to the size of the free energy for the rotation of C—O that has some influence on all the side chains.

However, the friction with existing ester oil is low as compared with that with mineral oil, which, however, is not so remarkable. Given the situation, the present inventors have repeatedly investigated the lubricative effect of a compound in which the side chain is further extended so as to have a carbonyl group bonding to its end, and have found that the compound mentioned below, which has a residue corresponding to succinic acid as bonded to trimethylolmethane, exhibits a remarkable friction-reducing effect.

Not only the 1,4-dicarbonyl group such as succinic acid but also a 1,3-dicarbonyl group and a 1,5-dicarbonyl group with oxygen sandwiched in the center can also exhibit the effect. In addition, a polyol ester of acylated sarcosine acid also exhibits the same friction-reducing effect.

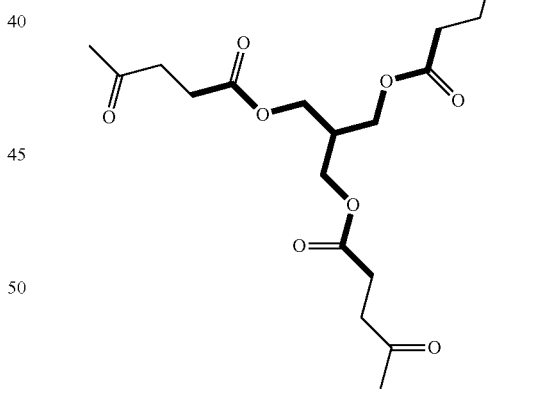

Accordingly, the present invention is a compound having a linear or cyclic chemical structure and having side chains bonding thereto and extending radially, in which the side chains secure a larger free volume of the compound. In order that the side chain can secure a large free volume thereof, preferably, the chemical structure of the compound is so planned that the side chains could enjoy easiness in free rotation around the bonding site thereof to the center nucleus so as to cause repulsion thereof to each other. In this description, the compound having side chains so planned as above is comprehensively expressed as a "starburst-type" or "star-type" compound.

In the above, described is a compound containing a SP3 carbon element and having a branched structure with the element; however, the compound of the invention is not limited in point of the structure of the center nucleus so far as the side chains thereof secure a large free volume. Needless-to-say, the compound may have a cyclic structure. In addition, a compound containing a element capable of being trivalent or more multivalent, such as nitrogen, silicon, boron, phosphorus or the like, in which side chains having a predetermined phosphoryl group, an alkyl-substituted silyl group, or a divalent group comprising a combination of two or more such groups), and residues of glycerol, xylitol, sorbitol, inositol, trimethylolpropane, ditrimethylolpropane, neopentyl glycol or polyglycerin.

Preferred examples of A in the above-mentioned formula (Z) are the groups represented by any of the following formulae (AI) to (AIII):

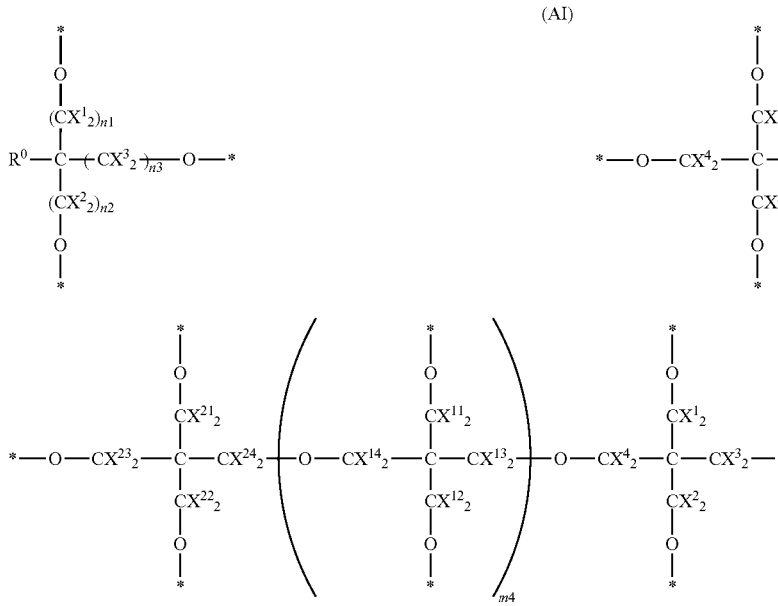

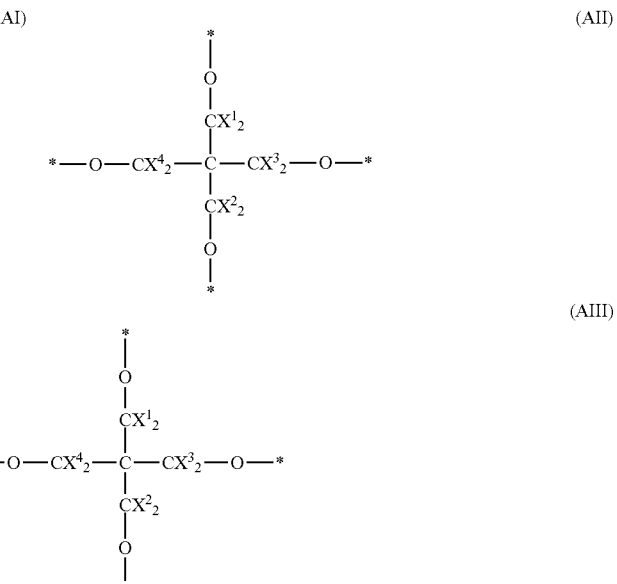

structure (-D$^1$-(E)$_q$-D$^2$-(B)$_m$—Z$^1$—R) that the compound represented by the above-mentioned formula (Z) has are linked to the center nucleus thereof containing a branched structure with the element, can secure a large free volume at the side chains, and can exhibit the same effect, and therefore the compound of the type is also usable in the invention.

The compound for use in the invention may also be a polymer or an oligomer. More concretely, a polymer or an oligomer, in which side chains having a predetermined structure (-D$^1$-(E)$_q$-D$^2$-(B)$_m$—Z$^1$—R) are linked to the side chains bonding to one or more recurring units constituting the main chain thereof, can also secures a large free volume at the side chains and can exhibit the same effect, and therefore the polymer or the oligomer is also usable in the invention. The main chain of the polymer and the oligomer may be a polyvinyl alcohol chain or the like having a simple structure, and concretely, a polymer or an oligomer derived from polyvinyl acetate by substituting the acetyl group therein with a side chain having a predetermined structure (-D$^1$-(E)$_q$-D$^2$-(B)$_m$—Z$^1$—R) that the compound represented by the formula (Z) has, can be used in the invention.

Hydrocarbon chains that are examples of the center nucleus structure to which the above-mentioned side chain bonds include residues of pentaerythritol, di-, tri-, tetra- and the like oligopentaerythritols, those constructed by bonding one hydroxyl group of pentaerythritol to any other via a divalent group (e.g., a divalent group selected from a substituted or unsubstituted alkylene, cycloalkylene, alkenylene, alkynylene group, arylene, divalent heterocyclic aromatic, or heterocyclic non-aromatic group, an imino group, an oxy group, a sulfide group, a sulfenyl group, a sulfonyl group, a In the formulae, * means a site at which the formula bonds to -D$^1$-(E)$_q$-D$^2$-(B)$_m$—Z$^1$—R; C represents a carbon atom; R$^0$ represents a hydrogen atom or a substituent; X$^1$ to X$^4$, X$^{11}$ to X$^{14}$, and X$^{21}$ to X$^{24}$ each represent a hydrogen atom, or a halogen atom (e.g., fluorine atom, chlorine atom), and they may be the same or different; n1 to n3 each indicate an integer of from 0 to 5, preferably an integer of 1 or 2; m4 indicates an integer of from 0 to 8, preferably an integer of from 0 to 2.

Examples of the substituent to be represented by R$^0$ on the formula (AI) include a substituted or unsubstituted alkyl group having from 1 to 7 carbon atoms (e.g., methyl, ethyl, or linear or branched propyl, butyl, pentyl, hexyl, heptyl), an alkenyl group having from 2 to 7 carbon atoms (e.g., propenyl, butenyl, pentenyl, hexenyl, heptenyl), a cycloalkyl group having from 3 to 7 carbon atoms (e.g., cyclopropyl, cyclobutyl, cyclopentyl, cyclohexyl, cycloheptyl), an aromatic group having at most 7 carbon atoms (e.g., phenyl, toluoyl), a heterocyclic group (preferably a residue of a hetero ring containing at least one hetero atom selected from a nitrogen atom, an oxygen atom and a sulfur atom, e.g., pyridyl, pyrimidyl, triazinyl, thienyl, furyl, pyrrolyl, pyrazolyl, imidazolyl, triazolyl, thiazolyl, imidazolyl, oxazolyl, thiadiazolyl, oxadiazolyl), or a group comprising a combination of those groups. These substituents may further have one or more substituents, if possible; and examples of the substituent include an alkoxy group, an alkoxycarbonyl group, a halogen atom, an ether group, an alkylcarbonyl group, a cyano group, a thioether group, a sulfoxide group, a sulfonyl group, an amide group, etc.

Compounds having a group of (AI) to (AIII) as A are all preferred; however, from the viewpoint of synthesis thereof, more preferred are those having a group represented by the formula (AII), or that is, pentaerythritol derivatives.

As described above, A may contain an atom capable of being trivalent or more multivalent, such as nitrogen, silicon, boron, phosphorus or the like, and may be a group that contains a branched structure with that atom. Examples of A containing a nitrogen atom include residues of triethanolamine, N,N,N',N'',N''-pentakis(2-hydroxypropyl)diethylenetriamine, etc. Examples of the triamine are those constructed through (methyl-substitute) hydroxyethylation of the imino group of a polyamine, and residues of hydroxyethylated or hydroxymethylated polyols are also examples of A. In addition, examples of A further include residues of silicic acid, boric acid and phosphoric acid.

Examples of A also include residues ion-bonding or coordinate-bonding to a metal. Concretely, there may be mentioned dithiocarbamate residues and dithiophosphate residues of metal complexes of dithiocarbamic acid or dithiophosphoric acid. Examples of A include groups of the following formula (AIX), (AXa) or (AXb).

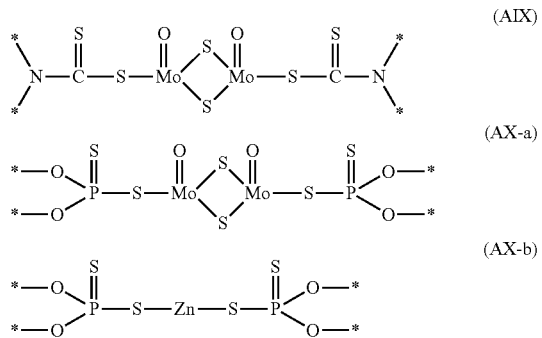

In the formulae, * means the site at which the formula bonds to $-L-D^1-(E)_q-D^2-(B)_m-Z^1-R$.

As described above, A may also be a residue of polymer or oligomer. Its structure is not specifically defined. There may be mentioned a residue of linear or cyclic polyamide substituted with an oxyalkyl group at the N-position thereof, a residue of polyoxyethylene substituted with an oxyalkyl group at the C-position thereof, a residue of polyvinyl alcohol, a residue of polyacrylate, and a dialkylsiloxy residue. A polymer or an oligomer may be used, which is obtained through polymerization of a monomer into which the side chain moiety in the above-mentioned formula (Z), or that is, $-L-D^1-(E)_q-D^2-(B)_m-Z^1-R$ has been introduced as a substituent thereof; or a polymer or an oligomer may also be used, which is obtained through polymerization of the monomer before introduction of the substituent thereinto followed by introducing the substituent into the side chain of the resulting polymer or oligomer.

For example, herein usable are a polymer or an oligomer obtained through polymerization of an acrylate having $-L-D^1-(E)_q-D^2-(B)_m-Z^1-R$ in the ester moiety thereof; and a polymer or an oligomer obtained through polymerization of an acrylate followed by modification with $-L-D^1-(E)_q-D^2-(B)_m-Z^1-R$. As examples of the polymer or oligomer represented by the formula (Z), preferred is [acryloyl group]-O—CH$_2$CH$_2$O-[side chain moiety except A in formula (Z)], and more preferred is [acryloyl group]-O—CH$_2$—O—CH$_2$-[side chain moiety except A in formula (Z)].

Similarly, a residue of polyvinyl alcohol (including oligomer) obtained through polymerization of a vinyloxy monomer or a vinyl ether;

a residue of polyethylene glycol (including oligomer) substituted with a methylol residue, which is obtained through polymerization of glycidyloxy monomer; and a residue of polysiloxane (including oligomer) obtained through hydrosilylation of a vinyloxy monomer with polymethylhydrosiloxane are contained in examples of A in the formula (Z).

More concretely, examples of A includes residues of a polymer or an oligomer represented by the following (AIV) to (AVIII):

In the formulae, * means the site at which the formula bonds to $-L-D^1-(E)_q-D^2-(B)_m-Z^1-R$; the hydrogen atom bonding to the carbon atom in the formulae may be substituted with a $C_1$ to $C_4$ alkyl group or a halogen atom, and in case where the formula has 2 or more substituents, they may be the same or different; Alk represents a $C_1$ to $C_6$ alkyl group, or a cycloalkyl group; p1 to p5 each indicate a number of 2 or more; r indicates an integer of from 1 to 3. Preferably, p1 to p5 each are from 3 to 40, more preferably from 5 to 20.

In the formula (Z), L represents a single bond, an oxy group, a substituted or unsubstituted oxymethylene group represented by the following formula (A-a), or a substituted or unsubstituted oxyethyleneoxy group represented by the following formula (A-b). In the following formulae, Alk represents a hydrogen atom, a $C_1$ to $C_6$ alkyl group, or a cycloalkyl group.

In the formula (Z), $D^1$ represents a carbonyl group (—C(=O)—) or a sulfonyl group (—S(=O)$_2$—), and $D^1$'s may be the same or different; $D^2$ represents a carbonyl group (—C(=O)—), a sulfonyl group (—S(=O)$_2$—), a carboxyl group (—C(=O)O—), a sulfoxyl group (—S(=O)$_2$O—), a carbamoyl group (—C(=O)N(Alk)-), or a sulfamoyl group (—S(=O)$_2$N(Alk)-). Alk represents a hydrogen atom, a C$_1$ to C$_6$ alkyl group, or a cycloalkyl group.

In the formula (Z), E represents a divalent group comprising a combination of one or more selected from a single bond, a substituted or unsubstituted alkylene group (preferably C$_1$ to C$_8$ alkylene group, for example, methylene, ethylene, propylene, butylene, pentylene, hexylene, heptylene, octylene), a cycloalkylene group (preferably C$_3$ to C$_{15}$ cycloalkylene group, for example, cyclopropylene, cyclobutylene, cyclopentylene, cyclohexylene), an alkenylene group (preferably C$_2$ to C$_8$ alkenylene group, for example, ethene, propene, butene, pentene), an alkynylene group (preferably C$_2$ to C$_8$ alkynylene group, for example, ethyne, propyne, butyne, pentyne), an arylene group (preferably C$_6$ to C$_{10}$ arylene group, for example, phenylene), a divalent heterocyclic aromatic group, a heterocyclic non-aromatic group, or a substituted or unsubstituted imino group, an oxy group, a sulfide group, a sulfenyl group, a sulfonyl group, a phosphoryl group, and an alkyl-substituted silyl group.

q indicates an integer of 0 or more; and when q is 2 or more, E's may be the same or different.

Preferred examples of -D$^1$-(E)$_q$-D$^2$- in the formula (Z) include the following groups:

In the formulae, * indicates the site at which the group bonds to L in the formula; and ** indicates the site at which the group bonds to B in the formula. D$^{11}$ and D$^{12}$ each represent a carbon atom or S(=O), preferably a carbon atom. E$^1$ represents a single bond, a linear or branched, substituted or unsubstituted C$_1$ to C$_5$ alkylene group, C$_2$ to C$_8$ alkenylene group or C$_2$ to C$_8$ alkynylene group (in which the carbon atom may be replaced by an oxygen atom), a substituted or unsubstituted C$_3$ to C$_{15}$ cycloalkylene, cycloalkenylene or cycloalkynylene group, a substituted or unsubstituted C$_6$ to C$_{10}$ arylene group, a substituted or unsubstituted, aromatic or non-aromatic heterocyclic group, —NH—, -Alk"-NH— (where Alk" represents a C$_1$ to C$_4$alkylene group, and the same shall apply hereinunder), —NH-Alk"-, or —NH-Alk"-NH—. Examples of the substituent for the alkylene group and others include a halogen atom (e.g., fluorine atom, chlorine atom). Preferred examples of E$^1$ include a single bond, and a divalent group such as methylene, ethylene, propylene, methyleneoxymethylene, vinylene, imino, tetrafluoroethylene, iminohexyleneimino, etc.

In the formula (Z), R represents a hydrogen atom, or a substituted or unsubstituted alkyl group having at most 7 carbon atoms.

The alkyl group having at most 7 carbon atoms for R is preferably an alkyl group having at most 4 carbon atoms, more preferably an alkyl group having at most 2 carbon atoms. The alkyl group may be linear or branched. Concretely, the group includes methyl, ethyl, propyl, isopropyl, butyl hexyl, heptyl. The alkyl group may have 1 or more substituents. Examples of the substituent include a halogen atom (e.g., fluorine atom, chlorine atom), a hydroxyl group, an amino group, an alkylamino group, a mercapto group, an alkylthio group, an alkoxy group, a cyano group, etc.

In the formula (Z), B represents a substituted or unsubstituted oxyethylene group, or a substituted or unsubstituted oxypropylene group. Multiple continuing B's may be the same or different. m indicates a natural number of 1 or more, preferably from 1 to 30, more preferably from 1 to 10, even more preferably from 1 to 8, still more preferably from 1 to 4.

B's may be the same or different; and B may be a combination of an oxyethylene group and an oxypropylene group, and/or may contain both the unit B in which the ethylene moiety or the propylene moiety is unsubstituted and the unit B in which the moiety is substituted. The ethylene moiety or the propylene moiety of the oxyethylene group or the oxypropylene group may have a substituent. Examples of the substituent include a halogen atom (e.g., fluorine atom, chlorine atom). The substituted or unsubstituted oxyethylene groups or the substituted or unsubstituted oxypropylene groups in the formula may differ in point of the chain length thereof.

In the formula (Z), Z$^1$ represents a single bond, or a divalent group selected from a carbonyl group, a sulfonyl group, a phosphoryl group, an oxy group, a substituted or unsubstituted amino group, a sulfide group, an alkenylene group, an alkynylene group and an arylene group, or a divalent group comprising a combination of two or more of those groups. The divalent linking group preferably comprises a combination of at least one selected from a carbonyl group, a sulfonyl group, a phosphoryl group, an oxy group, a substituted or unsubstituted imino group, a sulfide group, a C$_1$ to C$_6$ alkylene group, a C$_6$ to C$_{16}$ cycloalkylene group, a C$_2$ to C$_8$ alkenylene group, a C$_2$ to C$_5$ alkynylene group, a C$_6$ to C$_{10}$ arylene group, and a C$_3$ to C$_{10}$ heterocyclic group. Examples of the linking group comprising a combination of two or more those groups include —CONH—, —CO-cyclohexylene-, —CO-Ph- (in which Ph represents a phenylene group and the same shall apply hereinunder), —CO—C≡C-Ph-, —CO—CH=CH-Ph-, —CO-Ph-N=N-Ph-O—, —C$_n$H$_{2n}$—NR—, (n represents from 1 to 4 alkyl groups, R represents a hydrogen atom or a C$_1$ to C$_4$ alkyl group, and the right side of the group bonds to the terminal side of the formula), —N,N'-pyrazolidylene-.

Preferred example of —(B)$_m$—Z$^1$—R in the formula (Z) include those of the following formula (ECa):

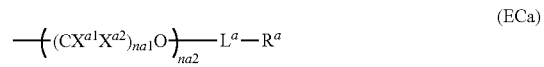

In the formula (ECa), C represents a carbon atom, O represents an oxygen atom, L$^a$ (corresponding to Z$^1$ in the formula (Z)) represents a single bond or a divalent linking group; X$^{a1}$ and X$^{a2}$ each represent a hydrogen atom, a halogen atom or a substituent (preferably a hydrogen atom or a fluorine atom, more preferably a hydrogen atom); na1 indicates 2 or 3, and multiple X$^{a1}$'s and X$^{a2}$'s may be the same or different; na2 indicates a number of from 1 to 12 (preferably from 1 to 8, more preferably from 1 to 4; R$^a$ (corresponding to R in the formula (Z)) represents a substituted or unsubstituted alkyl group having at most 7 carbon atoms (preferably at most 4 carbon atoms, more preferably at most 2 carbon atoms).

L$^a$ represents a divalent linking group comprising a combination of one or more selected from a single bond, a carbonyl group, a sulfonyl group, a phosphoryl group, an oxy group, a substituted or unsubstituted amino group, a thio group, an alkylene group, an alkenylene group, an alkynylene group, and an arylene group.

In the formula (Z), p indicates an integer of 2 or more, preferably 3 or more, more preferably from 3 to 8. The compound of the formula (Z) has multiple side chains each having a predetermined structure, therefore attaining a low friction coefficient.

The invention also relates to a compound represented by the following formula (Z'). The compound represented by the following formula (Z') is one embodiment of the compound represented by the above-mentioned formula (Z).

$$A\text{-}L'\text{-}\{D^{1'}\text{-}(E')_q\text{-}D^{2'}\text{-}(B)_m\text{-}Z^{1'}\text{-}R\}_{p'} \quad (Z')$$

In the formula, A represents a p-valent, linear or branched residue;
L' represents a single bond or an oxy group;
p' indicates an integer of 3 or more;
$D^{1'}$ represents a carbonyl group (—C(=O)—);
$D^{2'}$ represents a carbonyl group (—C(=O)—) or a carbamoyl group (—C(=O)N(Alk)-),
and $D^{2'}$'s may be the same or different;
Alk represents a hydrogen atom, a $C_1$ to $C_6$ alkyl group or a cycloalkyl group;
E' represents a single bond, a substituted or unsubstituted, $C_1$ to $C_3$ alkylene group or $C_2$ to $C_3$ alkenylene group, or -Alk'-N($R^a$)— (Alk' represents a $C_1$ to $C_3$ alkylene group, $R^a$ represents a hydrogen atom or a $C_1$ to $C_3$ alkyl group);
R represents a hydrogen atom, or a substituted or unsubstituted alkyl group having at most 7 carbon atoms; and R's may be the same or different;
B represents a substituted or unsubstituted oxyethylene group, a substituted or unsubstituted oxypropylene group, and multiple continuing B's may be the same or different;
m' indicates a number of from 1 to 30;
$Z^{1'}$ represents a single bond, an oxy group, or a carbonyl group.

In the formula (Z'), A has the same meaning as A in the formula (Z), and its examples and preferred examples are also the same as those of A in (Z).

In the formula (Z'), L' represents a single bond or an oxy group. Though depending on the type of A, in case where the terminal bonding site of A is an oxygen atom (for example, in case where A is a residue of a polyalcohol such as pentaerythritol or the like, in which H is removed from the hydroxyl group, the terminal bonding site is an oxygen atom), L' is preferably a single bond, but in case where the terminal bonding site of A is any other than an oxygen atom, L' is preferably an oxy group. Specifically, it is desirable that, in the formula (Z'), $D^1$ bonds to A via L', or not via L' (that is, U is a single bond) but via an oxy group (—O—). The same relationship shall apply to A, L and $D^1$ in the above-mentioned formula (Z).

In the formula (Z'), $D^{1'}$ represents a carbonyl group (—C(=O)—), and $D^{2'}$ represents a carbonyl group (—C(=O)—) or a carbamoyl group (—C(=O)N(Alk)-). Alk represents a hydrogen atom, a $C_1$ to $C_6$ alkyl group or a cycloalkyl group, preferably a hydrogen atom or a $C_1$ to $C_6$ alkyl group, more preferably a hydrogen atom.

In the formula (Z'), E' represents a single bond, a substituted or unsubstituted, $C_1$ to $C_3$ alkylene group or $C_2$ to $C_3$ alkenylene group, or -Alk'-N($R^a$)— (Alk' represents a $C_1$ to $C_3$ alkylene group, $R^a$ represents a hydrogen atom or a $C_1$ to $C_3$ alkyl group). E' is preferably a substituted or unsubstituted, methylene, ethylene or propylene group, more preferably an unsubstituted methylene, ethylene or propylene group.

R in the formula (Z') has the same meaning as that of R in the formula (Z), and its examples and preferred examples are also the same as those of R in (Z).

B in the formula (Z') has the same meaning as that of B in the formula (Z), and its examples and preferred examples are also the same as those of B in (Z). m' is a number of from 1 to 30, preferably a number of from 1 to 10, more preferably a number of from 1 to 8, even more preferably from 1 to 4.

In the formula (Z'), $Z^{1'}$ represents a single bond, an oxy group, or a carbonyl group, and is preferably a single bond.

In the formula (Z'), p' is an integer of at least 3, and is preferably from 3 to 8. Multiple $-\{D^{1'}\text{-}(E')_{q'\text{-}D^{2'}}\text{-}(B)_{m'}\text{-}Z^{1'}\text{-}R\}$'s may be the same or different.

In the formula (Z'), preferred examples of *-L'-{$D^{1'}$-(E')$_q$-$D^{2'}$-(B)$_m$—$Z^{1'}$—R} include the following groups (a) to (d):

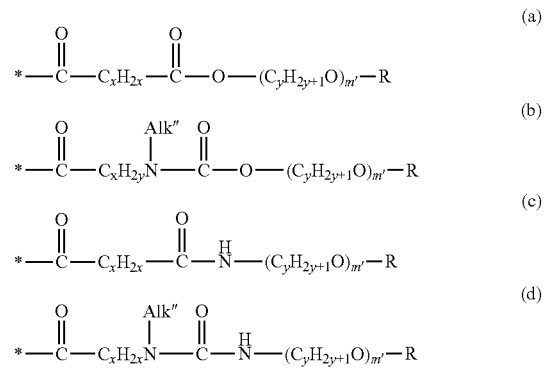

In the formulae, x indicates an integer of from 1 to 3; y indicates 2 or 3; m' indicates a number of from 1 to 30; $R^a$ represents a hydrogen atom or a $C_1$ to $C_3$ alkyl group; R represents a hydrogen atom, or a substituted or unsubstituted alkyl group having at most 7 carbon atoms. Preferred examples of the groups are the same as above.

Among them, (a) is preferred.

Examples of the compounds represented by the formula (Z) (including examples of the compounds represented by the formula (Z')) are shown below, to which, however, the invention is not limited.

(AI)

| Compound No. | $R^0$ | $Y^1=Y^2=Y^3$ | $R^1=R^2=R^3$ |
|---|---|---|---|
| AI-1 | Et | $COC_2H_4CO$ | $O(C_2H_4O)_2CH_3$ |
| AI-2 | Et | $COC_2H_4CO$ | $O(C_2H_4O)_2C_2H_5$ |
| AI-3 | Et | $COC_2H_4CO$ | $O(C_2H_4O)_3CH_3$ |
| AI-4 | Et | $COC_2H_4CO$ | $O(C_2H_4O)_3C_2H_5$ |
| AI-5 | Me | $COC_2H_4CO$ | $O(C_2H_4O)_3C_2H_5$ |
| AI-6 | Me | $COCH_2CO$ | $O(C_2H_4O)_3C_2H_5$ |
| AI-7 | Me | $COCH_2N(CH_3)CO$ | $O(C_2H_4O)_3C_2H_5$ |
| AI-8 | H | $COC_2H_4CO$ | $O(C_2H_4O)_3C_2H_5$ |
| AI-9 | Bu | $COC_2H_4CO$ | $O(C_2H_4O)_3C_4H_9$ |
| AI-10 | Et | $COCH=CHCO$ | $O(C_2H_4O)_2C_2H_5$ |
| AI-11 | $C_2F_5$ | $COC_2F_4CO$ | $O(C_2H_4O)_5C_7H_{15}$ |
| AI-12 | Et | $COCO$ | $O(C_3H_6O)_2C_4H_9$ |

(AI)

$$R^0-\underset{\underset{\underset{R^3}{Y^3}}{\underset{|}{O}}}{\overset{\overset{\overset{R^1}{Y^1}}{\overset{|}{O}}}{\overset{|}{C}}}-CH_2-O-Y^2-R^2$$

| Compound No. | R⁰ | Y¹=Y²=Y³ | R¹=R²=R³ |
|---|---|---|---|
| AI-13 | H | COC₂H₄CO | O(C₂H₄O)₂C₂H₅ |
| AI-14 | H | COC₂H₄CO | O(C₂H₄O)₃CH₃ |
| AI-15 | H | COC₂H₄CO | O(C₂H₄O)₃C₂H₅ |
| AI-16 | H | COCH₂CO | O(C₂H₄O)₃C₂H₅ |
| AI-17 | H | COCH₂N(CH₃)CO | O(C₂H₄O)₃C₂H₅ |
| AI-18 | H | COC₂H₄CO | O(C₂H₄O)₃C₄H₉ |
| AI-19 | H | COCH=CHCO | O(C₂H₄O)₂C₂H₅ |
| AI-20 | H | COC₂F₄CO | O(C₂H₄O)₃C₄H₉ |
| AI-21 | H | COC₂H₄CO | O(C₂H₄O)₃C₅H₁₁ |
| AI-22 | H | COC₂H₄CO | O(C₂H₄O)₈H |
| AI-23 | H | COC₂H₄CO | O(C₂H₄O)₄H |

(AII)

$$R^4-Y^4-O-CH_2-\underset{\underset{\underset{R^2}{Y^2}}{\underset{|}{O}}}{\overset{\overset{\overset{R^1}{Y^1}}{\overset{|}{O}}}{\overset{|}{C}}}-CH_2-O-Y^3-R^3$$

| Compound No. | Y¹=Y²=Y³=Y⁴ | R¹=R²=R³=R⁴ |
|---|---|---|
| AII-1 | COC₂H₄CO | O(C₂H₄O)₂CH₃ |
| AII-2 | COC₂H₄CO | O(C₂H₄O)₂C₂H₅ |
| AII-3 | COC₂H₄CO | O(C₂H₄O)₃CH₃ |
| AII-4 | COC₂H₄CO | O(C₂H₄O)₃C₂H₅ |
| AII-5 | COC₂H₄CO | O(C₂H₄O)₃C₄H₉ |
| AII-6 | COC₂H₄CO | O(C₂H₄O)₈CH₃ |
| AII-7 | COC₂H₄CO | O(C₂H₄O)₂₀C₄H₉ |
| AII-8 | COC₂H₄CO | O(C₂H₄O)₅C₇H₁₅ |
| AII-9 | COC₂H₄CO | O(C₂H₄O)₁₀.₅H |
| AII-10 | COC₂H₄CO | O(C₂H₄O)₄.₅C₂H₅ |
| AII-11 | COC₂H₄CO | O(C₂H₄O)₇.₃C₂H₅ |
| AII-12 | COC₂H₄CO | O(C₂H₄O)₁₀.₅C₂H₆ |
| AII-13 | COC₂H₄CO | O(C₂H₄O)₃H |
| AII-14 | COC₂H₄CO | O(C₂H₄O)₁₂.₅H |
| AII-15 | COC₂H₄CO | O(C₂H₄O)₃C₂H₅ |

(AII)

| Compound No. | Y¹=Y²=Y³=Y⁴ | R¹=R²=R³=R⁴ |
|---|---|---|
| AII-16 | COC₃H₆CO | O(C₂H₄O)₁₅C₂H₅ |
| AII-17 | COC₂H₄CO | O(C₂H₄O)₅C₇H₁₅ |
| AII-18 | COC₂F₄CO | O(C₂H₄O)₃CH₃ |
| AII-19 | COCO | O(C₂H₄O)₃C₄H₉ |
| AII-20 | COC₂H₄CO | O(C₂H₄O)₆H |
| AII-21 | COC₂H₄SO₂ | O(C₂H₄O)₃C₂H₅ |
| AII-22 | COC₂H₄CONH | (C₂H₄O)₃C₂H₅ |
| AII-23 | COC₂H₄SO₂NH | (C₂H₄O)₃C₂H₅ |
| AII-24 | COC₂H₄CON(CH₃) | (C₂H₄O)₃C₂H₅ |
| AII-25 | COCH₂N(CH₃)CO | O(C₂H₄O)₃C₂H₅ |
| AII-26 | COCH₂N(CH₃)CO | O(C₂H₄O)₂C₂H₅ |
| AII-27 | COCH₂N(CH₃)CO | O(C₂H₄O)₃C₂H₅ |
| AII-28 | COCH₂N(CH₃)CO | O(C₂H₄O)₉.₅C₄H₉ |
| AII-29 | COCH₂N(C₂H₅)CO | O(C₂H₄O)₃C₇H₁₅ |
| AII-30 | COCH₂N(cyclo-C₃H₅)CO | O(C₂H₄O)₃C₂H₅ |

(AII)

| Compound No. | Y¹=Y²=Y³=Y⁴ | R¹=R²=R³=R⁴ |
|---|---|---|
| AII-31 | COCH₂N(CH₃)CO | O(C₂H₄O)₆H |
| AII-32 | COCH₂N(CH₃)CO | O(C₂H₄O)₆H |
| AII-33 | COCH₂N(CH₃)CO | O(C₂H₄O)₁₂.₁H |
| AII-34 | COCH=CHCO | O(C₂H₄O)₉.₅C₄H₉ |
| AII-35 | COCH=CHCO | O(C₂H₄O)₆H |
| AII-36 | COCH=CHCO | O(C₂H₄O)₃CH₃ |
| AII-37 | COCH₂CO | O(C₂H₄O)₃C₂H₅ |
| AII-38 | CONHCH₂CO | O(C₂H₄O)₃C₂H₅ |
| AII-39 | CONHSO₂ | O(C₂H₄O)₃C₂H₅ |
| AII-40 | COCH₂OCH₂CO | O(C₂H₄O)₃C₂H₅ |
| AII-41 | COC₃H₆CO | O(C₂H₄O)₃C₂H₅ |
| AII-42 | COC≡CCO | O(C₂H₄O)₃C₂H₅ |
| AII-43 | COCO | O(C₂H₄O)₃C₂H₅ |
| AII-44 | COCH₂N(CH₃)CO | O(C₂H₄O)₃C₂H₅ |
| AII-45 | COC₂H₄CO | O(C₂H₄O)₄C₄H₉ |
| AII-46 | COCH=CHCO | O(C₂H₄O)₂C₂H₅ |
| AII-47 | COC₂F₄CO | O(C₂H₄O)₂C₂H₅ |

| AIII-9 | 3 | COC$_2$H$_4$CO | O(C$_2$H$_4$O)$_3$C$_2$H$_5$ |
| AIII-10 | 3 | COC$_2$H$_4$CO | O(C$_2$H$_4$O)$_{8.6}$H |

(AII)

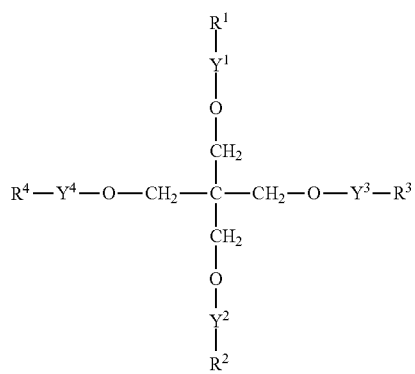

| Compound No. | Y$^1$=Y$^2$=Y$^3$=Y$^4$ | R$^1$=R$^2$=R$^3$=R$^4$ |
|---|---|---|
| AII-48 | COC$_2$H$_4$CO | O(C$_2$H$_4$O)$_6$H |
| AII-49 | COCH$_2$CO | O(C$_2$H$_4$O)$_6$H |
| AII-50 | COCH$_2$N(CH$_3$)CO | O(C$_2$H$_4$O)$_3$H |
| AII-51 | COC$_2$H$_4$CO | O(C$_2$H$_4$O)$_{20}$C$_6$H$_{13}$ |

(AIV)

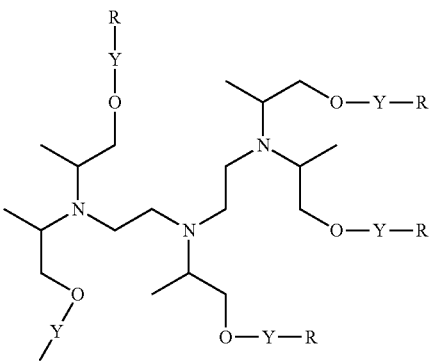

| Compound No. | Y | R |
|---|---|---|
| AIV-1 | COC$_2$H$_4$CO | O(C$_2$H$_4$O)$_2$C$_2$H$_5$ |
| AIV-2 | COC$_2$H$_4$CO | O(C$_2$H$_4$O)$_3$CH$_3$ |
| AIV-3 | COC$_2$H$_4$CO | O(C$_2$H$_4$O)$_3$C$_2$H$_5$ |
| AIV-4 | COCH$_2$CO | O(C$_2$H$_4$O)$_3$C$_4$H$_9$ |
| AIV-5 | COCH$_2$N(CH$_3$)CO | O(C$_2$H$_4$O)$_3$C$_2$H$_5$ |
| AIV-6 | COC$_2$H$_4$CO | O(C$_2$H$_4$O)$_3$C$_4$H$_9$ |
| AIV-7 | COCH=CHCO | O(C$_2$H$_4$O)$_{15.5}$C$_2$H$_5$ |
| AIV-8 | COC$_2$H$_4$CO | O(C$_3$H$_6$O)$_3$C$_4$H$_9$ |
| AIV-9 | COCO | O(C$_2$H$_4$O)$_3$C$_2$H$_5$ |
| AIV-10 | COC$_2$H$_4$CO | O(C$_2$H$_4$O)$_{8.6}$H |

(AIII)

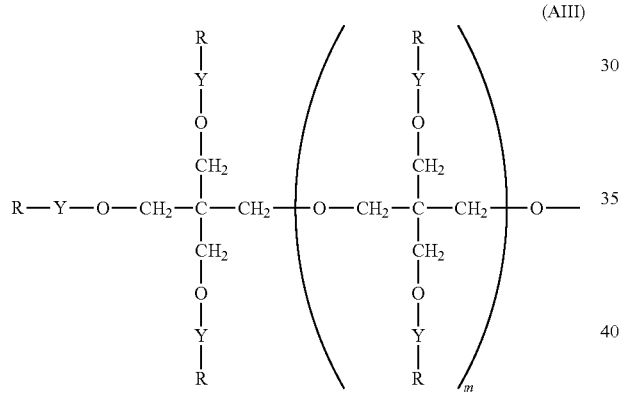

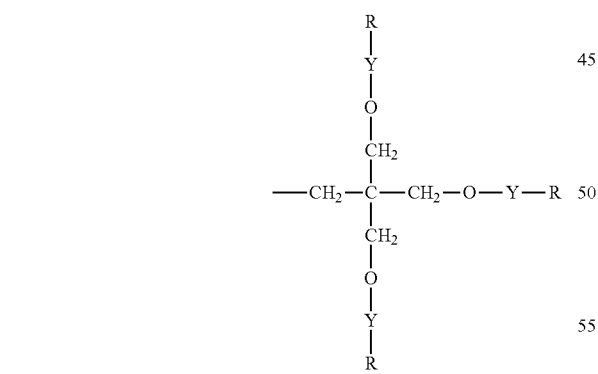

(AV)

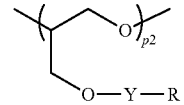

| Compound No. | p | Y | R |
|---|---|---|---|
| AV-1 | 4 | COC$_2$H$_4$CO | O(C$_2$H$_4$O)$_2$C$_2$H$_5$ |
| AV-2 | 8 | COC$_2$H$_4$CO | O(C$_2$H$_4$O)$_3$CH$_3$ |
| AV-3 | 20 | COC$_2$H$_4$CO | O(C$_2$H$_4$O)$_3$C$_2$H$_5$ |
| AV-4 | 6.7 | COCO | O(C$_2$H$_4$O)$_3$C$_2$H$_5$ |
| AV-5 | 9.6 | COCH$_2$N(CH$_3$)CO | O(C$_2$H$_4$O)$_3$C$_2$H$_5$ |
| AV-6 | 15 | COC$_2$H$_4$CO | O(C$_2$H$_4$O)$_{8.6}$H |
| AV-7 | 6.8 | COC$_2$H$_4$CO | O(C$_2$H$_4$O)$_{15.5}$C$_2$H$_5$ |
| AV-8 | 2 | COC$_2$H$_4$CO | O(C$_2$H$_4$O)$_{15.5}$C$_2$H$_5$ |
| AV-9 | 3 | COC$_2$H$_4$CO | O(C$_2$H$_4$O)$_3$C$_2$H$_5$ |
| AV-10 | 3 | COC$_2$H$_4$CO | O(C$_2$H$_4$O)$_{8.6}$H |

| Compound No. | m | Y | R |
|---|---|---|---|
| AIII-1 | 1 | COC$_2$H$_4$CO | O(C$_2$H$_4$O)$_2$C$_2$H$_5$ |
| AIII-2 | 1 | COC$_2$H$_4$CO | O(C$_2$H$_4$O)$_3$CH$_3$ |
| AIII-3 | 1 | COC$_2$H$_4$CO | O(C$_2$H$_4$O)$_3$C$_2$H$_5$ |
| AIII-4 | 1 | COCH$_2$CO | O(C$_2$H$_4$O)$_3$H |
| AIII-5 | 1 | COCH$_2$N(CH$_3$)CO | O(C$_2$H$_4$O)$_3$C$_2$H$_5$ |
| AIII-6 | 2 | COC$_2$H$_4$CO | O(C$_2$H$_4$O)$_3$C$_4$H$_9$ |
| AIII-7 | 2 | COCH=CHCO | O(C$_2$H$_4$O)$_{15.5}$C$_2$H$_5$ |
| AIII-8 | 2 | COC$_2$F$_4$CO | O(C$_2$H$_4$O)$_3$H |

(AVI)

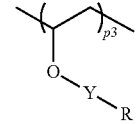

| Compound No. | q | Y | R |
|---|---|---|---|
| AVI-1 | 3.5 | COC$_2$H$_4$CO | O(C$_2$H$_4$O)$_2$C$_2$H$_5$ |
| AVI-2 | 5.8 | COC$_2$H$_4$CO | O(C$_2$H$_4$O)$_3$CH$_3$ |

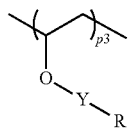

(AVI)

| Compound No. | q | Y | R |
| --- | --- | --- | --- |
| AVI-3 | 14.1 | $COC_2H_4CO$ | $O(C_2H_4O)_3C_2H_5$ |
| AVI-4 | 3.5 | $COC_2H_4CO$ | $O(C_2H_4O)_3C_4H_9$ |
| AVI-5 | 6.2 | $COCH_2N(CH_3)CO$ | $O(C_2H_4O)_3C_2H_5$ |
| AVI-6 | 3.7 | $COC_2H_4CO$ | $O(C_2H_4O)_{8.6}H$ |
| AVI-7 | 8.5 | $COC_2H_4CO$ | $O(C_2H_4O)_{15.5}C_2H_5$ |
| AVI-8 | 11.8 | $COC_2H_4CO$ | $O(C_2H_4O)_{15.5}C_2H_5$ |

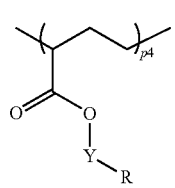

(AVII)

| Compound No. | p | Y | R |
| --- | --- | --- | --- |
| AVII-1 | 6 | $COC_2H_4CO$ | $O(C_2H_4O)_2C_2H_5$ |
| AVII-2 | 5 | $COC_2H_4CO$ | $O(C_2H_4O)_3CH_3$ |
| AVII-3 | 9.3 | $COC_2H_4CO$ | $O(C_2H_4O)_3C_2H_5$ |
| AVII-4 | 13 | $COC_2H_4CO$ | $O(C_2H_4O)_3C_4H_9$ |
| AVII-5 | 8 | $COCH_2N(CH_3)CO$ | $O(C_2H_4O)_3C_2H_5$ |
| AVII-6 | 5 | $COC_2H_4CO$ | $O(C_2H_4O)_{8.6}H$ |
| AVII-7 | 6 | $COC_2H_4CO$ | $O(C_2H_4O)_{15.5}C_2H_5$ |
| AVII-8 | 3 | $COC_2H_4CO$ | $O(C_2H_4O)_{15.5}C_2H_5$ |
| AVII-9 | 12 | $COC_2H_4CO$ | $O(C_2H_4O)_3C_2H_5$ |
| AVII-10 | 5 | $COC_2H_4CO$ | $O(C_2H_4O)_{8.6}H$ |
| AVII-11 | 20 | $COC_3H_6CO$ | $O(C_2H_4O)_{8.6}H$ |
| AVII-12 | 8 | $COCH=CHCO$ | $O(C_2H_4O)_{8.6}H$ |
| AVII-13 | 4 | $COCH_2OCH_2CO$ | $O(C_2H_4O)_{8.6}H$ |

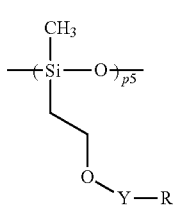

(AVIII)

| Compound No. | p5 | Y | R |
| --- | --- | --- | --- |
| AVIII-1 | 22.5 | $COC_2H_4CO$ | $O(C_2H_4O)_{4.7}C_2H_5$ |
| AVIII-2 | 22.5 | $COC_2H_4CO$ | $O(C_2H_4O)_{7.5}CH_3$ |
| AVIII-3 | 22.5 | $COC_2H_4CO$ | $O(C_2H_4O)_{10.4}C_2H_5$ |
| AVIII-4 | 22.5 | $COC_2H_4CO$ | $O(C_2H_4O)_{8.6}H$ |

Examples of the compound represented by formula (AIX), (AXa) or (AXb) include, but are not limited to, those described below.

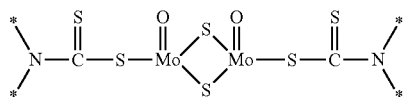

(AIX)

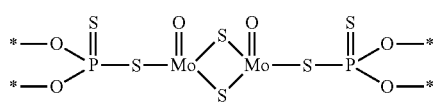

(AXa)

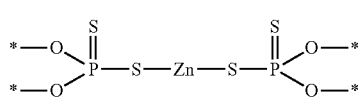

(AXb)

The partial structure connecting to "*" in the formulas is represented by "—Y—R".

| Compound No. | Structure of A | Y | R |
| --- | --- | --- | --- |
| AIX-1 | AIX | $COC_2H_4CO$ | $O(C_2H_4O)_2CH_3$ |
| AIX-2 | AIX | $COC_2H_4CO$ | $O(C_2H_4O)_2C_2H_5$ |
| AIX-3 | AIX | $COC_2H_4CO$ | $O(C_2H_4O)_3CH_3$ |
| AXa-1 | AXa | $COC_2H_4CO$ | $O(C_2H_4O)_3C_2H_5$ |
| AXa-2 | AXa | $COCH_2N(CH_3)CO$ | $O(C_2H_4O)_3C_2H_5$ |
| AXa-3 | AXa | $COC_2H_4CO$ | $O(C_2H_4O)_3C_2H_5$ |
| AXb-1 | AXb | $COC_2H_4CO$ | $O(C_2H_4O)_3C_4H_9$ |
| AXb-2 | AXb | $COC_2H_4CO$ | $O(C_2H_4O)_3C_6H_{13}$ |

The compounds represented by the above-mentioned formula (Z) can be produced by utilizing various organic synthesis reactions. For example, the compounds of the formula (Z) where A is a group represented by any of the formula (AI) to (AIII) are basically formed through linkage of a polyalcohol such as glycerol, pentaerythritol or the like and a side chain structure, but in general, esterification reaction is often used for them. For example, the compounds can be produced by combining various reactions of condensation of a polyalcohol and an acid chloride of a side chain carboxylic acid, or an isocyanate of a side chain structure, or an alkyl halide of a side chain structure, or ring-opening esterification of a polyalcohol and succinic anhydride or Meldrum's acid to give a carboxylic acid, as combined with esterification or the like of the resulting acid chloride with an alcohol of a side chain structure. The side chain structure moiety can be readily produced by using an alcohol to be obtained through addition of ethylene oxide gas to a long-chain alkyl alcohol or a carboxylic acid, or by additionally using succinic acid, Meldrum's acid or halocarboxylic acid.

The compounds in which A is a residue of pentaerythritol can be produced according to 1) a method of reacting an alcohol and a dibasic acid or its anhydride to give a carboxylic acid followed by esterifying the acid with pentaerythritol, or 2) a method of reacting pentaerythritol with a dibasic acid or its anhydride to give a tetra- or tri-carboxylic acid, followed by esterifying the acid with an alcohol.

In particular, in the reaction of pentaerythritol with succinic anhydride, the resulting tetracarboxylic cid may contain impurities in an amount of from 1 to 40%. The impurities are compounds formed through reaction of bispentaerythritol or dipentaerythritol in pentaerythritol with succinic anhydride, or compounds formed through reaction of two molecules of pentaerythritol and succinic anhydride, and mainly the following compound D is taken into consideration. Esterification, if taken along with these impurities, may give a final compound containing high-molecular-weight impurities;

however, the impurities do not have any influence on the performance of the lubricant containing them.

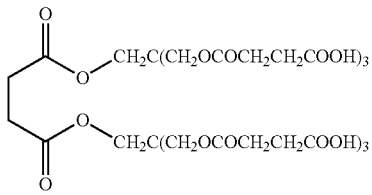

D

Specifically, when the compounds represented by the above-mentioned formula (AII) are produced according to the above-mentioned methods, there can be obtained a composition containing the intended compound along with compounds represented by the above-mentioned formula (AIII) and/or the following formula (AIII'), and the composition is also useful in the technical field of lubrication. For example, using the above-mentioned methods, there can be prepared a composition containing the compound represented by the formula (AII) in an amount of from 50 to 95% by mass, and the compounds represented by the formula (AIII) and/or the formula (AIII') in an amount of from 5 to 50% by mass.

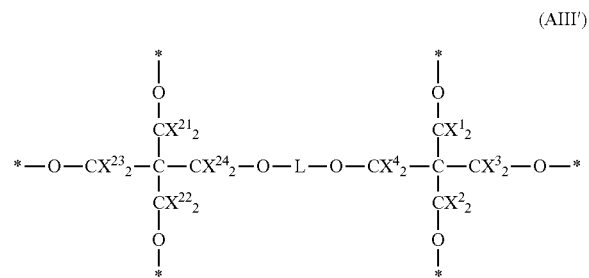

(AIII')

In the formula, * means the site at which the formula bonds to $-D^1-(E)_q-D^2-(B)_m-Z^1-R$; C represents a carbon atom; $X^1$ to $X^4$, $X^{11}$ to $X^{14}$ and $X^{21}$ to $X^{24}$ each represent a hydrogen atom or a halogen atom, and may be the same or different; L represents $CH_2$ or $CO(CH_2)_kCO$; k indicates an integer of from 1 to 10. This embodiment is preferred for use as a lubricant oil that is required to have a smaller friction coefficient. The definitions of the groups in the formula (AIII') and preferred examples thereof are the same as those in the above-mentioned formulae (Z) and (AIII). For example, in the above-mentioned compound D, L is $CO(CH_2)_2CO$.

When the viscosity-pressure coefficient of the compound represented by the formula (Z) is smaller, then the viscosity thereof under high pressure is relatively small. Preferably, the viscosity-pressure coefficient at 40° C. of the compound is at most 20 $GPa^{-1}$, more preferably at most 15 $GPa^{-1}$, even more preferably at most 10 $GPa^{-1}$. The viscosity-pressure coefficient is preferably smaller, however, it has been clarified that the coefficient is correlated with the free volume of the molecule of the compound, and it is presumed that the lower limit of the viscosity-pressure coefficient under the above-mentioned condition of the organic compound would be $GPa^{-1}$ or so.

The composition of the invention is characterized by containing the compound represented by the above-mentioned formula (Z). The compound itself represented by the formula (Z) can be used singly in the technical field of lubrication, or a composition containing the compound as the main constituent and additionally containing at least one additive can also be used in the technical field of lubrication. In addition, a composition in which the compound represented by the formula (Z) is added to the base oil can also be used in the technical field of lubrication.

The composition of the invention can be prepared as a low-viscosity fluid. The low-viscosity fluid forms a thinner film, thereby contributing toward friction reduction in fluid lubrication, and in the region of fluid lubrication, the mechanical system is driven energically at high efficiency.

Recent fuel-saving type engine oils containing a molybdenum based organometallic complex exhibit low viscosity such that a viscosity at 40° C. is not more than 30 mPa·s and are marketed as a multi-grade low-viscosity oil such as 0W-20 or the like. However, as described previously, in the composition of the invention, in view of the fact that an elastic fluid lubricating film is formed before the low-viscosity based oil is broken, the foregoing compound is able to reveal the same effects of low friction and wear resistance under a high-pressure and high-shear condition at a high temperature. Moreover, substantial low viscosity is revealed by the elastic fluid film even under such a severe condition, and the low-viscosity base oil preferentially functions under a mild condition; and therefore, an increase of the viscosity at middle to low temperatures to be caused due to a viscosity index improver as in current lubricants does not occur.

Moreover, since the composition of the invention does not basically utilize a reaction with the interface, the film forming properties thereof are not restricted by the material quality of the interface. In addition, since the foregoing compound is basically strong against heat and chemically stable, it is relatively conspicuously high in durability. Moreover, the friction portion disappears under a high-load condition, and when the temperature is high, the compound of the invention is again dispersed in the oily medium, whereby the total amount is always kept. When needed, a necessary amount of the compound is accumulated to reveal low friction, and when not needed, the compound is again dispersed; and thus, the composition of the invention is an extremely intelligent lubricant composition.

On the other hand, in the case where the foregoing compound exhibits high α, the composition effectively functions as a traction oil which is used in a site of, for example, transmitting a power by friction of a clutch, etc. In conventional high-function traction oils, hydrocarbons having an incorruptible structure, all of which have a high viscosity-pressure modulus, have been used; however, a defect thereof resides in a point that an atmospheric viscosity of the oil itself must become relatively high. This matter decreases a driving efficiency in a normal state. However, a composition in which a raw material having a high viscosity-pressure modulus among the foregoing compounds is dispersed in a low-viscosity oily medium enables one to make both fuel consumption efficiency and effective transmission of a power compatible with each other. The low-viscosity oily medium occupying the majority of the transmission oil is able to effectively reduce a friction loss due to viscosity in a region other than a driving power transmitting portion. Since the material capable of revealing a high coefficient of friction is accumulated only in a contacting portion, it is possible to reveal various combinations of an oily medium with physical properties of the compound of the invention, and it is possible to inexpensively provide a combination satisfying many requirements of a transmission.

Examples of the compounds represented by the formula (Z) include molybdenum complexes or zinc complexes in which A is the formula (AIX), (AX-a) or (AX-b). Examples of the compounds represented by the formula (Z) include those usable as a base oil. An embodiment of adding the molybdenum complex or the like represented by the formula (Z) to existing base oil, and an embodiment of using the compound represented by the formula (Z) as a base oil to which is added an existing molybdenum complex or the like both fall within the scope of the invention; and needless-to-say, an embodiment where both the base oil and the molybdenum complex or the like are the compounds represented by the formula (Z) falls within the scope of the invention.

2. Medium

The composition of the invention may contain a medium along with the compound represented by the formula (Z). The medium that may be mixed in the composition is described. In the invention, "medium" is meant to include any and every medium that is generally referred to as "flowable liquid". However, the medium is not required to be liquid at room temperature or at the service temperature, for which, therefore, any material of any other morphology such as solid, gel or the like can also be used in addition to liquid. Not specifically defined, the medium for use in the invention may be selected from various liquids depending on the use thereof. More concretely, the medium may be selected from various types of oils, for example, animal and vegetable oil and fat compounds including mineral oils for use as a base oil in lubricant oil, and edible oils; as well as various chemical synthetic oils such as polyolefin oils, alkylbenzene oils, alkylnaphthalene oils, biphenyl oils, diphenylalkane oils, di(alkylphenyl)alkane oils, ester oils, polyglycol oils, polyphenyl ether oils, fluorine compounds (perfluoropolyethers, fluoropolyolefins, etc.), silicone coils, ionic fluids, etc. In an embodiment where the composition of the invention is used in place of a lubricant oil, preferred are mineral oils, polyolefin oils and silicone oils from the viewpoint of the friction characteristics thereof. In particular, for lubrication of living bodies and bones and for rolling or cutting operation for metals and ceramics, preferred is use of a hydrophilic fluid such as water, a linear or branched alcohol having at most 12 carbon atoms, ethylene glycol, polyethylene glycol, etc.

The respective oily media are hereunder described in detail.

As the mineral oil, mineral oils obtained by a method which is usually adopted in a lubricating oil manufacturing process in the petroleum refining industry can be utilized. More specifically, paraffin based, naphthene based or other based mineral oils obtained by refining a lubricating oil fraction obtained by subjecting a crude oil to atmospheric distillation and vacuum distillation by properly combining one or two or more techniques selected among solvent deasphalting, solvent extraction, hydrocracking, solvent dewaxing, catalytic dewaxing, hydrogenation refining, sulfuric acid washing, clay treatment, etc. can be used.

Moreover, as the fat and oil, for example, beef tallow, lard, sunflower oil, soybean oil, rapeseed oil, rice-bran oil, coconut oil, palm oil, palm kernel oil and hydrogenated products thereof, etc. can be used.

As the biodegradable oil, for example, various biodegradable vegetable oils extracted from fruits, seeds or the like of plants, such as rapeseed oil, sunflower oil, soybean oil, etc. or synthetic oils can be utilized. Moreover, polyol ester oils disclosed in JP-A-6-1989 are suitably used. Even among synthetic oils, those exhibiting biodegradability such that a biodegradation rate after a lapse of 21 days is in general 67% or more (preferably 80% or more) in conformity with a method stipulated in the CEC (Coordinating European Council) Standards, L-33-T82 as an evaluation method of biodegradability, can be utilized as the biodegradable oil.

Moreover, it is preferable that the polyolefin oil is selected among those obtained by polymerizing one or two or more olefins having 2 to 12 carbon atoms. Moreover, those obtained by polymerizing one or two or more members of ethylene, propylene, 1-butene, 2-butene, isobutene and a linear terminal olefin (hereinafter referred to as "α-olefin") having from 5 to 12 carbon atoms are more preferable.

Of these, a copolymer of ethylene and propylene; a copolymer of ethylene and an α-olefin having from 5 to 12 carbon atoms; and polybutene, polyisobutene or a polymer of an α-olefin having from 5 to 12 carbon atoms are preferable; and a copolymer of ethylene and an α-olefin having from 5 to 12 carbon atoms and a polymer of an α-olefin having from 5 to 12 carbon atoms are more preferable. In this specification, the "copolymer of ethylene and an α-olefin having from 5 to 12 carbon atoms" refers to a copolymer obtained by polymerizing ethylene and one or two or more α-olefins having from 5 to 12 carbon atoms; and the "polymer of an α-olefin having from 5 to 12 carbon atoms" refers to a homopolymer obtained by polymerizing one α-olefin having from 5 to 12 carbon atoms or a copolymer obtained by polymerizing two or more α-olefins having from 5 to 12 carbon atoms.

An average molecular weight of each of the foregoing copolymer of ethylene and an α-olefin having from 5 to 12 carbon atoms and polymer of an α-olefin having from 5 to 12 carbon atoms is preferably from 500 to 4,000.

Moreover, the silicone oil can be selected among various organic polysiloxanes. Examples of the organic polysiloxane which can be used as the silicone oil include a polymer having a repeating unit represented by the following general formula:

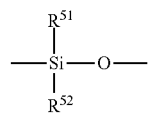

(in the formula, each of $R^{51}$ and $R^{52}$ represents an alkyl group, an aryl group or an aralkyl group, and $R^1$ and $R^2$ may be the same as or different from each other). The organic polysiloxane may be a so-called homopolymer type organic polysiloxane composed of only the subject repeating unit or may be a random type, block type or graft type organic polysiloxane composed of a combination of two or more of these repeating units. The silicone oil is preferably selected among linear polysiloxanes which are liquid or pasty at ordinary temperature, for example, methyl polysiloxane, methyl phenyl polysiloxane, ethyl polysiloxane, ethyl methyl polysiloxane, ethyl phenyl polysiloxane, hydroxymethyl polysiloxane and alkyl polydimethylsiloxanes; cyclic polysiloxanes, for example, octamethyl cyclopentasiloxane and decamethyl cyclopentasiloxane; and mixtures of these compounds.

The perfluoro polyether oil can be selected among compounds obtained by substituting a hydrogen atom of an aliphatic hydrocarbon polyether with a fluorine atom. Examples of such a perfluoro polyether oil include side chain-containing perfluoro polyethers represented by any of following formulae (Z) and (XI); and linear perfluoro polyethers represented by any of following formulae (XII) to (XIV). These compounds can be used singly or in admixture of two or more kinds thereof. In following formulae, each of m and n represents an integer.

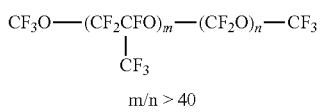

$$CF_3O-(CF_2CFO)_m-(CF_2O)_n-CF_3 \quad \text{(X)}$$
$$\underset{CF_3}{|}$$
$$m/n > 40$$

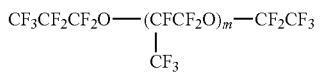

$$CF_3CF_2CF_2O-(CFCF_2O)_m-CF_2CF_3 \quad \text{(XI)}$$
$$\underset{CF_3}{|}$$

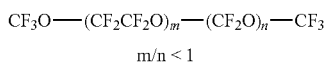

$$CF_3O-(CF_2CF_2O)_m-(CF_2O)_n-CF_3 \quad \text{(XII)}$$
$$m/n < 1$$

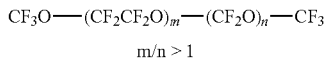

$$CF_3O-(CF_2CF_2O)_m-(CF_2O)_n-CF_3 \quad \text{(XIII)}$$
$$m/n > 1$$

$$F-(CF_2CF_2CF_2O)_n-CF_2CF_3 \quad \text{(XIV)}$$

Examples of commercially available products of the foregoing formula (Z) include FOMBLIN Y (a trade name of Montedison); examples of commercially available products of (XI) include KRYTOX (a trade name of Du Pont) and BARRIERTA J OIL (a trade name of Kluber Inc.); examples of commercially available products of (XII) include FOMBLIN Z (a trade name of Montedison); examples of commercially available products of (XIII) include FOMBLIN M (a trade name of Montedison); and examples of commercially available products of (XIV) include DEMNUM (a trade name of Daikin Industries, Ltd.), etc.

The aromatic ester oil is preferably selected among trimellitic acid ester oils represented by the following general formula (XV).

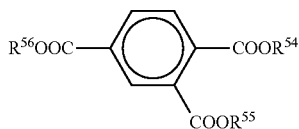

In the formula, each of $R^{54}$, $R^{55}$ and $R^{56}$ represents a hydrocarbon group having from 6 to 10 carbon atoms, and $R^{54}$, $R^{55}$ and $R^{56}$ may be the same as or different from each other. In this connection, the "hydrocarbon group" means a saturated or unsaturated, linear or branched alkyl group.

Moreover, the aromatic ester oil is preferably selected among pyromellitic acid ester oils represented by the following general formula (XVI).

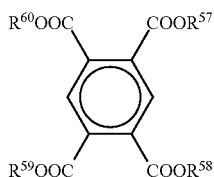

In the formula, each of $R^{57}$, $R^{58}$, $R^{59}$ and $R^{60}$ represents a hydrocarbon group having from 6 to 15 carbon atoms, and $R^{57}$, $R^{58}$, $R^{59}$ and $R^{60}$ may be the same as or different from each other. In this connection, the "hydrocarbon group" means a saturated or unsaturated, linear or branched alkyl group.

As the base oil with excellent heat resistance, though there are known a polyphenyl ether oil, a silicone oil, a fluorocarbon oil and the like, a polyphenyl ether oil, a fluorocarbon oil and a silicone oil are expensive, and a fluorocarbon oil and a silicone oil are generally poor in lubricating properties. On the other hand, the foregoing aromatic ester oil such as a trimellitic acid ester oil and pyromellitic acid ester oil has excellent characteristics in heat resistance, oxidation resistance and wear resistance. In particular, since the aromatic ester oil represented by the foregoing general formula (XV) or (XVI) is low in a pour point and high in a viscosity index, it is suitably used for rolling bearings for automotive electrical equipment auxiliary device, requiring a use environment of from a very low temperature to a high temperature. The aromatic ester oil is inexpensive and easily available.

As such a trimellitic acid ester, "TRIMEX T-08" and "TRIMEX N-08", all of which are manufactured by Kao Corporation; "ADEKA PROVER T-45", "ADEKA PROVER T-90" and "ADEKA PROVER PT-50", all of which are manufactured by Denka Corporation; "UNIQEMA EMKARATE 8130", "UNIQEMA EMKARATE 9130" and "UNIQEMA EMKARATE 1320"; and the like are available from the market. Moreover, as the pyromellitic acid ester, "ADEKA PROVER T-45", "ADEKA PROVER LX-1891" and "ADEKA PROVER LX-1892", all of which are manufactured by Denka Corporation; "BISOLUBETOPM", manufactured by Cognis; and the like are available from the market. These are low in a pour point and can be suitably used in the invention.

Diphenyl ether oils represented by following formulae are also preferable. By using such a diphenyl ether oil, it is possible to prepare a lubricant composition having excellent heat resistance and durability (for example, excellent lubricating properties can be kept over a long period of time even at a high temperature exceeding 160° C.). In particular, it can be suitably used in a site to be used at a high temperature and a high speed, such as components of automotive electrical equipment, automotive engine auxiliary devices, etc.

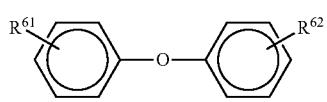

(XVII)

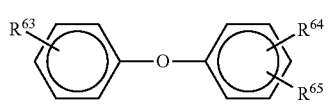

(XVIII)

In the foregoing formulae, $R^{61}$ and $R^{62}$ may be the same as or different from each other and each represents a linear or branched perfluoroalkyl group or a partial substitute thereof. The partial substitute of a perfluoroalkyl group as referred to herein means those in which a part of fluorine atoms or hydrogen atoms is substituted with a substituent such as a halogen atom such as a chlorine atom, a bromine atom, an iodine atom, etc., a hydroxyl group, a thiol group, an alkoxy group, an ether group, an amino group, a nitrile group, a nitro group, a sulfonyl group, a sulfinyl group, or a carbonyl-containing group such as an ester group, an amino group, an acyl group, an amide group, a carboxyl group, etc.; or the like, or having an ether structure in a part of the principal chain thereof.

Moreover, the carbon atom number in each of $R^{61}$ and $R^{62}$ is from 1 to 25, preferably from 1 to 10, and more preferably from 1 to 3. When the carbon atom number is more than 25, availability or synthesis of the raw material becomes difficult.

In addition, a (fluorine atom number)/(carbon atom number) ratio in each of $R^{61}$ and $R^{62}$ is from 0.6 to 3, preferably 1 to 3, and more preferably from 1.5 to 3.

In the foregoing formulae, one of $R^{63}$, $R^{64}$ and $R^{65}$ represents a hydrogen atom, and the remaining two represent the same or different branched alkyl group. Moreover, the carbon atom number is from 10 to 26, and preferably from 12 to 24. When the carbon atom number is less than 10, the amount of evaporation becomes large, whereas when it is more than 26, the fluidity at a low temperature is poor, resulting in a problem in the use. Specific examples thereof include a decyl group, an undecyl group, a dodecyl group, a tridecyl group, a tetradecyl group, a pentadecyl group, a hexadecyl group, a heptadecyl group, an octadecyl group, a nanodecyl group, an eicosyl group, etc. These may be branched.

The diphenyl ether oil represented by any of the foregoing formulae may be utilized in an amount of from 50 to 100% by mass and may be utilized in an amount of from 60 to 80% by mass in the oily medium. Within the foregoing range, the heat resistance is more improved. As an oil which is used jointly with the diphenyl ether oil, an ester based synthetic oil and a poly-α-olefin oil are preferable.

A material which is utilized as a base oil for traction oil can be utilized as the oily medium. The base oil for traction oil is usually selected among hydrocarbons. Hydrocarbons having a cyclic structure such as a cyclohexane ring, a decalin ring, a bicycloheptane ring, a bicyclooctane ring, etc. in a molecule thereof are preferable (see JP-A-2000-109871).

For example, examples of a saturated hydrocarbon compound having a cyclohexane ring include compounds disclosed in JP-B-3-80191, JP-B-2-52958, JP-B-6-39419, JP-B-6-92323, etc.; examples of a saturated hydrocarbon compound having a decalin ring include compounds disclosed in JP-B-60-43392 and JP-B-6-51874; and examples of a saturated hydrocarbon compound having a bicycloheptane ring include compounds disclosed in JP-B-5-31914, JP-B-7-103387, etc. More specifically, there are included 1-(1-decalyl)-2-cyclohexylpropane, 1-cyclohexyl-1-decalylethane, 1,3-dicyclohexyl-3-methylbutane, 2,4-dicyclohexylpentane; 1,2-bis(methylcyclohexyl)-2-methylpropane, 1,1-bis(methylcyclohexyl)-2-methylpropane and 2,4-dicyclohexyl-2-methylpentane. Moreover, examples of a saturated hydrocarbon compound having a bicyclooctane ring include compounds disclosed in JP-A-5-9134, etc.

An ionic liquid (ion liquid) has properties such as flame retardancy, nonvolatility, high polarity, high ion conductivity, high heat resistance, etc. In view of such properties, the ionic liquid is expected to be applied as a reaction solvent for green chemistry which is environmentally friendly or a next-generation electrolyte which is safe and high in performances. In the invention, the subject ionic liquid can be utilized as the oily medium. The ionic liquid (ion liquid) includes various kinds, and examples thereof include quaternary salts of a nitrogen-containing heterocyclic compound such as ammonium salts, choline salts, phosphoric acid salts, pyrazoline salts, pyrrolidine salts, imidazolium salts, pyridine salts, etc., sulfonium salts and the like.

As the oily medium which is used in the invention, petroleum hydrocarbons which are in general useful for the use as a fuel, for example, gasoline in the case of an internal combustion engine, etc. can be used. Such a fuel is typically a mixture of various kinds of hydrocarbons, and examples of components thereof include linear or branched paraffins and olefins, aromatic or naphthene based hydrocarbons and other liquid hydrocarbon based materials which are suitable for the use in a spark ignition gasoline engine.

Such a composition is supplied as every grade, for example, unleaded gasoline, leaded gasoline, etc., and typically, it is derived from a petroleum crude oil utilizing usual refining method and blending method, for example, straight fractional distillation, thermal cracking, hydrocracking, catalytic cracking and various modification methods. Gasoline will be defined as a liquid hydrocarbon or a mixture of hydrocarbon/oxygenate having an initial boiling point in the range of from about 20 to 60° C. and a final boiling point in the range of from about 150 to 230° C. when measured by the distillation method of ASTM D86. Examples of this oxygenate include alcohols such as methanol, ethanol, isopropanol, t-butanol, a $C_1$ to $C_5$ mixed alcohol, etc.; ethers such as methyl t-butyl ether, t-amyl ethyl ether, ethyl t-butyl ether, a mixed ether, etc.; and ketones such as acetone, etc.

In the invention, the above-exemplified oils may be used singly or in admixture of two or more different kinds thereof as the oily medium.

Moreover, there may be the case where the mineral oil is insufficient in wettability against a resin-made member, and from the viewpoint of lubricating properties or low friction properties against a resin-made member, or the like, it is preferable to use other oils than the mineral oil as the oily medium. Specifically, a polyolefin oil, a silicone oil, an ester oil, a polyglycol oil and a polyphenyl ether oil are preferable.

Moreover, there may be the case where the ester oil adversely influences a resin-made member or a rubber-made member, and from the viewpoint of preventing adverse influences against a resin-made member or a rubber-made member, it is preferable to use other oil than the ester oil. Specifically, a mineral oil, a polyolefin oil, a silicone oil, a polyglycol oil and a polyphenyl ether oil are preferable.

From the both viewpoints, polyolefins are preferable. Of these, a copolymer of ethylene and propylene; a copolymer of ethylene and an α-olefin having from 5 to 12 carbon atoms; and polybutene, polyisobutene or a polymer of an α-olefin having from 5 to 12 carbon atoms are more preferable, with a copolymer of ethylene and an α-olefin having from 5 to 12 carbon atoms and a polymer of an α-olefin having from 5 to 12 carbon atoms being further preferable.

3. Preparation Method of the Composition of the Invention:

The composition of the invention can be prepared by adding the compound represented by the foregoing formula (Z) into an oily medium and dissolving and/or dispersing it therein. The dissolution and/or dispersion may be carried out under heating. An addition amount of the compound represented by the foregoing formula (Z) is preferably from about 0.1 to 10% by mass relative to the mass of the oily medium. But, it should not be construed that the addition amount of the compound represented by the foregoing formula (Z) is limited to this range. So far as the addition amount is sufficient so that the foregoing compound exhibits a friction reducing effect, as a matter of course, a range other than the foregoing range may be applied.

An embodiment of the composition of the invention is a composition containing an oily medium composed of at least one member selected among a mineral oil, a poly-α-olefin, a synthetic ester oil, a diphenyl ether oil, a fluorocarbon oil and a silicone oil and containing less than 3% by mass of the compound represented by the formula (Z).

The composition of the invention may contain at least one additive together with the compound of the foregoing formula (Z) and the oily medium within the range where the effect of the invention is not impaired. Examples of the additive include a dispersant, a cleaning agent, an antioxidant, a carrier fluid, a metal deactivator, a dye, a marker, a corrosion inhibitor, a biocide, an antistatic additive, a drag reducer, a demulsifier, an emulsifier, an anti-fogging agent, a deicer additive, an antiknock additive, an anti-valve seat recession additive, a lubricating additive, a surfactant and a combustion improver. Moreover, a lubricant, various additives used for, for example, a bearing oil, a gear oil, a power transmission oil, etc., namely a wear-resistant agent, a viscosity index improver, a cleaning dispersant, a metal deactivator, a corrosion inhibitor, an antifoaming agent, etc., can be properly added within the rang where the object of the invention is not impaired. Such a material may be at least one member selected among an organic zinc compound, a molybdenum compound, an organic phosphorus compound and an organic sulfur compound, and the addition of such a compound is preferable from the standpoints of addition of a function of anti-oxidation ability by the organic zinc compound and wear inhibition under a true boundary lubrication condition by the latter three.

Regarding some of the additives, specific examples will be described in details below.

Antiwear Agents:

Internal combustion engine lubricating oils require the presence of antiwear and/or extreme pressure (EP) additives in order to provide adequate antiwear protection for the engine. Increasingly demanding specifications for engine oil performance have required increasing antiwear properties of the oil. Antiwear and EP additives perform this role by reducing friction and wear of metal parts. While there are many different types of antiwear additives, for several decades the principal antiwear additive for internal combustion engine crankcase oils has been a metal alkylthiophosphate and more particularly a metal dialkyldithiophosphate in which the primary metal constituent is zinc, or zinc dialkyldithiophosphate (ZDDP). Typical examples of ZDDP compound include the compounds represented by the formula of $Zn[SP(S)(OR^{71})(OR^{72})]_2$ ($R^{71}$ and $R^{72}$ are $C_1$-$C_{18}$ alkyl groups, preferably $C_2$-$C_{12}$ alkyl groups). These alkyl groups may be straight chain or branched, and derived from primary and/or secondary alcohols and/or alkaryl groups such as alkyl phenol. The ZDDP generally is used in amounts of from about 0.4 to 1.4% by mass of the total composition, although the amount is not limited to the range.

However, it has been found that the phosphorus from these additives has a harmful effect on the catalyst in catalytic converters and also on oxygen sensors in automobiles. One example of the way for minimizing this effect is to replace some or all of the ZDDP with phosphorus-free antiwear additives. Accordingly, various non-phosphorous additives can be also used as antiwear agent. Sulfurized olefins are useful as antiwear or EP additives. Sulfur-containing olefins can be prepared by sulfurization of various organic materials such as aliphatic, arylaliphatic and alicyclic olefin hydrocarbons containing from about 3 to 30 carbon atoms, preferably from about 3 20 carbon atoms. The olefinic compounds contain at least one non-aromatic double bond. Such compounds are represented by the formula:

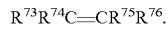

$R^{73}R^{74}C=CR^{75}R^{76}$.

In the formula, $R^{73}$-$R^{76}$ each independently represent a hydrogen or a hydrocarbon group. Preferred hydrocarbon group is n alkyl or alkenyl group. Any two of $R^{73}$-$R^{76}$ may be connected so as to form a cyclic ring. Additional information concerning sulfurized olefins and their preparation can be found in U.S. Pat. No. 4,941,984, which can be referred.

The use of polysulfides of thiophosphorous acids and thiophosphorous acid esters as lubricant additives is disclosed in U.S. Pat. Nos. 2,443,264; 2,471,115; 2,526,497; and 2,591, 577. Addition of phosphorothionyl disulfides as an antiwear, antioxidant, and EP additive is disclosed in U.S. Pat. No. 3,770,854. Use of alkylthiocarbamoyl compounds (bis(dibutyl)thiocarbamoyl, for example) in combination with a molybdenum compound (oxymolybdenum diisopropylphosphorodithioate sulfide, for example) and a phosphorous ester (dibutyl hydrogen phosphite, for example) as antiwear additives in lubricants is disclosed in U.S. Pat. No. 4,501,678. U.S. Pat. No. 4,758,362 discloses use of a carbamate additive to provide improved antiwear and extreme pressure properties. The use of thiocarbamate as an antiwear additive is disclosed in U.S. Pat. No. 5,693,598. Thiocarbamate/molybdenum complexes such as moly-sulfur alkyl dithiocarbamate trimer complex ($R=C_8$-$C_{12}$ alkyl) are also useful antiwear agents.

Glycerol esters may be used as antiwear agents. For example, mono-, di, and tri-oleates, mono-palmitates and mono-myristates may be used.

ZDDP may be combined with other antiwear agent(s). U.S. Pat. No. 5,034,141 discloses that a combination of a thiodixanthogen compound (such as octylthiodixanthogen) and a metal thiophosphate (such as ZDDP) can improve antiwear properties. U.S. Pat. No. 5,034,142 discloses that use of a metal alkyoxyalkylxanthate (such as nickel ethoxyethylxanthate) and a dixanthogen (such as diethoxyethyl dixanthogen) in combination with ZDDP improves antiwear properties.

Preferred antiwear additives include phosphorus and sulfur compounds such as zinc nd sulfur compounds such as zinc dithiophosphates and/or sulfur, nitrogen, boron, molybdenum phosphorodithioates, molybdenum dithiocarbamates and various organo-molybdenum derivatives including heterocyclics (for example, dimercaptothiadiazoles, mercaptobenzothiadiazoles, triazines, and the like), alicyclics, amines, alcohols, esters, diols, triols, fatty amides and the like can also be used. Such additive may be used in amounts ranging from about 0.01 to 6% by mass, preferably about 0.01 to 4% by mass.

Viscosity Index Improver:

Viscosity index improvers (also known as VI improvers, viscosity modifiers, and viscosity improvers) provide lubricants with high and low-temperature operability. These additives impart favorable viscosity index number enhancement and shear stability at elevated temperatures and acceptable viscosity at low temperatures. Appropriate examples of the viscosity index improver include high-molecular weight hydrocarbons, polyesters, and viscosity index improvers capable of functioning not only as a viscosity index improver but also as a dispersant. The molecular weight of such a polymer is typically from about 10,000 to about 1,000,000, more typically from about 20,000 to about 500,000, and even more typically from about 50,000 to about 200,000.

Appropriate examples of the viscosity index improver include polymers and copolymers of methacrylate, butadiene, olefin or alkylated styrene. Polyisobutylenes are the typical viscosity index improvers. Other typical examples are polymethacrylates (for example, copolymers of any length alkyl methacrylate); and some of them function as a pour point depressant. Other typical examples are copolymers of ethylene and propylene, hydrogenated block-copolymers of styrene and isoprene, and polyacrylates (for example, copolymers of any length alkyl acrylate). Specific examples of them include styrene-butadiene polymers and styrene-isoprene polymers having a molecular-weight of from about 50,000 to about 200,000.

The viscosity index improver may be used in amounts ranging from about 0.01 to 8% by mass, preferably about 0.01 to 4% by mass.

Antioxidants:

Antioxidants have a function of retarding the oxidative degradation of oil(s) used in along with them. Such degradation may result in deposits on metal surfaces, the presence of sludge, or a viscosity increase in the lubricant. Various antioxidants which are useful in lubricant oil compositions are described, for example, "Klamann in Lubricants and Related Products" (Verlag Chemie (Deerfield Beach, Fla.), ISBN0-89573-177-0), and U.S. Pat. Nos. 4,798,684 and 5,084,197, which can be referred.

Useful antioxidants include hindered phenols. These phenolic antioxidants may be ashless (metal-free) phenolic compounds or neutral or basic metal salts of certain phenolic compounds. Typical phenolic antioxidants are hindered phenolics that contain a sterically hindered hydroxyl group, and these include those derivatives of dihydroxy aryl compounds in which the hydroxyl groups are in the o- or p-position to each other. Examples of the typical phenolic antioxidant include hindered phenols substituted with about $C_6$+alkyl groups and alkylene coupled derivatives of such hindered phenols. Examples of phenolic materials of this type include 2-t-butyl-4-heptyl phenol; 2-t-butyl-4-octyl phenol; 2-t-butyl-4-dodecyl phenol; 2,6-di-t-butyl-4-heptyl phenol; 2,6-di-t-butyl-4-dodecyl phenol; 2-methyl-6-t-butyl-4-heptyl phenol; and 2-methyl-6-t-butyl-4-dodecyl phenol. Other useful mono-phenolic antioxidants may include, for example, 2,6-di-alkyl-phenolic proprionic ester derivatives. Bis-phenolic antioxidants may also be advantageously used in combination with the invention. Examples of ortho coupled phenols include: 2,2'-bis(6-t-butyl-4-heptyl phenol); 2,2'-bis(6-t-butyl-4-octyl phenol); and 2,2'-bis(6-t-butyl-4-dodecyl phenol). Para coupled bis phenols include, for example, 4,4'-bis(2,6-di-t-butyl phenol) and 4,4'-methylene-bis(2,6-di-t-butyl phenol).

Non-phenolic oxidation inhibitors which may be used include aromatic amine antioxidants and these may be used either as such or in combination with phenolics. Typical examples of non-phenolic antioxidants include alkylated and non-alkylated aromatic amines such as aromatic monoamines represented by formula of $R^{78}R^{79}R^{80}N$ {in the formula, $R^{78}$ represents an aliphatic, aromatic or substituted aromatic group; $R^{79}$ represents an aromatic or a substituted aromatic group; and $R^{80}$ represents H, alkyl, aryl or $R^{81}S(O)_xR^{82}$ (where $R^{81}$ represents an alkylene, alkenylene, or aralkylene group, $R^{82}$ represents a higher alkyl group, or an alkenyl, aryl, or alkaryl group, and x is 0, 1 or 2)}. The aliphatic group $R^{78}$ may contain from 1 to about 20 carbon atoms, and preferably contains from about 6 to 12 carbon atoms. The aliphatic group means a saturated aliphatic group. Preferably, both $R^{78}$ and $R^{79}$ are aromatic or substituted aromatic groups, and the aromatic group may be a condensed ring aromatic group such as naphthyl. Aromatic groups $R^{78}$ and $R^{79}$ may be joined together with other groups such as S.

Typical aromatic amines antioxidants may have alkyl substituent groups having at least about 6 carbon atoms. Examples of aliphatic groups include hexyl, heptyl, octyl, nonyl, and decyl. Generally, the aliphatic groups will not contain more than about 14 carbon atoms. The general types of amine antioxidants useful in the present compositions include diphenylamines, phenyl naphthyl-amines, phenothiazines, imidodibenzyls and diphenyl phenylene diamines. Mixtures of two or more aromatic amines are also useful. Polymeric amine antioxidants may also be used. Specific examples of aromatic amine antioxidants useful in the present invention include: p,p'-dioctyldiphenylamine; t-octylphenyl-alpha-naphthylamine; phenyl-alphanaphthylamine; and p-octylphenyl-alpha-naphthylamine.

Sulfurized alkyl phenols and alkali or alkaline earth metal salts thereof also are useful antioxidants. Low sulfur peroxide decomposers are useful as antioxidants.

Another class of antioxidant to be used in the composition of the invention is oil-soluble copper compounds. Any oil-soluble suitable copper compound may be blended into the lubricating oil. Examples of suitable copper antioxidants include copper dihydrocarbyl thio or dithio-phosphates and copper salts of carboxylic acid (naturally occurring or synthetic). Other suitable copper salts include copper dithiacarbamates, sulphonates, phenates, and acetylacetonates. Basic, neutral, or acidic copper Cu(I) and/or Cu(II) salts derived from alkenyl succinic acids or anhydrides are know to be particularly useful.

Preferable examples of the antioxidant include hindered phenols, arylamines, low sulfur peroxide decomposers and other related components. These antioxidants may be used individually by type or in combination with one another. Such additives may be used in amounts of from about 0.01 to 5% by mass, preferably from about 0.01 to 2% by mass, even more preferably from about 0.01 to 1% by mass.

Cleaning Agents:

Cleaning agents are commonly used in lubricant oil compositions. A typical cleaning agent is an anionic material containing a long chain lipophilic portion of the molecule and a smaller anionic or lipophobic portion of the molecule. The anionic portion of the cleaning agent is typically derived from an organic acid such as a sulfur acid, carboxylic acid, phosphorous acid, phenol, or mixtures thereof. The counter ion is typically an alkaline earth or alkali metal.

Salts that contain a substantially stoichiometric amount of the metal are described as neutral salts and have a total base number (TBN, as measured by ASTM D2896) of from 0 to 80. Many compositions are overbased, containing large amounts of a metal base that is achieved by reacting an excess of a metal compound (a metal hydroxide or oxide, for example) with an acidic gas (such as carbon dioxide). Useful cleaning agents can be neutral, mildly overbased, or highly overbased.

It is generally desirable for at least some parts of the cleaning agent to be overbased. Overbased cleaning agents help neutralize acidic impurities produced by the combustion process and become entrapped in the oil. Typically, the overbased material has a ratio of metallic ion to anionic portion of the cleaning agent of about 1.05:1 to 50:1 on an equivalent basis. More preferably, the ratio is from about 4:1 to about 25:1. The resulting cleaning agent is an overbased cleaning agent that will typically have a TBN of about 150 or higher, often about 250 to 450 or more. Preferably, the overbasing cation is sodium, calcium, or magnesium. A mixture of cleaning agents of differing TBN can be used in the present invention.

Preferable examples of the cleaning agent include the alkali or alkaline earth metal salts of sulfates, phenates, carboxylates, phosphates, and salicylates.

Sulfonates may be prepared from sulfonic acids that are typically obtained by sulfonation of alkyl substituted aromatic hydrocarbons. Examples of hydrocarbon include those obtained by alkylating benzene, toluene, xylene, naphthalene, biphenyl and their halogenated derivatives (chlorobenzene, chlorotoluene, and chloronaphthalene, for example). The alkylating agents typically have about 3 to 70 carbon atoms. The alkaryl sulfonates typically contain about 9 to about 80 carbon or more carbon atoms, more typically from about 16 to 60 carbon atoms.

Various overbased Metal salts of various sulfonic acids which are useful as cleaning agents/dispersants in lubricant oils are disclosed. Various overbased sulfonates which are useful as cleaning agents/detergents are disclosed. They may be used in the invention.

Alkaline earth phenates are another useful class of cleaning agent. These cleaning agents may be prepared by reacting alkaline earth metal hydroxide or oxide (such as CaO, $Ca(OH)_2$, BaO, $Ba(OH)_2$, MgO, and $Mg(OH)_2$) with an alkyl phenol or sulfurized alkylphenol. Useful alkyl groups include straight chain or branched about $C_1$-$C_{30}$ alkyl groups, preferably about $C_4$-$C_{20}$ alkyl groups. Examples of suitable phenols include isobutylphenol, 2-ethylhexylphenol, nonylphenol, 1-ethyldecylphenol, and the like. It should be noted that starting material of alkylphenols may contain more than one alkyl substituent that are each independently straight chain or branched. When a non-sulfurized alkylphenol is used, the sulfurized product may be obtained by methods well known in the art. These methods include heating a mixture of alkylphenol and sulfurizing agent, including elemental sulfur or sulfur halides, such as sulfur dichloride and the like, and then reacting the sulfurized phenol with an alkaline earth metal base.

Metal salts of carboxylic acids are also useful as cleaning agents. These carboxylic acid cleaning agents may be prepared by reacting a basic metal compound with at least one carboxylic acid and removing free water from the reaction product. These compounds may be overbased to produce the desired TBN level. Cleaning agents made from salicylic acid are one preferred class of cleaning agents derived from carboxylic acids. Examples of the useful salicylate include long chain alkyl salicylates. One useful family of compositions is of the following formula.

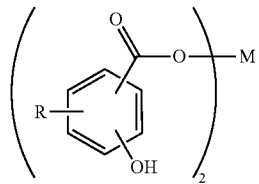

In the formula, R represents a hydrogen atom or an alkyl group having 1 to about 30 carbon atoms, n is an integer from 1 to 4, and M is an alkaline earth metal. Preferably, R is a $C_{11}$ or longer alkyl chain, and more preferably $C_{13}$ or longer alkyl chain. R may be an optionally substituted with substituents that do not interfere with the cleaning-agent's function. M is preferably, calcium, magnesium, or barium, and more preferably, calcium or magnesium. More preferably, M is calcium.

Hydrocarbyl-substituted salicylic acids may be prepared from phenols by the Kolbe reaction. See U.S. Pat. No. 3,595, 791, incorporated herein by reference in its entirety, for additional information on synthesis of these compounds. The metal salts of the hydrocarbyl-substituted salicylic acids may be prepared by double decomposition of a metal salt in a polar solvent such as water or alcohol.

Alkaline earth metal phosphates are also used as cleaning agents.

Detergents may be simple cleaning agents or what is known as hybrid or complex cleaning agents. The latter cleaning agents can provide the properties of two cleaning agents without the need to blend separate materials. See, for example, U.S. Pat. No. 6,034,039, which can be referred.

Preferable examples of the cleaning agent include calcium phenates, calcium sulfonates, calcium salicylates, magnesium phenates, magnesium sulfonates, magnesium salicylates and other related components (including borated cleaning agents). Typically the total cleaning agent concentration is from about 0.01 to 6% by mass, preferably from about 0.1 to 3% by mass, even more preferably from about 0.01 to 0.5% by mass.

Dispersants:

During engine operation, oil insoluble oxidation byproducts are produced. Dispersants help keep these byproducts in solution, thus diminishing their deposit on metal surfaces. Dispersants may be ashless or ash-forming in nature. Preferably, the dispersant is ashless. So called ashless dispersants are organic materials that form substantially no ash upon combustion. For example, non-metal-containing or borated metal-free dispersants are considered ashless. In contrast, metal-containing cleaning agents discussed above form ash upon combustion.

Suitable dispersants typically contain a polar group attached to a relatively high molecular weight hydrocarbon chain. The polar group typically contains at least one element of nitrogen, oxygen, or phosphorous. Typical hydrocarbon chains contain about 50 to 400 carbon atoms.

Examples of the dispersant include phenates, sulfonates, sulfurized phenates, salicylates, naphthenates, stearates, carbamates, thiocarbamates, and phosphorus derivatives. Particularly useful examples of the dispersant include alkenyl-succinic derivatives, typically produced by the reaction of a long chain substituted alkenyl succinic compound, usually a substituted succinic anhydride, with a polyhydroxy or polyamino compound. The long chain group constituting the lipophilic portion of the molecule which adds solubility in the oil, is normally a polyisobutylene group. Many examples of this type of dispersant are well known commercially or in various documents. Exemplary U.S. Patents describing such dispersants include U.S. Pat. Nos. 3,172,892; 3,2145,707; 3,219,666; 3,316,177; 3,341,542; 3,444,170; 3,454,607; 3,541,012; 3,630,904; 3,632,511; 3,787,374 and 4,234,435. Other types of dispersants are described in U.S. Pat. Nos. 3,036,003; 3,200,107; 3,254,025; 3,275,554; 3,438,757; 3,454,555; 3,565,804; 3,413,347; 3,697,574; 3,725,277; 3,725,480; 3,726,882; 4,454,059; 3,329,658; 3,449,250; 3,519,565; 3,666,730; 3,687,849; 3,702,300; 4,100,082; 5,705,458. A further description of dispersants is also found in European Patent Application No. 471 071.

Hydrocarbyl-substituted succinic acid compounds are well known dispersants. In particular, succinimide, succinate esters, or succinate ester amides prepared by the reaction of hydrocarbon-substituted succinic acid preferably having at least 50 carbon atoms in the hydrocarbon substituent, with at least one equivalent of an alkylene amine, are particularly useful.

Succinimides are formed by the condensation reaction between alkenyl succinic anhydrides and amines. Molar ratios can vary depending on the polyamine. For example, the molar ratio of alkenyl succinic anhydride to TEPA can vary from about 1:1 to about 5:1. Representative examples are shown in U.S. Pat. Nos. 3,087,936; 3,172,892; 3,219,666; 3,272,746; 3,322,670; 3,652,616; 3,948,800; and Canada Pat. No. 1,094,044.

Succinate esters are formed by the condensation reaction between alkenyl succinic anhydrides and alcohols or polyols. Molar ratios can vary depending on the alcohol or polyol used. For example, the condensation product of an alkenyl succinic anhydride and pentaerythritol is a useful dispersant.

Succinate ester amides are formed by condensation reaction between alkenyl succinic anhydrides and alkanol amines. For example, suitable alkanol amines include ethoxylated polyalkylpolyamines, propoxylated polyalkylpolyamines and polyalkenylpolyamines such as polyethylene polyamines. One example is propoxylated hexamethylenediamine. Representative examples are shown in U.S. Pat. No. 4,426,305.

The molecular weight of the alkenyl succinic anhydrides used in the preceding paragraphs will range between about 800 and 2,500. The above products can be post-reacted with various reagents such as sulfur, oxygen, formaldehyde, carboxylic acids such as oleic acid, and boron compounds such as borate esters or highly borated dispersants. The dispersants can be borated with from about 0.1 to about 5 moles of boron per mole of dispersant reaction product, including those derived from mono-succinimides, bis-succinimides (also known as disuccinimides), and mixtures thereof.

Mannich base dispersants are made from the reaction of alkylphenols, formaldehyde, and amines. See U.S. Pat. No. 4,767,551, incorporated by reference herein in its entirety. Process aids and catalysts, such as oleic acid and sulfonic acids, can also be part of the reaction mixture. Molecular weights of the alkylphenols range from 800 to 2,500. Representative examples are shown in U.S. Pat. Nos. 3,697,574; 3,703,536; 3,704,308; 3,751,365; 3,756,953; 3,798,165; and 3,803,039.

Typical high molecular weight aliphatic acid modified Mannich condensation products useful in this invention can be prepared from high molecular weight alkyl-substituted hydroxyaromatics or $HN(R)_2$ group-containing reactants.

Examples of high molecular weight alkyl-substituted hydroxyaromatic compounds are polypropylphenol, polybutylphenol, and other polyalkylphenols. These polyalkylphenols can be obtained by the alkylation, in the presence of an alkylating catalyst, such as $BF_3$, of phenol with high molecular weight polypropylene, polybutylene, and other polyalkylene compounds to give alkyl substituents on the benzene ring of phenol having an average 600-100,000 molecular weight.

Examples of $HN(R)_2$ group-containing reactants are alkylene polyamines, principally polyethylene polyamines. Other representative organic compounds containing at least one $HN(R)_2$ group suitable for use in the preparation of Mannich condensation products are well known and include mono- and di-amino alkanes and their substituted analogs, e.g., ethylamine and diethanol amine; aromatic diamines, e.g., phenylene diamine, diamino naphthalenes; heterocyclic amines, e.g., morpholine, pyrrole, pyrrolidine, imidazole, imidazolidine, and piperidine; melamine and their substituted analogs.

Examples of alkylene polyamide reactants include ethylenediamine, diethylene triamine, triethylene tetraamine, tetraethylene pentaamine, pentaethylene hexamine, hexaethylene heptaamine, heptaethylene octaamine, octaethylene nonaamine, nonaethylene decamine, decaethylene undecamine, and mixtures of such amines. Some preferred compositions correspond to formula $H_2N-(Z-NH-)_nH$, where Z is a divalent ethylene and n is 1 to 10 of the foregoing formula. Corresponding propylene polyamines such as propylene diamine and di-, tri-, tetra-, pentapropylene tri-, tetra-, penta- and hexaamines are also suitable reactants. Alkylene polyamines usually are obtained by the reaction of ammonia and dihalo alkanes, such as dichloro alkanes. Thus, the alkylene polyamines obtained from the reaction of 2 to 11 moles of ammonia with 1 to 10 moles of dichloro alkanes having 2 to 6 carbon atoms and the chlorines on different carbons are suitable alkylene polyamine reactants.

Aldehyde reactants useful in the preparation of the high molecular products useful in this invention include aliphatic aldehydes such as formaldehyde (such as paraformaldehyde and formalin), acetaldehyde and aldol (b-hydroxybutyraldehyde, for example). Formaldehyde or a formaldehyde-yielding reactant is preferred.

Hydrocarbyl substituted amine ashless dispersant additives are well known to those skilled in the art. See, for example, U.S. Pat. Nos. 3,275,554; 3,438,757; 3,565,804; 3,755,433, 3,822,209, and 5,084,197, which can be referred.

Preferable examples of the dispersant include borated and non-borated succinimides, including those derivatives from mono-succinimides, bis-succinimides, and/or mixtures of mono- and bis-succinimides, wherein the hydrocarbyl succinimide is derived from a hydrocarbylene group such as polyisobutylene having a Mn of from about 500 to about 5000, preferably from about 1000 to about 3000, more preferably from about 1000 to about 2000, even more preferably from about 1000 to about 1600, or a mixture of such hydrocarbylene groups. Other preferable examples of the dispersant include succinic acid-esters and amides, alkylphenol-polyamine coupled Mannich adducts, their capped derivatives, and other related components. Such additives may be used in an amount of about 0.1 to 20% by mass, preferably about 0.1 to 8% by mass.

Pour Point Depressants:

Pour point depressants have a function of lowering the minimum temperature at which the fluid will flow or can be poured. Examples of the suitable pour point depressant include polymethacrylates, polyacrylates, polyarylamides, condensation products of haloparaffin waxes and aromatic compounds, vinyl carboxylate polymers, and terpolymers of dialkylfumarates, vinyl esters of fatty acids and allyl vinyl ethers. U.S. Pat. Nos. 1,815,022; 2,015,748; 2,191,498; 2,387,501; 2,655,479; 2,666,746; 2,721,877; 2,721,878; and 3,250,715 describe useful pour point depressants and/or the preparation thereof. Such additives may be used in an amount of about 0.01 to 5% by mass, preferably about 0.01 to 1.5% by mass.

Corrosion Inhibitors:

Corrosion inhibitors are used to reduce the degradation of metallic parts to contact with the lubricating oil composition. Examples of the suitable corrosion inhibitor include thiadiazoles. See, for example, U.S. Pat. Nos. 2,719,125; 2,719,126; and 3,087,932, which can be referred. Such additives may be used in an amount of about 0.01 to 5% by mass, preferably about 0.01 to 1.5% by mass.

Seal Compatibility Additives:

Seal compatibility agents help to swell elastomeric seals by bringing about chemical reactions in fluids or physical changes in elastomers. Examples of the suitable seal compatibility agent include organic phosphates, aromatic esters, aromatic hydrocarbons, esters (such as butylbenzyl phthalate), and polybutenyl succinic anhydride. Such additives may be used in an amount of about 0.01 to 3% by mass, preferably about 0.01 to 2% by mass.

Anti-Foam Agents:

Anti-foam agents retard the formation of stable foams. Silicones and organic polymers are typical anti-foam agents. For example, polysiloxanes, such as silicon oil or polydimethyl siloxane, provide antifoam properties. Anti-foam agents are commercially available and may be used in conventional minor amounts along with other additives such as demulsifiers; usually the amount of these additives combined is less than 1 percent and often less than 0.1 percent.

Antirust Additives (or Corrosion Inhibitors):

Antirust additives (or corrosion inhibitors) are additives that protect lubricated metal surfaces against chemical attack by water or other contaminants. Various antirust additives are commercially available; they are referred to also in Klamann in "Lubricants and Related Products" (Verlag Chemie (Deerfield Beach, Fla.), ISBN0-89573-177-0).

One type of antirust additive is a polar compound that wets the metal surface preferentially, protecting it with a film of oil. Another type of antirust additive absorbs water by incorporating it in a water-in-oil emulsion so that only the oil touches the metal surface. Yet another type of antirust additive chemically adheres to the metal to produce a non-reactive surface. Examples of suitable additives include zinc dithiophosphates, metal phenolates, basic metal sulfonates, fatty acids and amines. Such additives may be used in an amount of about 0.01 to 5% by mass, preferably about 0.01 to 1.5% by mass.

Friction Modifiers:

A friction modifier is any material or materials that can alter the coefficient of friction of any lubricant or fluid containing such material(s). Friction modifiers, also known as friction reducers, or lubricity agents or oiliness agents, and other such agents that change the coefficient of friction of lubricant base oils, formulated lubricant compositions, or functional fluids, may be effectively used in combination with the base oils or lubricant compositions of the present invention if desired. Friction modifiers that lower the coefficient of friction are particularly advantageous in combination with the base oils and lube compositions of this invention. Friction modifiers may include metal-containing compounds or materials as well as ashless compounds or materials, or mixtures thereof. Metal-containing friction modifiers may include metal salts or metal-ligand complexes where the metals may include alkali, alkaline earth, or transition group metals. Such metal-containing friction modifiers may also have low-ash characteristics. Transition metals may include Mo, Sb, Sn, Fe, Cu, Zn, and others. Ligands may include hydrocarbyl derivative of alcohols, polyols, glycerols, partial ester glycerols, thiols, carboxylates, carbamates, thiocarbamates, dithiocarbamates, phosphates, thiophosphates, dithiophosphates, amides, imides, amines, thiazoles, thiadiazoles, dithiazoles, diazoles, triazoles, and other polar molecular functional groups containing effective amounts of O, N, S, or P, individually or in combination. In particular, Mo-containing compounds can be particularly effective such as for example Mo-dithiocarbamates (Mo(DTC)), Mo-dithiophosphates (Mo(DTP)), Mo-amines (Mo(Am)), Mo-alcoholates, Mo-alcohol-amides, etc.

Ashless friction modifiers may have also include lubricant materials that contain effective amounts of polar groups, for example hydroxyl-containing hydrocarbyl base oils, glycerides, partial glycerides, glyceride derivatives, and the like. Polar groups in friction modifiers may include hydrocarbyl groups containing effective amounts of O, N, S, or P, individually or in combination. Other friction modifiers that may be particularly effective include, for example, salts (both ash-containing and ashless derivatives) of fatty acids, fatty alcohols, fatty amides, fatty esters, hydroxyl-containing carboxylates, and comparable synthetic long-chain hydrocarbyl acids, alcohols, amides, esters, hydroxy carboxylates, and the like. In some instances fatty organic acids, fatty amines, and sulfurized fatty acids may be used as suitable friction modifiers.

Useful concentrations of friction modifiers may range from about 0.01% by mass to 15% by mass, often with a preferred range of about 0.1% by mass to 5% by mass. Concentrations of molybdenum containing materials are often described in terms of Mo metal concentration. Advantageous concentrations of Mo may range from about 10 ppm to 3000 ppm or more, and often with a preferred range of about 20 2000 ppm, and in some instances a more preferred range of about 30 1000 ppm. Friction modifiers of all types may be used alone or in mixtures with the materials of this invention. Often mixtures of two or more friction modifiers, or mixtures of friction modifiers(s) with alternate surface active material(s), are also desirable.

Additives of Grease Composition:

The composition of the invention may be prepared as a grease composition. In the subject embodiment, in order to ensure a practical performance in the case of adapting to a grease application, a thickener or the like may be properly added within the range where the object of the invention is not impaired, as the need arises. Additives which can be added during the preparation of a grease composition are hereunder described.

As the thickener which can be added, all of thickeners such as soap based thickeners, for example, a metal soap, a composite metal soap, etc.; non-soap based thickeners such as Bentone, silica gel, urea based thickeners (urea compounds, urea/urethane compounds, urethane compounds, etc.); and the like can be used. Of these, soap based thickeners and urea based thickeners are preferably used because they are less likely to damage resin-made members.

Examples of the soap based thickener include a sodium soap, a calcium soap, an aluminum soap, a lithium soap, etc. Of these, a lithium soap is preferable in view of excellent waterproof properties and thermal stability. Examples of the lithium soap include lithium stearate, lithium 12-hydroxystearate, etc.

Moreover, examples of the urea based thickener include urea compounds, urea/urethane compounds, urethane compounds, mixtures of these compounds, etc.

Examples of the urea compound, urea/urethane compound and urethane compound include diurea compounds, triurea compounds, tetraurea compounds, polyurea compounds (excluding diurea compounds, triurea compounds and tetraurea compounds), urea/urethane compounds, diurethane compounds, mixtures of these compounds, etc. Preferably, diurea compounds, urea/urethane compounds, diurethane compounds and mixtures of these compounds are exemplified.

Examples of the solid lubricant include polytetrafluoroethylene, boron nitride, fullerene, graphite, fluorinated graphite, melamine cyanurate, molybdenum disulfide, Mo-dithiocarbamate, antimony sulfide, borates of an alkali (alkaline earth) metal, etc.

Examples of the wax include various waxes including natural waxes and mineral oil based or synthetic waxes. Specific examples thereof include a montan wax, a carnauba wax, an amide compound of a higher fatty acid, a paraffin wax, a microcrystalline wax, a polyethylene wax, a polyolefin wax, an ester wax, etc.

Besides, benzotriazole, benzimidazole, thiadiazole and the like are known as the metal deactivator, and these can be used.

A viscosity improver can be added to the foregoing grease composition. Examples of the viscosity improver include polymethacrylate, polyisobutylene, polystyrene, etc.

Poly(meth)acrylate is also known to have an effect of preventing an abnormal sound at a low temperature in a cold district.

In general, a rotary bearing portion of a food-making machine adopts a prelubricated rolling bearing or the like. However, since there may be a possibility that such a mineral oil based grease composition is scattered and brought into contact with foods during the operation of the machine, it may not be said that such is suitable in view of the food hygiene. Moreover, there is a concern that the grease is polluted by bacteria, so that it may be likely considered that there is a possibility that the foods are adversely affected. As a grease composition capable of solving such a problem, there are known a grease composition containing antibacterial zeolite as an antibacterial agent and so forth. Moreover, a natural antibacterial agent is preferable in view of safety. Specifically, chitosans, catechins, Moso bamboo, mustard, an essential oil of wasabi and the like are representative. Besides, antibacterial substances such as colloidal pectin abundant in apple, grape and citrus fruits; polylysin which is a straight-chain polymer of L-lysine as an essential amino acid; protamine which is a basic protein contained in matured testis of salmon, trout, herring and the like; extracts of seed and fruit of *Psoralea corylifolia*; spices obtained by dried leaves of Lamiaceae such as rosemary, sage, thyme and so forth; extracts of *Coix lacryma-jobi* obtained by using a hydrophobic organic solvent; extracts of root and stem of *Cirsium brevicaule*; propolis obtained from honeycomb; and the like can be used.

Of these, catechins which are largely effective against various types of food poisoning are suitable. Above all, epigallocatechin, epicatechin, epicatechin gallate, epigallocatechin gallate, catechin and so forth, which are a water-soluble component contained in tea leaves, are preferable. In general, since such catechins are soluble in water, they are preferably used upon being added with a small amount of a surfactant. However, in the case of a grease composition, there is no need of further adding a surfactant because the thickener also plays a role as the surfactant.

Moreover, the grease composition is also highly adaptable to a rubber to be disposed in the vicinity of a sliding portion. Though such a rubber is not particularly limited, specific examples thereof include a nitrile rubber, a chloroprene rubber, a fluorinated rubber, an ethylene/propylene rubber, an acrylic rubber and composites of these materials.

Static electricity generated in rolling bearings is known to adversely affect, by a radiated noise thereof, a copied image produced by a copying machine, such as distortion, etc., and the copresence of a conductive material is effective for its suppression. The conductive material is added in an amount of from 2 to 10% by mass of the total amount of the grease. Of the conductive materials, carbon black and graphite are suitable, and the both can be used independently or in admixture. In the case of using them as a mixture, the total content is regulated to the foregoing addition amount. Moreover, each of carbon black and graphite is preferably one having an average particle size of from 10 to 300 nm.

Moreover, the conductive material is also known to be effective as an anti-separation agent as described in the section relevant to the extreme pressure agent. As described in JP-A-2002-195277, this conductive material has an effect of suppressing whitening and separation to be caused by a hydrogen ion.

There are also known techniques of adding a hollow filler or a silica particle for the purpose of improving heat-insulating properties of the grease, or conversely, techniques of adding a powder of metal such as copper, etc. for the purpose of promoting heat conduction and heat radiation properties.

As the grease with improved flame retardancy, there are known those obtained by adding a powder of an oxide, a carbonate or the like of an alkali metal or alkaline earth metal to a lithium soap grease, those obtained by adding calcium carbonate and a platinum compound to a silicone grease, and those obtained by allowing a grease to contain a water-absorptive polymer and water.

4. Properties of Composition of the Invention

4.-1 Viscosity

Preferably, the composition of the invention has a viscosity at 40° C. of at most 100 mPa·s, more preferably at most 50 mPa·s, even more preferably at most 30 mPa·s. The composition having a smaller viscosity is preferred as contributing more toward fuel reduction; however, the viscosity of the composition greatly varies depending on the viscosity of the base oil to be used, the structure and the amount to be used of the compound of the invention, and on the co-existing additives. Accordingly, the composition is desired to have a suitable viscosity in accordance with the service environment, and must be determined suitably depending on the environment. However, the invention does not require preventing the reduction in the viscosity of the base oil at high temperature owing to the viscosity index improver in the current technology, and therefore, the composition of the invention is free from the risk of viscosity increase at low temperature owing to addition of a viscosity index improver thereto. Consequently, one characteristic feature of the invention is that the effect of the low-viscosity base oil directly contributes toward fuel reduction.

4.-2 Elementary Composition

Preferably, the constituent elements in the composition of the invention are carbon, hydrogen, oxygen and nitrogen alone. The compound of the above-mentioned formula (Z) can be composed of carbon, hydrogen and oxygen alone. As oil usable as an oily medium, there exist various materials composed of carbon, hydrogen and oxygen alone. By combining these, a composition in which the constituent elements are carbon, hydrogen, oxygen and nitrogen alone can be prepared. Existing lubricant oil generally contain phosphorus, sulfur and heavy metal. The lubricant oil for use in a 2-stroke engine in which the lubricant oil is combusted along with fuel therein does not contain phosphorus and heavy metal in consideration of the environmental load thereof, but the lubricant oil for use in a 4-stroke engine contain sulfur in an amount of about a half thereof. Specifically, it is presumed that in the current lubrication technology, at least the formation of a boundary lubricant film with a sulfur component would be indispensable; however, the load to the catalyst for exhaust gas purification of the lubricant oil, as containing such a sulfur component, is extremely large. Platinum and nickel are used in the exhaust gas purification catalyst, but the poisoning effect of phosphorus and sulfur thereto is a serious problem. From this viewpoint, the merit of the technology that the constituent elements of the composition of lubricant oil are carbon, hydrogen, oxygen and nitrogen alone is extremely great. Further, the technology that the constituent elements are carbon, hydrogen and oxygen alone is the most suitable for the lubricant oil for industrial machines except engine oils, especially for food production-related machines. The current technology takes the elementary composition in consideration of the environment with scarifying the friction coefficient of lubricant oil. This is an extremely favorable technique for metal cutting/working lubricant oil that requires a large amount of water for cooling. This is because, in many cases, the lubricant oil may float or vaporize in air in the form of a mist thereof or the processed waste may be discharged out in the nature system; and therefore, for satisfying both lubrication and environmental protection, it is extremely desirable to replace the existing lubricant oil with the composition of the invention that is composed of carbon, hydrogen and oxygen alone.

4.-3 Liquid Crystallinity

Preferably, the composition of the invention exhibits liquid crystallinity from the viewpoint of the lubrication performance thereof. The reason is because in the composition exhibiting liquid crystallinity, the molecules are aligned in the slide part, and owing to the anisotropic low-viscosity effect thereof, the composition can exhibit a further reduced friction coefficient (for example, see Ken Kawada, Nobuyoshi Ohno; Fuji Film Study Report No. 51, 2006, pp. 80-85).

Regarding the liquid crystallinity of the composition, the compound represented by the formula (Z) therein may express thermotropic liquid crystallinity, or may express lyotropic liquid crystallinity along with the oily medium in the composition.

5. Applications of Composition of the Invention:

The composition of the invention is useful as a lubricating oil. For example, the composition of the invention is fed between the two sliding surfaces and can be used for reducing the friction. The composition of the invention is able to form a film on the sliding surface. As for the material quality of the sliding surface, specific examples of steel include carbon steels for machine structural use; alloy steels for machine structural use such as a nickel-chromium steel material, a nickel-chromium-molybdenum steel material, a chromium steel material, a chromium-molybdenum steel material, an aluminum-chromium-molybdenum steel material, etc.; stainless steel, and maraging steel.

Various metals other than steel, or inorganic or organic materials other than metals are widely used.

Examples of the inorganic or organic materials other than metals include various plastics, ceramics, carbon, etc. and mixtures of these materials, etc. More specific examples of the metal materials other than steel include cast iron, a copper/copper-lead/aluminum alloy, castings of these materials and white metal.

Examples of the organic material include all of general plastics, engineering plastics, such as high-density polyethylenes (HDPE), polyamides, polyacetals (POM), polycarbonates, polyethylene terephthalates, polybutylene terephthalates, polybutylene naphthalates, polyphenylene ethers, poly phenylene Sulfides (PPS), fluorine resins. Tetrafluoroethylene resins (PFPE), polyaryalates, polyamide imides (PAI), polyether imides, polypyromellitimides, polyether ether ketones (PEEK), polysulfones, polyethersulfones, polyimides (PI), polystyrenes, polyethylenes, polypropylenes, phenol resins, AS resins, ABS resins, AES resins, AAS resins, ACS resins, MBS resins, polyvinyl chloride resins, epoxy resins, diallyl phthalate resins, polyester resins, methacryl resins, and ABS/polycarbonate alloy.

Such a resin forms a molding or a resin layer as various components or members, and this grease composition is applied in a portion where it comes into contact with other resin or metal. Specifically, the grease composition is effectively applied to, for example, a sliding portion, a bearing and a resin gear part of automotive electrical equipment represented by an electric power steering, a door mirror and so forth; a resin gear part for audio instruments such as a radio cassette recorder, VTR, a CD player and so forth; a resin gear unit for office automation equipment such as a printer represented by a laser printer, a copying machine, a facsimile and so forth; and a contact portion between a resin material for forming a sliding part of every automotive actuator and an air cylinder interior, with other resin material or a metal material.

Examples of the inorganic material include ceramics such as silicon carbide, silicon nitride, alumina, zirconia, titanium carbide (TiC), zirconium carbide (ZrC), titanium nitride (TiN), etc.; and carbon materials. Moreover, examples of a mixture of these materials include organic-inorganic composite materials in which a plastic is composited with fibers of glass, carbon, aramid, etc., cermet which is a composite material of a ceramic and a metal and so forth.

In the case where a part is composed of a material other than steel, at least a part of the surface of a steel material is covered by a film composed of a metal material other than steel or an organic or inorganic material other than metal materials. Examples of the covering film include magnetic material thin films such as a thin film made of diamond-like carbon and organic or inorganic porous films.

Moreover, the configuration may be achieved in such a manner that a porous sintered layer is formed on at least one of the foregoing two surfaces, and the porous layer is impregnated with the composition of the invention, thereby allowing the lubricant composition to be properly fed onto the sliding surface at the time of sliding. The foregoing porous film may be composed of any material selected among metal materials, organic materials and inorganic materials. Specific examples thereof include sintered metals; porous ceramics formed by allowing fine particles of calcium zirconate ($CaZrO_3$) and magnesia (MgO) to strongly bond to each other; porous glasses obtained by allowing silica and a borate based component to thermally cause phase separation; sintered porous moldings of an ultra-high-molecular weight polyethylene powder; fluorocarbon resin based porous films made of polytetrafluoroethylene, etc.; polysulfone based porous films to be used for a microfilter, etc.; porous films formed by previously allowing a poor solvent of a molding and a monomer for forming the molding to cause phase separation at the time of polymerization; and so forth.

Examples of the metal or metal oxide sintered layer include porous layers formed by sintering a copper based, iron based or $TiO_2$ based powder. The copper based sintered layer can be formed by placing a mixture of a copper powder (for example, 88% by mass), tin (for example, 10% by mass) and graphite (for example, 2% by mass) on a cast iron substrate, compress molding the resultant under 250 MPa and sintering the molding in a reductive gas stream at a high temperature, for example, about 770° C. for about one hour. Moreover, the iron based sintered layer can be formed by placing a mixture of an iron powder having a copper powder (for example, 3% by mass) and chemical carbon (0.6% by mass) added thereto on a cast iron substrate, compress molding the resultant under 250 MPa and sintering the molding in a reductive gas stream at a high temperature, for example, about 770° C. for about one hour. Moreover, the $TiO_2$ sintered layer is formed by placing a mixture of $Ti(OC_8H_{17}$-n) (for example, 33% by mass), a fine powder of $TiO_2$ (for example, 57% by mass) and PEO (molecular weight MW=3,000) on a cast iron substrate and sintering the resultant under heating at 560° C. for 3 hours while irradiating UV rays.

In this connection, the material to be covered by such a porous layer is not specifically limited, and it may be any of the foregoing ceramics, resins and organic-inorganic composite materials or, as a matter of course, may be steel.

The coating film made of the foregoing magnetic material thin film such as a diamond-like carbon thin film, etc. can be formed by a surface treatment. Details of the surface treatment are described in *Tribology Handbook*, 1st edition (2001), Series B, Chapter 3, "Surface Treatment", pages 544 to 574, edited by Japanese Society of Tribologists, all contents of which are adoptable to manufacturing of the mechanical elements of the invention. In general, the surface treatment is achieved for the purpose of improving tribological characteristics through surface modification, wherein the operation of mechanical elements often requires not only low friction and wear resistance but various material characteristics such as low noise, corrosion resistance, chemical stability, heat resistance, dimensional stability, low out-gas, biocompatibility, antibacterial performance and so forth, depending on demands of the operational environment. In consequence, in the invention, the surface treatment is not limited to those aimed at improving the tribological characteristics. Examples of the surface treatment include:

1) formation of a film of aluminum, copper, silver, gold, chromium, molybdenum, tantalum or alloys thereof; a ceramic film of titanium nitride, chromium nitride, titanium carbide, chromium carbide, etc.; and an oxide film of aluminum oxide, silicon dioxide, molybdenum silicide, tantalum oxide, barium titanate, etc., by a physical vapor deposition method by vacuum vapor evaporation, ion plating, sputtering or ion implantation;

2) formation of a film of every metal; a carbide film of WC, TiC, $B_4C$; a nitride film of TiN, $Si_3N_4$, etc.; a boride film of $TiB_2$, $W_2B_3$, etc.; an oxide film of $Al_2O_3$, $ZrO_2$, etc.; an amorphous carbon film containing CrW or a Ti metal; a fluorine-containing carbon film; or a plasma-polymerized polymer, by a chemical vapor deposition method by heat, plasma, light, etc.;

3) a method of imparting characteristics such as wear resistance, anti-seize properties and so forth to a surface layer portion, by a diffusive covering method (chemical reaction process) such as carburization, nitriding, sulfurizing and boronization treatments and so forth; and 4) formation of a film of a metal, a composite metal, etc., by a plating method such as electro-plating, electroless plating and so forth.

The composition of the invention can be utilized for various applications. For example, the composition of the invention is used for fuels for combustion engine, engine oils for internal combustion engine, cutting oils, engine oils for vehicles including automobiles, etc., gear oils, hydraulic oils for automobiles, lubricating oils for marine vessel and aircraft, machine oils, turbine oils, bearing oils, hydraulic oils, oils for compressor and vacuum pump, freezer oils, lubricating oils for cooling apparatuses such as air conditioners or refrigerators having a reciprocating or rotary sealing type compressor, automotive air conditioners dehumidifiers, freezers, refrigerated warehouses, vending machines, showcases, chemical plants, etc, and so forth.

Moreover, the composition of the invention is also useful as a chlorine based compound-free lubricating oil for metal working during working of hot rolling or cutting a metal material, for example, steel materials, Al alloys, etc.; as a metal working oil or plastic working oil such as a cold rolling oil, a cutting oil, a grinding oil, a drawing oil, a press working oil, etc. of aluminum, in particular, as an inhibitor of wear, breakage or surface roughening at the time of high-speed and high-load working; and as a metal working oil composition which can be applied to low-speed and heavy cutting such as brooch working or gun drill working.

Moreover, the composition of the invention can be utilized for various lubricating oils for grease, lubricants for magnetic recording medium, lubricants for micromachine, lubricants for artificial bone and so forth. Moreover, since the elementary composition of the composition can be made of a carbohydrate, by using, as a lubricating oil, a composition containing a cooking oil as a base oil and containing a sorbitan fatty acid ester containing polyoxyethylene ether which is widely used as an emulsifier, a dispersant or a solubilizing agent for cake mixtures, salad dressings, shortening oils, chocolates, etc., a high-performance lubricating oil which is utterly harmless to man can be used for lubrication of members of manufacturing equipment of food-manufacturing line or medical equipment.

Moreover, by emulsifying and dispersing the composition of the invention in a water system or dispersing it in a polar solvent or a resin medium, it can be used as a cutting oil or a rolling oil.

Moreover, the composition of the invention can be utilized as a mold release agent for various applications. For example, the composition of the invention can be used as a mold release agent for polycarbonate resins, flame-retardant polycarbonate resins, crystalline polyester resins which are a main component for image forming toners to be used for electrophotographic apparatus or electrostatic recording apparatus, various thermoplastic resin compositions for molding, semiconductor sealing epoxy resin compositions and so forth. One embodiment of the mold release agent is an embodiment containing 0.01 to 10 parts by mass (preferably from 0.1 to 5 parts by mass) of the compound represented by formula (Z) with respect to 100 parts by mass of resin such as polycarbonate resin.

Moreover, by previously kneading the composition of the invention into textile goods such as clothing, etc. or coating it, it can also be used as an antifouling agent for promoting release of a stain deposited on the textile goods, thereby preventing the stain of the fiber goods.

EXAMPLES

The invention is described in more detail with reference to the following Examples. In the following Examples, the material used, its amount and ratio, the details of the treatment and the treatment process may be suitably modified or changed not overstepping the spirit and the scope of the invention. Accordingly, the invention should not be limitatively interpreted by the Examples mentioned below.

1. Synthesis Example of Exemplary Compound

1.-1 Synthesis Example of Exemplary Compound AII-4

6.8 g (0.05 mol) of pentaerythritol and 20 g (0.2 mol) of succinic anhydride were dissolved in 20 mL of toluene, heated at 150° C. and stirred for 3 hours. This was cooled to 60° C., and 17.6 mL (0.15 mol) of thionyl chloride was added thereto. After 5 minutes, this was heated up to 80° C., further stirred for 2 hours, then cooled, and toluene and excessive thionyl chloride were evaporated away under reduced pressure. 36.5 g (0.205 mol) of triethylene glycol monoethyl ether diluted in 60 mL of toluene was added thereto, and with cooling with ice, 22.8 g (0.288 mol) of pyridine diluted in 10 mL of toluene was gradually added thereto. After heated at 80° C. for 3 hours, this was concentrated and then cooled, and extracted with a system of ethyl acetate-water into an ethyl acetate layer, which was then washed with diluted hydrochloric acid and water, and dried with magnesium sulfate. This was concentrated and purified through silica chromatography with a developing solvent of ethyl acetate/isopropyl alcohol (95/5) to give 22.4 g of a pale yellow oil (Exemplary Compound AII-4).

1.-2 Synthesis Example of Exemplary Compound AII-45

Synthesis of Pentaerythritol Tetra(3-carboxypropiolate)

34.0 g (0.25 mol) of pentaerythritol and 120.1 g (1.2 mol) of succinic anhydride were heated at 150° C. and stirred for 1 hour. This was cooled to room temperature, and 250 mL of ethyl acetate and 250 mL of acetone were added thereto, and left as such for 3 days. The precipitated crystal was taken out through reduced pressure filtration, and washed with a mixed solvent of equal parts of ethyl acetate and acetone to give 98.6 g of a white crystal.

Synthesis of Exemplary Compound AII-45

Two drops of dimethylformamide, 1.76 mL (0.015 mol) of thionyl chloride and 10 mL of toluene were added to 2.68 g (0.005 mol) of pentaerythritol tetra(3-carboxypropiolate). After stirred for 5 minutes, this was heated at 80° C., and further stirred for 2 hours, then cooled, and toluene and excessive thionyl chloride were evaporated away under reduced pressure. 5 g (0.02 mol) of tetraethylene glycol monobutyl ether diluted in 20 mL of toluene was added thereto, and with cooling with ice, 2 mL of pyridine was gradually added thereto. After stirred at room temperature for 1 hour, this was heated at 80° C. for 3 hours. After concentrated, this was cooled and extracted with a system of dichloromethane-water into a dichloromethane layer, which was then washed with diluted hydrochloric acid and water and dried with magnesium sulfate. This was concentrated and purified through silica chromatography with a developing solvent of ethyl acetate/isopropyl alcohol (95/5) to give 5.4 g of a pale yellow oil (Exemplary Compound AII-45).

1.-3 Synthesis Example of Exemplary Compound AII-4

340.0 g of pentaerythritol (by Wako Pure Chemicals, purity 96%) and 1201.0 g of succinic anhydride (by Wako Pure Chemicals) were fed in a reactor, immersed in an oil bath at 150° C., and reacted for 1 hour. 2500 mL of ethyl acetate and 2500 mL of acetone were added to the reaction mixture, stirred, and recrystallized at room temperature. The formed white solid was taken out through filtration and dried to give 990.0 g of a crude product of A.

C(CH$_2$OCOCH$_2$CH$_2$COOH)$_4$    A

The purity of the crude product A was measured through liquid chromatography (HPLC: Shimadzu's trade name, Class-VP/column; CallcellPak C8UG120: Shiseido's trade name), using a solvent of water/tetrahydrofuran (THF)=58/42, at a flow rate of 1 mL/min and at a column temperature of 40° C., in which the flow amount was 10 μL, the sample concentration was 3 g/L and the wavelength for measurement was 210 nm. As a result, the purity was 85%.

134.0 g of the crude product A and 300 mL of toluene were put into a reactor, and heated at an inner temperature of 80° C. 143.0 g of thionyl chloride (by Wako Pure Chemicals) was added thereto, and stirred at 80° C. for 90 minutes. The mixture was cooled to 20° C., then 214.0 g of triethylene glycol monoethyl ether (by Tokyo Chemical) and 500 mL of toluene were added thereto, and further a mixture of 137.0 g of pyridine and 70 mL of toluene was dropwise added thereto. This was heated up to 80° C., stirred for 1 hour, and toluene was evaporated away under reduced pressure. The residue was extracted with 200 mL of ethyl acetate, 40 mL of 1% aqueous hydrochloric acid and 60 mL of water, and the organic layer was further extracted twice with 100 mL of water. The organic layer was evaporated, and finally filtered. Thus, 260 g of a crude, yellow oily product of B.

C(CH$_2$OCOCH$_2$CH$_2$COO(CH$_2$CH$_2$O)$_3$C$_2$H$_5$)$_4$   B(AII-4)

Figure 2:
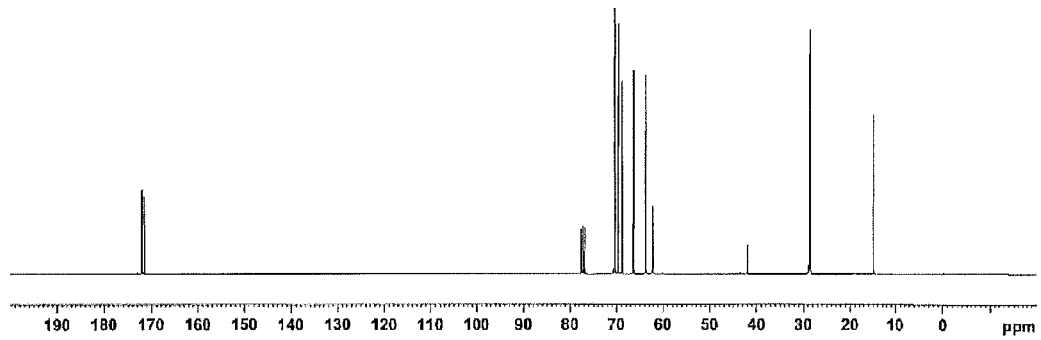
FIG. 2 This is a $^{13}$C-NMR pattern of a heavy chloroform sample of the rough product B synthesized in Example.

Using a superconductive nuclear magnetic resonance absorption apparatus (NMR, Bruker's trade name, AVANCE 400), the crude product B was analyzed in heavy chloroform for $^1$H-NMR and $^{13}$C-NMR. The charts are shown in FIG. 1 and FIG. 2. From the measurement results, it has been confirmed that a compound corresponding to the compound B having the above-mentioned structure, or that is, the Exemplary Compound AII-4 was obtained as the main ingredient.

Figure 3:
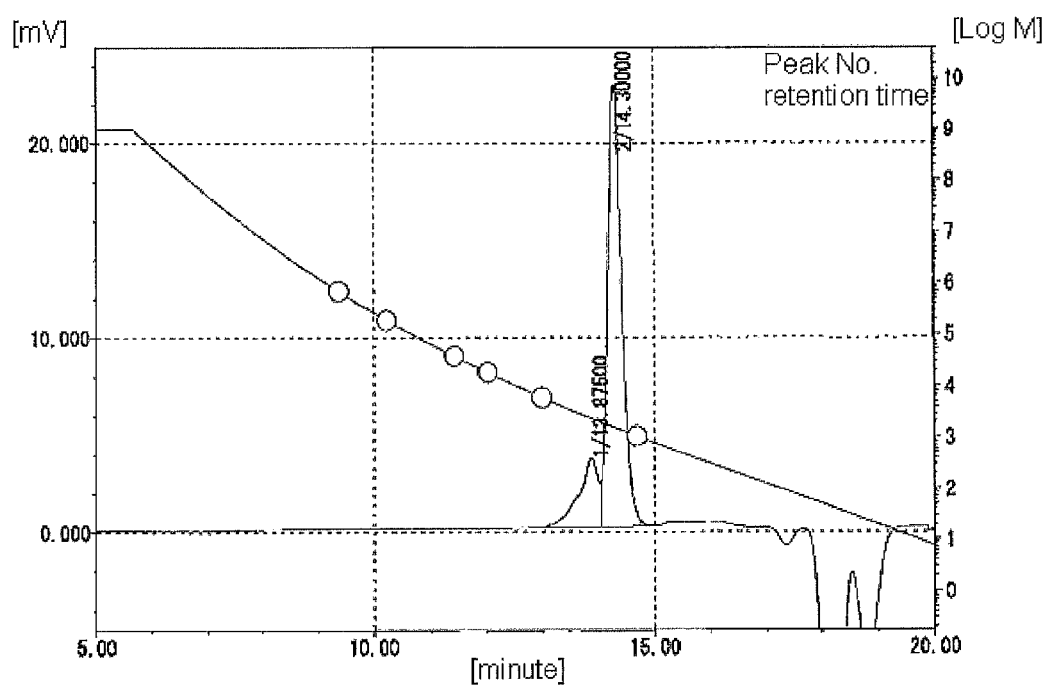
FIG. 3 This is a GPC chart of B synthesized in Example.
Figure 4:
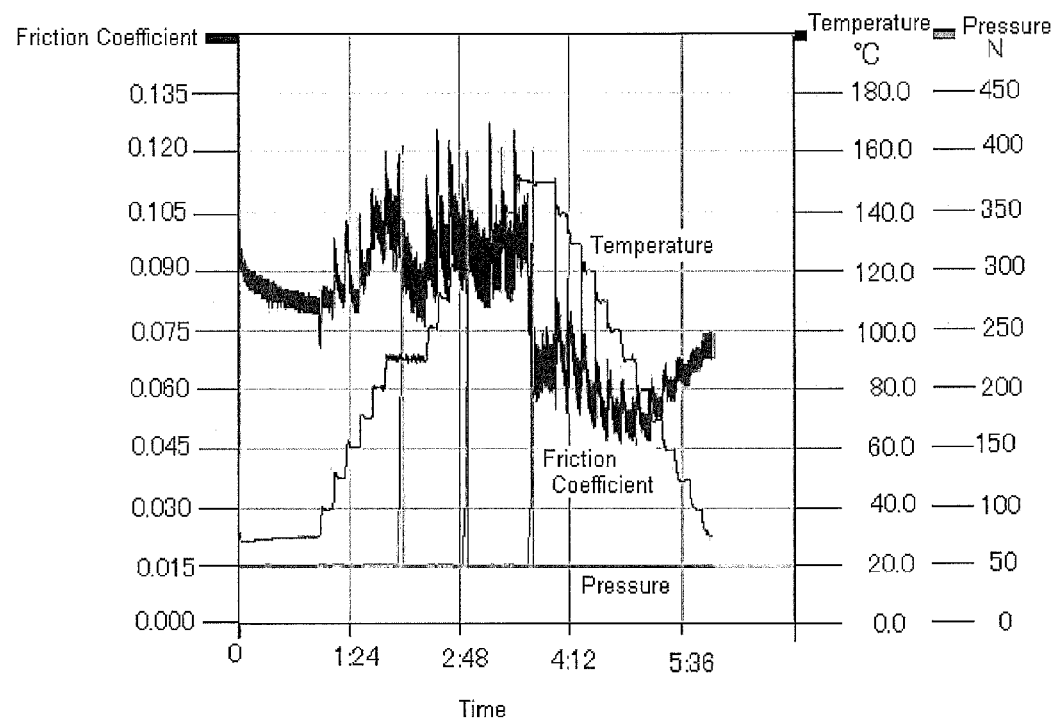
FIG. 4 This shows graphs indicating the results of Test Example 1 of Exemplary Compounds AII-2 and AII-4.
Figure 4:
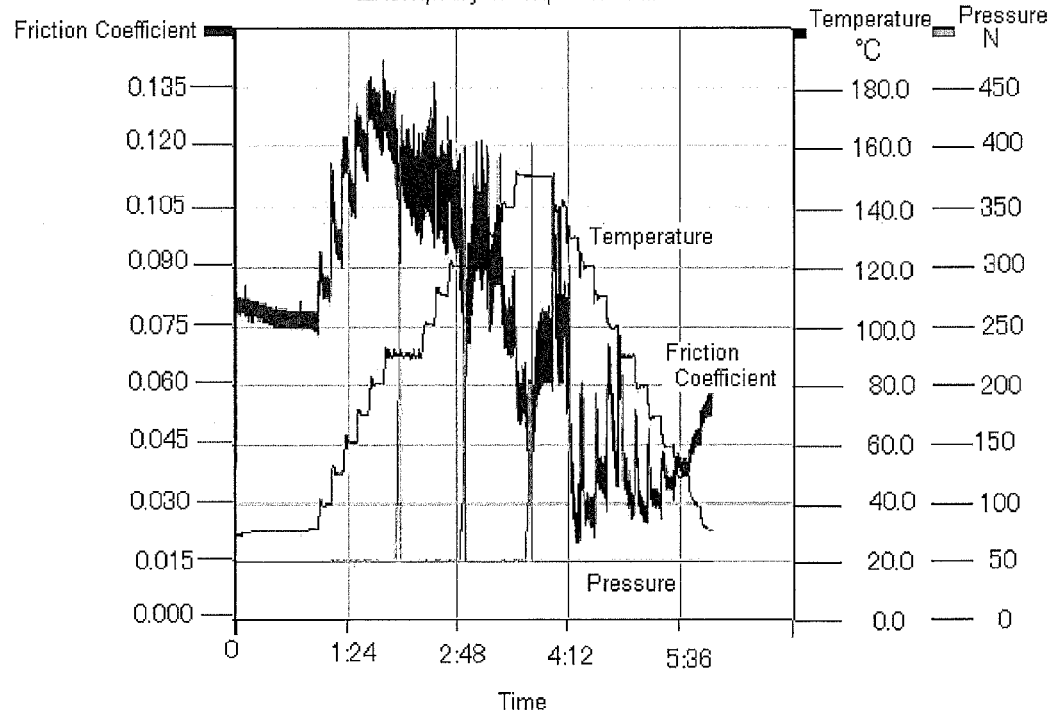
Figure 5:
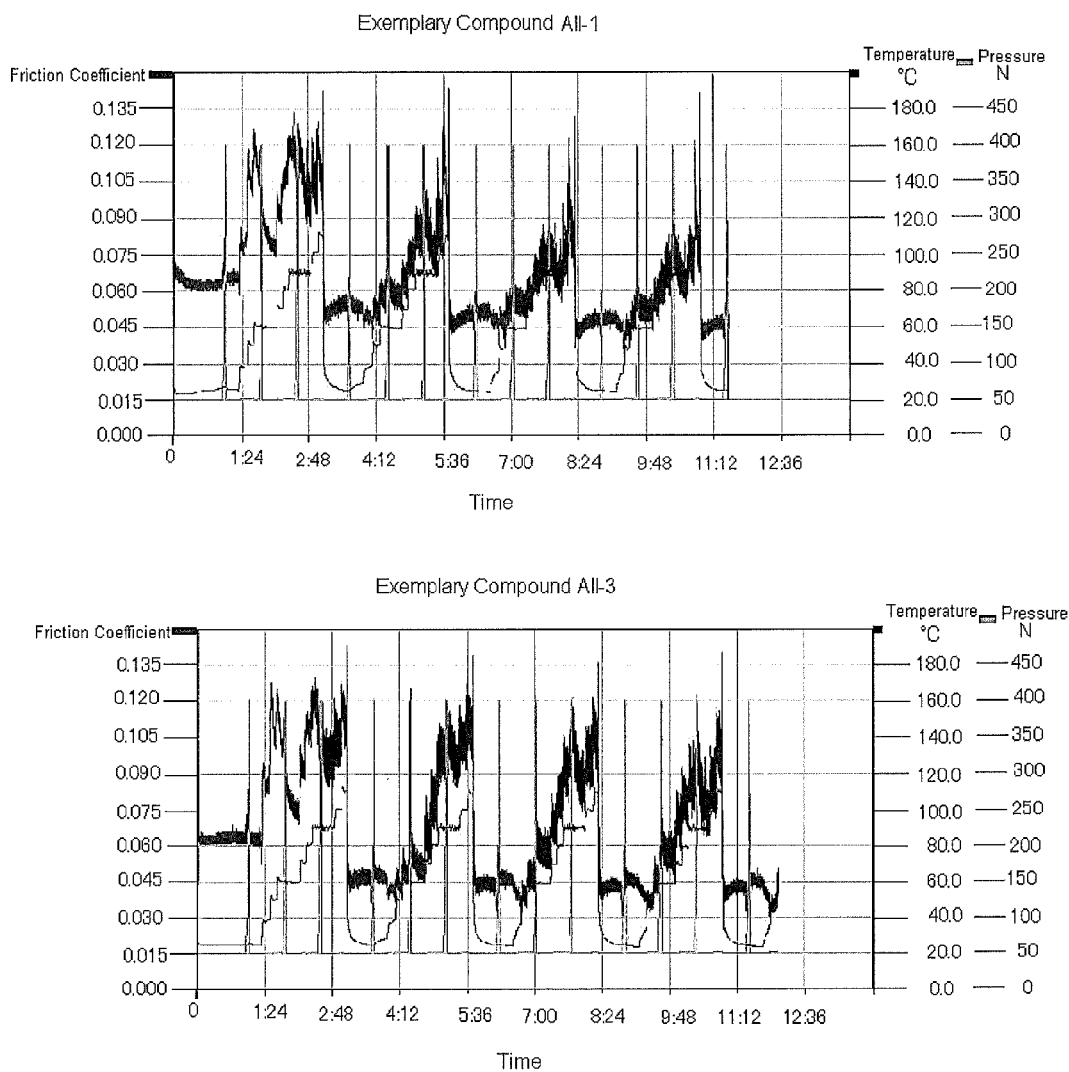
FIG. 5 This shows graphs indicating the results of Test Example 1 of Exemplary Compounds AII-1 and AII-3.
Figure 6:
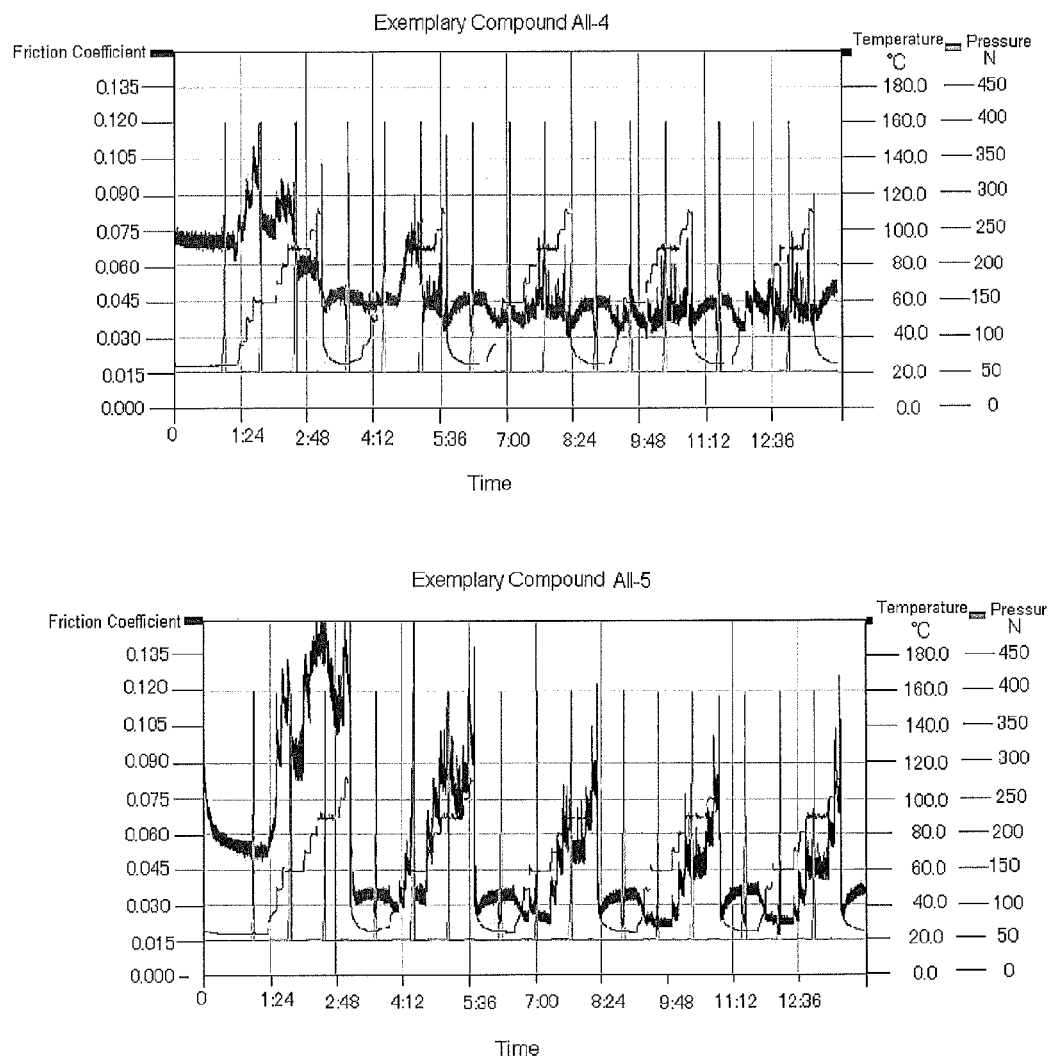
FIG. 6 This shows graphs indicating the results of Test Example 1 of Exemplary Compounds AII-4 and AII-5.
Figure 7:
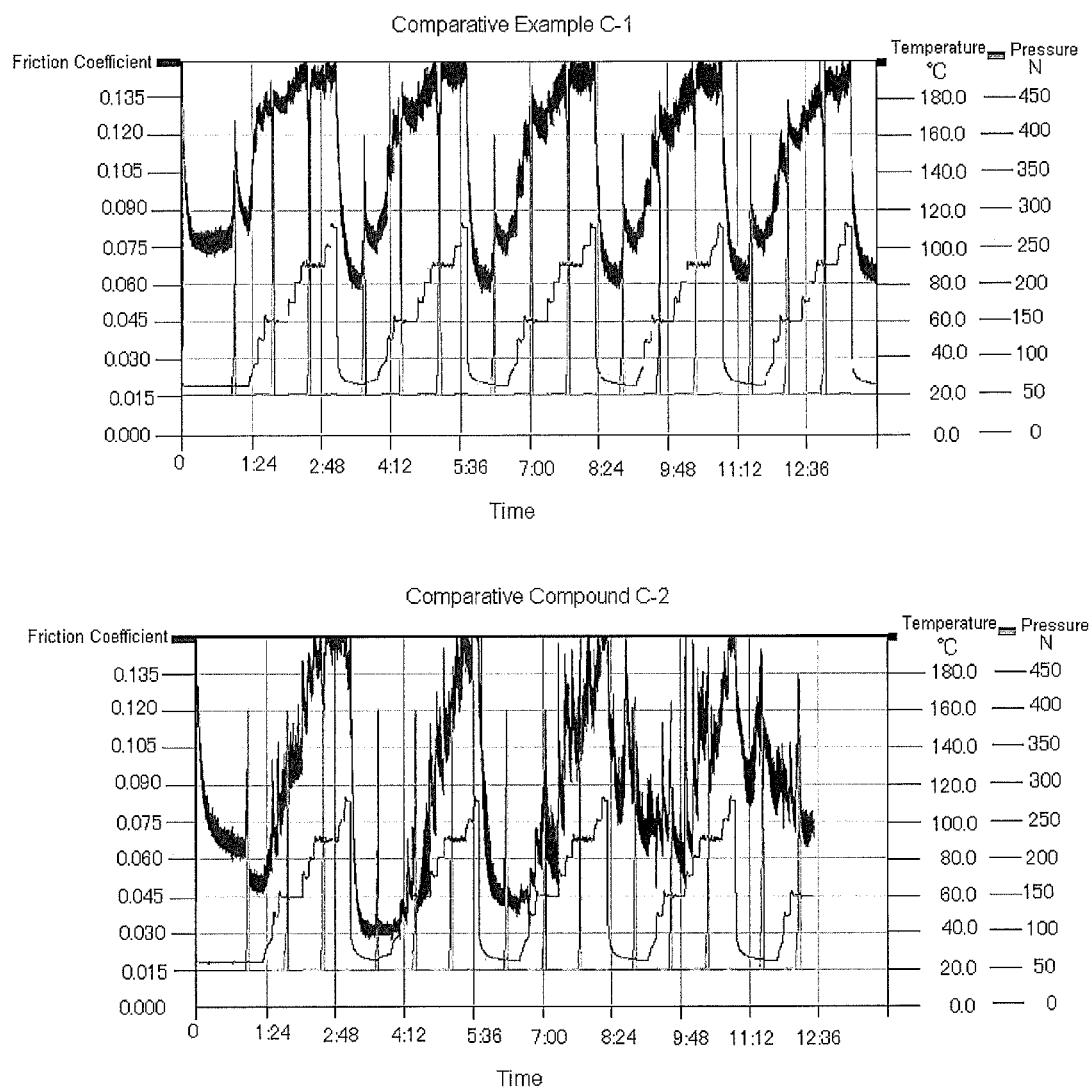
FIG. 7 This shows graphs indicating the results of Test Example 1 of Comparative Compounds C-1 and C-2.
Figure 8:
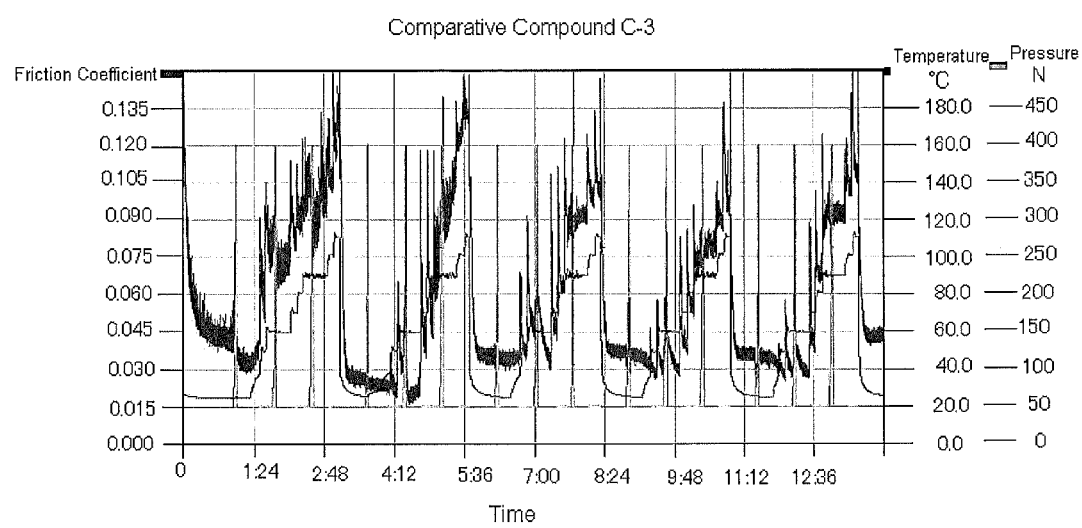
FIG. 8 This shows a graph indicating the results of Test Example 1 of Comparative Compound C-3.

On the other hand, the crude product B was analyzed through gel permeation chromatography (GPC: Tosoh's trade name, HLC-8020/four columns; Tosoh's trade name, TSK-guard column Super HZ-H, TSKgel Super HZM-H, TSKgel Super HZ4000, TSKgel Super HZ2000) using a solvent of tetrahydrofuran (THF), thereby determining the standard polystyrene-equivalent weight-average molecular weight (Mw) thereof and the molecular weight distribution (Mw/Mn) thereof. Mn means the number-average molecular weight of the compound. The measurement condition was: column temperature=40° C., sample concentration=0.1% by weight, sample amount=10 mL, and solvent amount=20 mL. The GPC chart is shown in FIG. 3.

The main ingredient accounting for 82% by weight of the product had Mn=1500 and Mw=1520; and the side product accounting for 18% by weight of the product had Mn=2640 and Mw=2780. The main ingredient is B, and the side product is considered to be the compound C formed through reaction of the impurity of pentaerythritol, bispentaerythritol and/or dipentaerythritol, with succinic anhydride followed by esterification (In the compound C, L represents CH$_2$OCH$_2$, CH$_2$OCH$_2$OCH$_2$ and/or CH$_2$OCOCH$_2$CH$_2$COOCH$_2$).

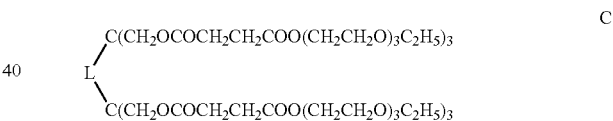

C

The Exemplary Compound AII-4 used in the following Test Examples is a pure compound AII-4.

1.-4 Synthesis Example of Exemplary Compound AII-7

The Exemplary Compound AII-7 was synthesized quite in the same manner as that for synthesis of the Exemplary Compound AII-45 and using pentaerythritol tetra(3-carboxypropiolate) as the starting compound, except that the alcohol was changed to polyethylene glycol monobutyl ether produced by Takemoto Oils and Fats and having a mean degree of polymerization n=20. The compound was a pale yellow crystal (melting point, 33° C.).

Various exemplary compounds were prepared in the similar manner as the above. Regarding some of them, their NMR spectra data and IR data are shown below.

Exemplary Compound AII-1:

$^1$H NMR (400 MHz, CDCl$_3$) δ4.25 (8H, t), 4.13 (8H, s), 3.70 (8H, m), 3.64 (8H, m), 3.56 (8H, m), 3.39 (12H, s), 2.65 (16H, m),

FT-IR (neat) cm$^{-1}$: 3614(w), 3461(w), 2879(s), 1986(b), 1744(s), 1454(s), 1392(s), 1349(s), 1254(b), 1156(s), 1028 (s), 933(m), 858(s) cm$^{-1}$.

Exemplary Compound AII-2:

$^1$H NMR (400 MHz, CDCl$_3$) δ4.25 (8H, t), 4.13 (8H, s), 3.70 (8H, t), 3.64 (8H, m), 3.59 (8H, m), 3.53 (8H, q), 2.64 (16H, m), 1.21 (12H, t).

FT-IR (neat) cm$^{-1}$: 3461(w), 2974(s), 2871(s), 1749(s), 1454(s), 1388(s), 1350(s), 1251(b), 1165(s), 1036(s), 941 (m), 860(m) cm$^{-1}$.

Exemplary Compound AII-3:

$^1$H NMR (300 MHz, CDCl$_3$) δ4.24 (8H, t), 4.13 (8H, s), 3.67 (32H, m), 3.55 (8H, m), 3.38 (12H, s), 2.64 (16H, m).

FT-IR (neat) cm$^{-1}$: 3520(b), 2878(s), 1972(b), 1746(s), 1455(s), 1390(s), 1350(s), 1253(s), 1162(s), 1033(s), 942(m), 856(s) cm$^{-1}$.

Exemplary Compound AII-4:

$^1$H NMR (400 MHz, CDCl$_3$) δ4.24 (8H, t), 4.13 (8H, s), 3.70 (8H, t), 3.66 (24H, m), 3.60 (8H, m), 3.53 (8H, q), 2.64 (16H, m), 1.21 (12H, t).

FT-IR (neat) cm$^{-1}$: 3513(b), 3464(w), 2972(s), 2870(s), 1960(b), 1746(s), 1454(s), 1387(s), 1349(s), 1249(b), 1162 (s), 1036(s), 945(s), 861(m) cm$^{-1}$.

Exemplary Compound AII-5:

$^1$H NMR (300 MHz, CDCl$_3$) δ4.24 (8H, t), 4.13 (8H, s), 3.67 (32H, m), 3.58 (8H, m), 3.46 (8H, m), 2.64 (16H, m), 1.57 (8H, tt), 1.36 (8H, tq), 0.91 (12H, t).

FT-IR (neat) cm$^{-1}$: 3615(w), 3465(w), 2957(s), 2870(s), 1971(b), 1748(s), 1459(s), 1412(s), 1388(s), 1350(s), 1252 (s), 1163(s), 1037(s), 860(s), 739(w) cm$^{-1}$.

2. Test Example 1

Evaluation of Compound

The Exemplary Compounds and Comparative Compounds were evaluated in point of the lubricity characteristics thereof, using Optimol's reciprocating friction wear tester (SRV) under the condition mentioned below.

Evaluation and Test Method According to Reciprocating (SRV) Friction Wear Test:

The friction coefficient was determined under the test condition mentioned below, using a reciprocating (SRV) friction wear tester.

Test Piece (friction material): SUJ-2.

Plate: 24 mm diameter×7 mm thickness; surface roughness, 0.45 to 0.65

Cylinder: 15 mm diameter×22 mm width, surface roughness, up to 0.05 μm.

Temperature: 30 to 150° C.

Load: 50 N, 75 N, 100 N, 200 N and 400 N.

Amplitude: 1.5 mm.

Frequency: 50 Hz.

Time-dependent Pattern of Temperature and Load:

The temperature was 30° C. or higher than the melting point (liquid state) by default, and after kept for a predetermined period of time, the sample was heated up to 150° C. every 10 minutes by 10° C., and thereafter cooled near to the melting point thereof every 10 minutes by 10° C.

The pressure (load) was changed twice at 90° C. and once each at 120° C. and 150° C. in a profile of 50 N→75 N→100 N→200 N→400 N→50 N every minute.

The Exemplary Compounds used for evaluation were AII-1, 2, 3, 4 and 5. As the Comparative Compounds, used were pentaerythritol tetra(2-ethylhexanoate) not having an alkyleneoxide group (C(CH$_2$OCOCH$_2$(C$_2$H$_5$)C$_4$H$_9$-n)$_4$): Comparative Compound C-1); C{CH$_2$OC$_2$H$_4$CO$_2$(C$_2$H$_4$O)$_3$C$_2$H$_5$}$_4$ in which the number of the carbonyl groups is smaller by one than the Exemplary Compound AII-4 (Comparative Compound C-2); and C{CH$_2$OCOC$_2$H$_4$O(C$_2$H$_4$O)$_3$C$_2$H$_5$}$_4$ which forms an ester bond to pentaerythritol but is an ester of a monobasic acid and in which the number of the carbonyl groups is smaller by one than the Exemplary Compound AII-4 (Comparative Compound C-3).

The measurement results are shown in FIG. 4 to FIG. 8.

From the measurement results in FIG. 4 to FIG. 8, it is understood that the Exemplary Compounds AII-1 to 5 have a smaller friction coefficient than the Comparative Compounds C-1 to 3.

The friction coefficient of the Exemplary Compound AII-5 of the formula (Z) rapidly increased at around the melting point thereof in the course of the initial heating stage, and the reason is considered because the influence of the (elastic) fluid lubricant on the interface roughness would have appeared sensitively to the temperature change in the initial sliding stage. Afterwards, it is understood that, like that of AII-1 to 4, the friction coefficient of AII-5 is lower than that of the Comparative Compounds C-1 to 3.

The abrasion depth of the slide part of the test piece after the friction slide test with the compound was measured with a laser microscope, and the evaluation results are shown below.

TABLE 1

| Compound No. | Abrasion Depth [μm] |
|---|---|
| Exemplary Compound AII-1 | 0.09 |
| Exemplary Compound AII-2 | 0.12 |
| Exemplary Compound AII-3 | 0.04 |
| Exemplary Compound AII-4 | 0.02 |
| Exemplary Compound AII-5 | 0.07 |
| Comparative Compound C-1 | 0.35 |
| Comparative Compound C-2 | 0.42 |
| Comparative Compound C-3 | 0.45 |

The results shown in the Table confirm the following.

When the Exemplary Compounds of the formula (Z) were sued, the abrasion depth was extremely small, and few wear marks remained. On the other hand, when the Comparative Compounds were used, there remained clear wear marks. Specifically, in point of the abrasion depth, there was found a clear difference between the Exemplary Compounds and the Comparative Compounds.

3. Test Example 2

Performance Evaluation of Grease Composition

Using the Exemplary Compounds shown in the following Table, grease samples each having the composition shown in the following Table were prepared. In addition, a comparative grease sample C-1 having the composition shown in the following Table was also prepared.

In a friction test, the friction coefficient and the abrasion mark depth were measured. In the Examples, the friction coefficient was measured using a reciprocating friction wear tester (SRV friction wear tester), and the friction test was carried out under the test condition mentioned below. The results with the grease samples of the Examples are shown in the following Table 3; and the results with the comparative grease sample C1 are in the following Table 4.

Test Condition:

The test condition is a ball-on-plate condition.

Test Piece (friction material): SUJ-2.

Plate: ϕ24×6.9 mm.

Ball: ϕ10 mm.

Temperature: 70° C.

Load: 100 N.
Amplitude: 1.0 mm.
Frequency: 50 Hz.
Test Time: 30 minutes after the start of the test, the measurement was started.

TABLE 2

|  | Grease Sample No. | | |
|---|---|---|---|
|  | 1 | 2 | 3 |
| Compound of the Invention (base oil) | AII-4 | AIV-4 | AVII-3 |
| % by mass | 73 | 80 | 83 |
| Thickener % by mass |  |  |  |
| lithium stearate | 27 | 20 | — |
| urea*1 | — | — | 17 |
| Friction Coefficient | 0.045 | 0.065 | 0.055 |
| Wear Mark depth (µm) | 0.45 | 0.48 | 0.58 |

*1 Prepared by reacting 1 equivalent of diphenylmethane 4,4'-diisocyanate and 2 equivalents of octadecylamine.

TABLE 3

|  |  | Comparative Grease Sample No. C-1 |
|---|---|---|
| Comparative Compound C-1 | % by mass | 75 |
| Thickener | % by mass |  |
| lithium stearate |  | 25 |
| urea*1 |  | — |
| Friction Coefficient |  | 0.087 |
| Wear Mark depth (µm) |  | 0.74 |

*1 Prepared by reacting 1 equivalent of diphenylmethane 4,4'-diisocyanate and 2 equivalents of octadecylamine.

The results shown in the above Tables confirm that the grease composition samples of the Examples of the invention noticeably exhibit both the friction reducing effect and the wear preventing effect thereof.

4. Test Example 3

Performance Evaluation of Composition of the Invention as Mold Lubricant 0.4 parts by mass of the Exemplary Compound shown in the following Table or the Comparative Compound C-1 was mixed in 100 parts by mass of a polycarbonate resin (by Sumitomo Dow, molecular weight 20500), using a tumbler, and then pelletized under the condition of the melting temperature 280° C., using a double-screw extruder.

The pellets were molded into a boxy article (draft angle, 2°) having a width 200×length 250×depth 400 mm and a thickness of 2.5 mm, and the load applied to the ejector when the box was released from the mold was recorded in terms of the voltage. The obtained power value was converted into a power (kgf), from which the mold release resistance was obtained. The results are shown in the following Table. The sample having a mold release resistance of at most 450 kgf can be said good for practical use.

TABLE 4

|  | Example | | | Comparative Example |
|---|---|---|---|---|
| Mold Release Sample No. | 1 | 2 | 3 | C-1 |
| Polyester | AII-4 | AII-7 | AIV-1 | C-1 |
| (amount added: part by mass) | (0.4) | (0.4) | (0.4) | (0.4) |
| Polycarbonate, | 100 | 100 | 100 | 100 |
| amount added (part by mass) |  |  |  |  |
| Mold Release Resistance (kgf) | 380 | 410 | 350 | 460 |

The results in the above Table confirm that the Examples of the compositions of the invention are excellent in mold releasability.

5. Test Example 4

Evaluation of Composition of the Invention as Lubricant Oil for Internal Combustion Engine A lubricant oil composition was prepared, comprising the Exemplary Compound shown in the following Table, a base oil (100 Neutral Oil, having a viscosity at 100° C. of 4.4 mm/s$^2$), the ingredient shown in the following Table in the amount also shown therein, and 2.0% by mass of a metal cleaner, calcium sulfonate; and the friction coefficient of the composition was measured. The results are shown in the following Table. The friction coefficient of the lubricant oil composition was measured, using a reciprocating slide friction tester [SRV friction tester]. The frequency was 50 Hz, the amplitude was 1.5 mm, the load was 50 N, the temperature was 65° C., and the test time was 30 minutes.

TABLE 5

| Lubricant Oil Composition | | Example | | | | Comparative Example | | | |
|---|---|---|---|---|---|---|---|---|---|
| Sample No. | | 1 | 2 | 3 | 4 | C1 | C2 | C3 | C4 |
| Compound of the Invention (% by mass) |  | AII-4 (50.0%) | AIV-3 (35.0%) | AV-3 (15.0%) | AIII-1 (35.0%) | — | — | — | — |
| MoDTC | amount of Mo in $C_8$—MoDTC*1 (ppm) | — | — | — | 400 | 400 | — | 400 | 400 |
|  | amount of Mo in $C_{16}$—MoDTC*2 (ppm) | — | — | — | — | — | 800 | — | — |
| ZnDTP | amount of phosphorus in $C_4/C_5$ZnDTP (primary) (% by mass) | — | — | — | — | — | — | 0.1 | — |
|  | amount of phosphorus in $C_8$ZnDTP (primary) (% by mass) | — | — | — | — | 0.1 | 0.1 | — | — |
|  | amount of phosphorus in | — | — | — | — | — | — | — | 0.1 |

TABLE 5-continued

| Lubricant Oil Composition | | Example | | | | Comparative Example | | | |
|---|---|---|---|---|---|---|---|---|---|
| | Sample No. | 1 | 2 | 3 | 4 | C1 | C2 | C3 | C4 |
| Ash-free Dispersant | $C_3/C_6$ZnDTP (secondary) (% by mass) | | | | | | | | |
| | Boron-Containing Succinimide (% by mass) | — | — | 5 | 5 | 5 | 5 | 5 | 5 |
| Friction Coefficient | | 0.031 | 0.071 | 0.048 | 0.033 | 0.102 | 0.113 | 0.138 | 0.097 |

*1$C_8$—MoDTC: oxymolybdenum sulfide N,N-dimethyl dithiocarbamate
*2$C_{16}$—MoDTC: oxymolybdenum sulfide N,N-di-tridecyl dithiocarbamate
*3$C_4/C_5$ ZnDTP (primary): zinc n-butyl-n-pentyl dithiophosphate
*4$C_8$ ZnDTP (primary): zinc di-2-ethylhexyl dithiophosphate
*5$C_3/C_6$ ZnDTP (secondary): zinc isopropyl-1-ethylbutyl dithiophosphate The lubricant oil composition samples Nos. 1 to 4 of the above-mentioned Examples all had a low friction coefficient and showed good friction characteristics. As opposed to these, it is understood that the lubricant oil composition samples Nos. C1 to C4 of the Comparative Examples, as containing an organic molybdenum compound such as molybdenum dithiocarbamate (MoDTC) or oxymolybdenum sulfide organophosphorodithioate (MoDTP) or the like, all had a high friction coefficient and the friction characteristics thereof are poor. It is understood that, although the lubricant oil compositions of the Examples of the invention do not have an effect of adsorbing to the friction iron surface, they are effective for reducing the friction coefficient on the same level as or on a higher level than that of molybdenum compound-containing lubricant oil compositions that are said to strongly adsorb to the friction surface, even under the operation condition at a middle or low temperature and at a low-speed rotation.

Accordingly, the lubricant oil compositions of the invention are favorably used for internal combustion engines such as automobile engines, etc.; and automobile lubricant oils such as gear oils, automatic transmission liquids, shock absorber oils, etc.

6. Test Example 5

Evaluation of Composition of the Invention as Metal Working Lubricant Oil

Various types of metal working lubricant oil compositions, each comprising the ingredients (% by weight) shown in the following Table, were prepared and tested according to the following test methods.

As the rolling material, used was JIS A-1050 H18 (thickness, 0.8 mm).

As the base oil, used was a mineral oil with 3.2 mm²/s (40° C.); and as the oily agent, used were lauryl alcohol and myristyl alcohol (6/4).

(i) Rolling Test

In a rolling test under the condition mentioned below, the rolling reduction ratio {(initial thickness of material−thickness of rolled material)/initial thickness of material}×100%, was increased gradually, in which the rolling reduction ratio before scuffing or herringbone failure (critical rolling reduction ratio) was measured.
Rolling Reduction Ratio: from 40% (increased at regular time intervals)
Rolling Speed: 50 m/min (ii) Test for Measuring the Roll Coating Amount A coil having a length of 300 m was rolled continuously for a total of 3 coils under the following condition, then the roll coating formed on the surface of the roll was dissolved in an aqueous 5% sodium hydroxide solution, and the amount of aluminium in the solution was quantitatively determined through atomic absorptiometry. From the data, the roll coating amount was computed.
Rolling Reduction Ratio: 50%
Rolling Speed: 300 m/min (iii) Test for Measuring the Amount of Abrasion Powder A coil having a length of 300 m was rolled continuously for a total of 3 coils under the following condition. After the test, the amount of aluminium in the oil was measured through atomic absorptiometry, from which the aluminium concentration in the oil was computed. After the rolling, the abrasion powder adhering to the aluminium surface was wiped away with absorbent cotton, and the thus-collected abrasion powder was analyzed through atomic absorptiometry to determine the amount of the abrasion powder adhering to the rolled plate surface. Both the aluminium amount in the oil and the abrasion powder adhering to the plate were converted to those in terms of the data per m² of the rolled plate, and the total of the two was taken here as the amount of the abrasion powder.
Rolling Reduction Ratio: 50%
Rolling Speed: 300 m/min The test results are shown in the following Table.

TABLE 6

| Metal Working Lubricant Oil | Example | | | | Comparative Example |
|---|---|---|---|---|---|
| Composition Sample No. | 1 | 2 | 3 | 4 | C1 |
| Compound of the Invention (amount added, part by mass) | AII-9 (100) | AVI-8 (7) | AIV-10 (10) | AII-14 (15) | no addition (—) |
| Amount of Base Oil Added (part by mass) | — | 90 | 90 | 45 | 93 |

TABLE 6-continued

| Metal Working Lubricant Oil | Example | | | | Comparative Example |
|---|---|---|---|---|---|
| Composition Sample No. | 1 | 2 | 3 | 4 | C1 |
| Water | — | — | — | 40 | — |
| Amount of Oily Agent Added (part by mass) | — | 3 | — | — | 7 |
| Critical Rolling Reduction Ratio % | 75 | 80 | 73 | 77 | 60 |
| Coating Amount mg | 0.9 | 1.1 | 1.3 | 0.6 | 1.9 |
| Amount of Abrasion Powder ppm | 83 | 65 | 91 | 77 | 201 |

From the results shown in the above Table, it is understood that the metal working lubricant oil composition samples Nos. 1 to 4 of Examples of the invention are resistant to aluminum working at high speed and at high working ratio, and can improve the working environment, and that the samples can noticeably prevent the formation of metal soap and the generation of abrasion powder.

7. Test Example 6

Sintered Bearing Friction Performance Evaluation with Composition of the Invention Two sintered bearing samples were put in a glass container, in which the samples were immersed in a lubricant oil sample (4 mL) shown in the following Table and heated in a thermostat bath at 150° C. for 300 hours. The sintered bearing samples used here were sintered bearings each having an inner diameter of 3 mm, an outer diameter of 6 mm and a height of 2.5 mm (EAK-3, manufactured by Hitachi Powdered Metals). The constituent metal ingredients of the bearing were Cu: from 50 to 55% by weight, Sn: from 1 to 3% by weight, P: from 0.1 to 0.5% by weight, C: at most 1.0% by weight, others: at most 0.5% by weight, with balance of Fe.

After the bearing was immersed under heat in the lubricant oil sample, the friction coefficient of the bearing was measured. The results are shown in the following Table.

Regarding the test condition, the bearing was SUS420J2, the load was 30 gf, the rotation number was 2000 rpm, the clearance was 15 μm, and the atmosphere temperature was 25° C.

TABLE 7

| Sintered Bearing Lubricant Oil Sample No. | Base Oil*1 | Antioxidant*2 | Compound of (Z) | Friction Coefficient Heating Time [hrs.] | |
|---|---|---|---|---|---|
| | | | | 0 | 300 |
| 1 | DOS | — | — | 0.03 | 0.31 |
| 2 | — | — | AII-2 | 0.03 | 0.15 |
| 3 | — | — | AII-4 | 0.03 | 0.19 |
| 4 | — | AO-1 | AII-4 | 0.03 | 0.10 |
| 5 | — | — | AI-7 | 0.05 | 0.12 |
| 6 | — | — | AI-11 | 0.03 | 0.09 |
| 7 | — | — | AI-22 | 0.04 | 0.18 |
| 8 | — | AO-2 | AI-22 | 0.04 | 0.13 |
| 9 | — | — | AII-7 | 0.07 | 0.18 |
| 10 | — | — | AII-12 | 0.03 | 0.23 |
| 11 | — | — | AII-22 | 0.06 | 0.17 |
| 12 | — | — | AII-36 | 0.04 | 0.12 |
| 13 | — | — | AII-43 | 0.04 | 0.16 |
| 14 | — | — | AIII-3 | 0.04 | 0.10 |
| 15 | — | — | AIII-6 | 0.04 | 0.09 |
| 16 | — | — | AIII-9 | 0.04 | 0.18 |
| 17 | — | — | AIII-3 | 0.04 | 0.10 |
| 18 | — | — | AIV-3 | 0.03 | 0.09 |
| 19 | — | — | AIV-4 | 0.03 | 0.13 |
| 20 | — | — | AV-5 | 0.04 | 0.13 |
| 21 | — | — | AVI-2 | 0.03 | 0.09 |
| 22 | — | — | AVII-3 | 0.04 | 0.18 |
| 23 | — | — | AVIII-1 | 0.03 | 0.26 |
| 24 | TMP | — | — | 0.04 | 0.44 |
| 25 | — | — | AII-14 | 0.04 | 0.19 |
| 26 | — | AO-2 | AII-4 | 0.04 | 0.16 |
| 27 | DOS/SHC | — | — | 0.03 | 0.36 |
| 28 | DOS(0.3) | — | AII-1(0.7) | 0.03 | 0.18 |
| 29 | DOS(0.3) | AO-1 | AII-3(0.7) | 0.03 | 0.075 |
| 30 | DOS(0.3) | AO-1 | AII-4(0.7) | 0.03 | 0.13 |

*1Base Oil DOS (dibasic acid ester)/dioctyl sebacate (viscosity: 11.59 cSt, 40° C.) TMP (polyol ester)/trimethylolpropane tricaprate (viscosity: 14.01 cSt, 40° C.) SHC (synthetic hydrocarbon): hydrogenated polybutene (viscosity: 25.10 cSt, 40° C.) DOS/SHC: mixed oil (mixing ratio: 80/20, viscosity: 13.50 cSt)
*2Antioxidant The amount of AO-1 and AO-2 added is 0.5% by mass each. AO-1: octadecyl 3-(3,5-di-t-butyl-4-hydroxyphenol) AO-2: zinc di-amyl dithiocarbamate From the results shown in the above Table, it is understood that, when the lubricant oil sample containing the compound represented by the above-mentioned formula (Z) is used, the friction coefficient of the bearing greatly lowers, and in addition, when the antioxidant is additionally used, it exhibits the effect of reducing the friction coefficient. Reduction in the friction coefficient of bearing contributes toward power saving and life prolongation of the memory devices, household electric appliances and others using the bearing.

8. Test Example 7

Evaluation of Molybdenum Complex of the Invention

Molybdenum complex-containing lubricant oil composition of the invention comprising the ingredients shown in the following Table (Sample Nos. 2 to 5 of Examples), and a comparative sample No. 1 comprising the base oil alone were prepared. Using the same Optimol's SRV reciprocating slide friction tester as that used for evaluation in Test Example 1, the samples were tested for the friction characteristics thereof under the condition of a load of 400 N, a frequency of 50 Hz, an amplitude of 1.5 mm, and an oil temperature of 75° C./30 minutes or 130° C./24 hours.

In the following Table, the numerical data of the ingredients are in terms of % by mass.

TABLE 8

| Molybdenum Complex-Containing Lubricant | Example | | | | |
|---|---|---|---|---|---|
| Oil Sample No. | 1 | 2 | 3 | 4 | 5 |
| Lubricant Oil Base Oil (1) | 100 | 93 | 92.4 | 79.4 | — |
| Compound of Formula (Z) of the Invention | — | — | — | — | AII-4 (93) |
| Mo Complex of the Invention % by mass) | — | AIX-2 (7) | AXa-1 (7.6) | AXa-3 (7.6) | AIX-2 (7) |
| Zn Complex of the Invention (% by mass) | — | — | — | AXb-1 (13) | — |
| Friction Coefficient (SRV) 75° C./30 min. | 0.159 | 0.071 | 0.083 | 0.067 | 0.065 |
| Friction Coefficient (SRV) 130° C./120 hrs. | >0.3 | 0.063 | 0.089 | 0.041 | 0.038 |

(1) Lubricant oil base oil: hydrogenation-purified mineral oil (total aromatic content: 1.3%, sulfur content: 10 ppm, 100° C. dynamic viscosity: 5.1 mm²/s, viscosity index: 138)

From the results in the above Table, it is understood that the lubricant compositions containing the molybdenum complex of the invention (Sample Nos. 2 to 5) have excellent low-friction characteristics, as compared with the comparative oil comprising base oil alone. Further, it is understood that use of the compound of the formula (Z) as the base oil is superior to use of mineral oil as the base oil.

The invention claimed is:

1. A composition comprising at least one compound represented by the following formula (Z):

$$A\text{-}L\text{-}\{D^1\text{-}(E)_q\text{-}D^2\text{-}(B)_m\text{—}Z^1\text{—}R\}_p \qquad (Z)$$

wherein A represents a p-valent, linear or cyclic residue;

L represents a single bond, an oxy group, a substituted or unsubstituted oxymethylene group represented by the following formula (A-a), or a substituted or unsubstituted oxyethyleneoxy group represented by the following formula (A-b);

Alk represents a hydrogen atom, a $C_1$ to $C_6$ alkyl group, or a cycloalkyl group;

$$-(O\text{—}C(Alk)_2)\text{-} \qquad (A\text{-}a)$$

$$-(O\text{—}C(Alk)_2C(Alk)_2O)\text{-} \qquad (A\text{-}b)$$

p indicates an integer of at least 2;

$D^1$ represents a carbonyl group (—C(═O)—) or a sulfonyl group (—S(═O)$_2$—), and $D^1$'s may be the same or different;

$D^2$ represents a carbonyl group (—C(═O)—), a sulfonyl group (—S(═O)$_2$—), a carboxyl group (—C(═O)O—), a sulfoxyl group (—S(═O)$_2$O—), a carbamoyl group (—C(═O)N(Alk)-), or a sulfamoyl group (—S(═O)$_2$N(Alk)-), and $D^2$'s may be the same or different;

Alk represents a hydrogen atom, a $C_1$ to $C_6$ alkyl group, or a cycloalkyl group;

E represents a divalent group selected from the group consisting of an alkylene group, a cycloalkylene group, an alkenylene group, an alkynylene group, an arylene group, a divalent heterocyclic aromatic group, a heterocyclic non-aromatic group, an imino group, an alkylimino group, an oxy group, a sulfide group, a sulfenyl group, a sulfonyl group, a phosphoryl group and an alkyl-substituted silyl group, which may be substituted or unsubstituted, and any combinations of two or more of those groups;

q indicates an integer of 0 or more; and when q is 2 or more, E's may be the same or different;

R represents a substituted or unsubstituted alkyl group having at most 7 carbon atoms, and R's may be the same or different;

B represents a substituted or unsubstituted oxyethylene group, or a substituted or unsubstituted oxypropylene group, and multiple continuing B's may be the same or different;

m indicates a number of 1 or more;

$Z^1$ represents a single bond, or a divalent group selected from the group consisting of a carbonyl group, a sulfonyl group, a phosphoryl group, an oxy group, a substituted or unsubstituted amino group, a sulfide group, an alkenylene group, an alkynylene group and an arylene group, and any combinations of two or more of those groups.

2. The composition according to claim 1, wherein A in the formula (Z) is a residue of pentaerythritol, glycerol, oligopentaerythritol, xylitol, sorbitol, inositol, trimethylolpropane, ditrimethylolpropane, neopentyl glycol or polyglycerin.

3. The composition according to claim 1, wherein A in the formula (Z) is a group represented by any of the following (AI) to (AIII):

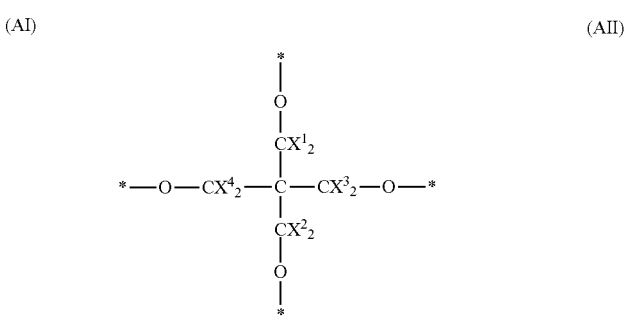

-continued (AIII)

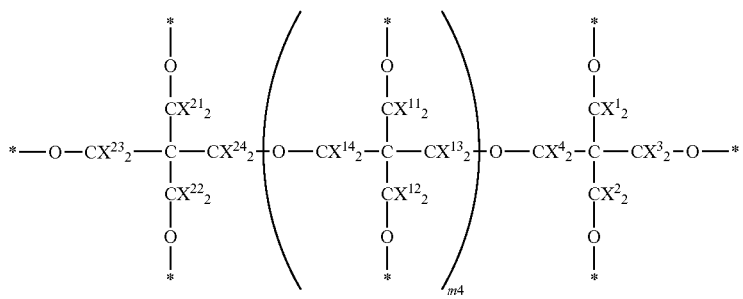

wherein * means a site at which the formula bonds to -L-D$^1$-(E)$_q$-D$^2$-(B)$_m$—Z$^1$—R; C represents a carbon atom; R$^0$ represents a hydrogen atom or a substituent; X$^1$ to X$^4$, X$^{11}$ to X$^{14}$, and X$^{21}$ to X$^{24}$ each represent a hydrogen atom, or a halogen atom, and they may be the same or different; n1 to n3 each indicate an integer of from 0 to 5; m4 indicates an integer of from 0 to 8.

4. The composition according to claim 3, which comprises the compound represented by the formula (AII) in an amount of from 50 to 95% by mass, and further the compound represented by the formula (AIII) and/or the following formula (AIII') in an amount of from 5 to 50% by mass:

(AIII')

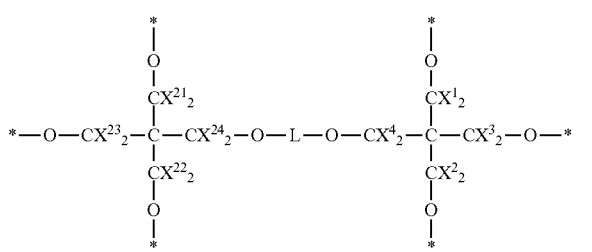

wherein * means a site at which the formula bonds to -D$^1$-(E)$_q$-D$^2$-(B)$_m$—Z$^1$—R; C represents a carbon atom; X$^1$ to X$^4$, X$^{11}$ to X$^{14}$, and X$^{21}$ to X$^{24}$ each represent a hydrogen atom, or a halogen atom, and they may be the same or different; L represents CH$_2$ or CO(CH$_2$)$_k$CO; k indicates an integer of from 1 to 10.

5. The composition according to claim 1, wherein A in the formula (Z) is a residue of a polymer or an oligomer represented by any of the following formulae (AIV) to (AVIII):

(AIV)

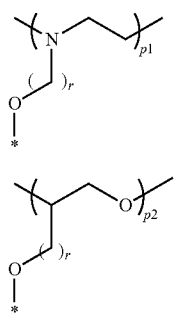

(AV)

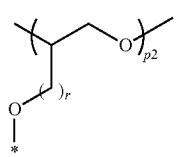

-continued (AVI)

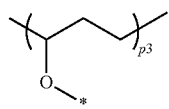

(AVII)

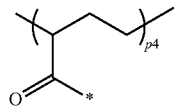

(AVIII)

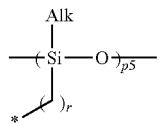

wherein * means the site at which the formula bonds to -L-D$^1$-(E)$_q$-D$^2$-(B)$_m$—Z$^1$—R;
the hydrogen atom bonding to the carbon atom in the formulae may be substituted with a C$_1$ to C$_4$ alkyl group or a halogen atom, and in case where the formula has 2 or more substituents, they may be the same or different; Alk represents a C$_1$ to C$_6$ alkyl group, or a cycloalkyl group; p1 to p5 each indicate a number of 2 or more; r indicates an integer of from 1 to 3.

6. The composition according to claim 1, wherein A in the formula (Z) is a residue of dithiocarbamic acid or dithiophosphoric acid ion-bonding or coordinate-bonding to zinc or molybdenum.

7. The composition according to claim 1, wherein -(B)$_m$—Z$^1$—R in the formula (Z) is an organic group represented by the following formula (ECa), and multiple groups may be the same or different:

(ECa)

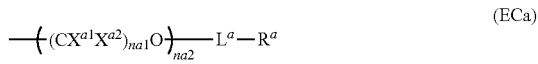

wherein C represents a carbon atom; O represents an oxygen atom; R$^a$ corresponding to R in the formula (Z) represents a substituted or unsubstituted alkyl group having at most 7 carbon atoms; L$^a$ corresponding to Z$^1$ in the formula (Z) represents a single bond or a divalent linking group selected from a carbonyl group, a sulfonyl group, a phosphoryl group, an oxy group, a substituted or unsubstituted amino group, a sulfide group, an alkenylene group, an alkynylene group and an arylene group, or a combination of those groups; X$^{a1}$ and X$^{a2}$ each represent a hydrogen atom or a halogen atom; na1 indicates 2 or 3, and when na1 is 2 or more, multiple $X^{a1}$'s and $X^{a2}$'s may be the same or different; na2 indicates a number of from 1 to 12.

8. The composition according to claim 7, wherein $L^a$ corresponding to $Z^1$ in the formula (Z) is a divalent linking group formed of a combination of one or more selected from a single bond, a carbonyl group, a sulfonyl group, a phosphoryl group, an oxy group, a substituted or unsubstituted amino group, a thio group, an alkylene group, an alkenylene group, an alkynylene group, and an arylene group.

9. The composition according to claim 1, wherein R in the formula (Z) is a group comprising a linear alkyl group having at most 4 carbon atoms.

10. The composition according to claim 1, wherein m of $(B)_m$ in the formula (Z) is from 2 to 6.

11. The composition according to claim 1, wherein the viscosity-pressure coefficient at 40° C. of the compound represented by the formula (Z) is at most 15 $GPa^{-1}$.

12. The composition according to claim 1, which comprises water, a linear or branched alcohol having at most 12 carbon atoms, ethylene glycol, polyethylene glycol, mineral oil, poly-α-olefin, polyol ester, (poly)phenyl ether, ionic liquid, silicone oil, fluorine oil, or at least two selected from these, along with at least one compound represented by the formula (Z).

13. The composition according to claim 1, wherein the constituent elements of all the ingredients are one or more alone selected from carbon, hydrogen, oxygen and nitrogen.

14. The composition according to claim 1, which comprises the compound represented by the formula (Z) in an amount of at least 10% by mass.

15. The composition according to claim 1, which has a viscosity at 40° C. of at most 30 mPa·s.

16. The composition according to claim 1, which further comprises at least one selected from organic zinc compounds, molybdenum compounds, organic phosphorus compounds and organic sulfur compounds.

17. The composition according to claim 1, which is used for lubrication of the sliding interface of inorganic materials or their porous materials, or resins or their porous materials.

18. The composition according to claim 1, which is a mold release agent.

19. The composition according to claim 1, which is a fuel for combustion engines.

20. The composition according to claim 1, which is an internal combustion engine oil.

21. The composition according to claim 1, which is a bearing oil.

22. The composition according to claim 1, which is a grease oil.

23. The composition according to claim 1, which is a cutting oil.

24. A method for forming a coating film, which comprises disposing the composition of claim 1 between two faces and sliding the two faces to thereby form a coating film of the composition on at least one of the faces.

* * * * *